(12) United States Patent
Alam et al.

(10) Patent No.: US 9,683,241 B2
(45) Date of Patent: Jun. 20, 2017

(54) POLYNUCLEOTIDES ENCODING ENZYMES FROM THE JUTE LIGNIN BIOSYNTHETIC PATHWAY

(75) Inventors: Maqsudul Alam, Honolulu, HI (US); Haseena Khan, Dhaka (BD); Mahboob Zaman, Dhaka (BD); Mohammed K. Uddin, Dhaka (BD); Mohammed S. Haque, Dhaka (BD); Mohammed S. Islam, Dhaka (BD); Muhammad S. Azam, Dhaka (BD)

(73) Assignee: Bangladesh Jute Research Institute, Dhaka (BD)

( * ) Notice: Subject to any disclaimer, the term of this patent is extended or adjusted under 35 U.S.C. 154(b) by 717 days.

(21) Appl. No.: 14/114,623

(22) PCT Filed: Apr. 25, 2012

(86) PCT No.: PCT/US2012/034980
§ 371 (c)(1),
(2), (4) Date: May 19, 2014

(87) PCT Pub. No.: WO2012/149009
PCT Pub. Date: Nov. 1, 2012

(65) Prior Publication Data
US 2014/0344997 A1 Nov. 20, 2014

Related U.S. Application Data
(60) Provisional application No. 61/480,668, filed on Apr. 29, 2011.

(51) Int. Cl.
*C12N 15/82* (2006.01)
*C12N 9/04* (2006.01)
*C12N 9/02* (2006.01)
*C12N 9/10* (2006.01)
*C12N 9/00* (2006.01)

(52) U.S. Cl.
CPC ....... *C12N 15/8255* (2013.01); *C12N 9/0006* (2013.01); *C12N 9/0008* (2013.01); *C12N 9/0073* (2013.01); *C12N 9/1007* (2013.01); *C12N 9/93* (2013.01); *C12N 15/8261* (2013.01); *C12N 15/8279* (2013.01)

(58) Field of Classification Search
None
See application file for complete search history.

(56) References Cited

U.S. PATENT DOCUMENTS

| 8,247,651 B2* | 8/2012 | Puzio | C07K 14/245 435/320.1 |
| 2010/0175144 A1 | 7/2010 | Swaller | |
| 2013/0167265 A1* | 6/2013 | Panik | C07K 14/415 800/278 |

FOREIGN PATENT DOCUMENTS

| WO | WO-2008/069878 A2 | 6/2008 |
| WO | WO-2012/149009 A2 | 11/2012 |

OTHER PUBLICATIONS

Barakat et al, 2009, BMC Plant Biology, 9:1-5.*
Ralph et al, 2008, BMC Genomics 9, 57:1-18.*
Fan, L. et al., "Molecular and Biochemical Evidence for Phenylpropanoid Synthesis and Presence of Wall-linked Phenolics in Cotton Fibers," Journal of Integrative Plant Biology, 51(7):626-637 (2009).
Goujon, T. et al., "Genes Involved in the Biosynthesis of Lignin Precursors in *Arabidopsis thaliana*," Plant Physiology and Biochemistry, 41:677-687 (2003).
Kovalic, D.K. et al., "Cotton Protein for Improving Plant Biological Properties," (2008) XP-002746117.
Leple, J-C., "Downregulation of Cinnamoyl-Coenzyme A Reductase in Poplar: Multiple-Level Phenotyping Reveals Effects on Cell Wall Polymer Metabolism and Structure," The PlantCell, 19:3669-3691 (2007).
Meyermans, H. et al., "Modifications in Lignin and Accumulation of Phenolic Glucosides in Poplar Xylem upon Down-regulation of Caffeoyl-Coenzyme A O-Methyltransferase, an Enzyme Involved in Lignin Biosynthesis," The J. of Biological Chemistry, 275(47):36899-36909 (2000).
Sengupta, G. et al., "Characterization of a Lignified Secondary Phloem Fibre-deficient Mutant of Jute (*Chorchorus capsularis*)," Annals of Botany, 93:211-220 (2004).
Shadle, G. et al., "Down-regulation of Hydroxycinnamoyl CoA: Shikimate Hydroxycinnamoyl Transferase in Transgenic Alfalfa Affects Lignification, Development and Forage Quality," Phytochemistry, 68:1521-1529 (2007).
Shi, R. et al., "Towards a Systems Approach for Lignin Biosynthesis in *Populus trichocarpa*: Transcript Abundance and Specificity of the Monolignol Biosynthetic Genes," Plant Cell Physiol., 51(10):144-163 (2010).
Tan, X. et al., "Camellia Oleifera Cinnamoyl-CoA Reductase (CCR) mRNA, Completed cds" (2009) XP002746118.
Vanholme, R. et al., "Lignin Engineering," Plant Biology, 11:278-285 (2008).
Wadenback, J. et al., "Lignin Biosynthesis in Transgenic Norway Spruce Plants Haboring an antisense Construct for Cinnamoyl CoA Reductase (CCR)," Transgenic Res., 17:379-392 (2008).
Ye, Z-H. et al., "Differential Expression of Two-O-Methyltransferases in Lignin Biosynthesis in *Zinna elegans*[1]," Plant Physiol., 108:459-467 (1995).
European Search Report for EP 15 17 4705 completed on Sep. 30, 2015.

(Continued)

*Primary Examiner* — Jason Deveau Rosen
(74) *Attorney, Agent, or Firm* — Foley Hong LLP

(57) ABSTRACT

Disclosed are polynucleotides encoding polypeptides that comprise the biosynthetic pathway for lignin in the jute plant. The present invention relates generally to the field of plant lignin biosynthesis genes, polypeptides encoded by such genes, and the use of such polynucleotide and polypeptide sequences for controlling plant lignin production. Also disclosed are methods for using the polynucleotides and polypeptides to influence the quality and amount of fiber produced by jute.

15 Claims, 18 Drawing Sheets

(56) References Cited

OTHER PUBLICATIONS

European Search Report for EP 15 17 4686 completed on Oct. 13, 2015.
European Search Report for EP 15 17 4696 completed on Sep. 29, 2015.
European Search Report for EP 15 17 4702 completed on Oct. 13, 2015.
Alam, M. et al., "Putative Leucine-Rich Repeat Receptor-Like Kinase of Jute Involved in Stress Response," Plant Mol. Biol. Rep, 28:394-402 (2010).
Fan et al., "Genes of phenylpropanoid pathway cloning and expression in developing cotton fiber," Institute of Nuclear and Biological Studies, 2 pages, Unpublished, Submitted Oct. 10, 2008.
Rashid et al., "Bangladesh decoded Jute's genome sequencing," Bangladesh Textile Today, 7 pages, 2010.
Stephens et al., "Lignin manipulation for fibre improvement," P. Ranalli (ed.), Improvement of Crop Plants for Industrial End Uses, pp. 129-153 (2007).
Extended European Search Report for EP 12776946.1 mailed Mar. 27, 2015.
del Rio, Jose C., et al. Structural Characterization of the Lignin from Jute (*Corchorus capsularis*) Fibers, J. Agric. Food Chem., 57: 10271-10281 (2009).
Samanta, Pradipta, et al. "Isolation of RNA from Field-Grown Jute (*Corchorus capsularis*) Plant in Different Developmental Stages for Effective Downstream Molecular Analysis," Mol. Biotechnol., 49: 109-115 (2011).
XP002731964 dated Sep. 23, 2008.
XP002731965 dated Jan. 11, 2011.
Supp. Partial European Search Report for EP 12776946 mailed Nov. 4, 2014.
Genbank Accession No. ABZ01817 "Cinnamyl alcohol dehydrogenase [*Gossypium hirsutum*]," 2009 <http://www.ncbi.nlm.nih.gov/protein/166865124?report=genbank&log$=protalign&blast_rank=2&RID=77ATC3KE01R>.
Genbank Accession No. ACC63874 "cinnamyl alcohol dehydrogenase [*Populus trichocarpa*]," 2010 <https://www.ncbi.nlm.nih.gov/protein/183585165?report=genbank&log$=protalign&blast_rank=8&RID=Z8K0JJ7S014>.
Genbank Accession No. NP177412 "cinnamyl-alcohol dehydrogenase, putative [*Arabidopsis thaliana*]," 2009 <https://www.ncbi.nlm.nih.gov/protein/15218564?sat=14&satkey=6640086>.
Genbank Accession No. XP002322761 "cinnamyl alcohol dehydrogenase-like protein [*Populus trichocarpa*]," 2009 <https://www.ncbi.nlm.nih.gov/protein/224138226?sat=13&satkey=50021>.
Genbank Accession No. ACF71455.1 GI: 194554813 "Cinnamyl alcohol dehydrogenase [*Gossypium hirsutum*]," 2008.
Genbank Accession No. ACQ59091.1 GI: 229368450 "Cinnamyl alcohol dehydrogenase 3 [*Gossypium hirsutum*]," 2010.

* cited by examiner

```
ColCAD1                 -MGSLPEQEHPKEAFGWAARDTSGHLSPFKFSRRATGEKDVAFKVLYCGICHSDLHMIKN  59
ColCAD2                 -MSRLPEEEHPNKAFGWAARDTSGVLSPFKFSRRATGEKDVAFKVLYCGICHSDLHMVKN  59
PtcCADgi_224138226      MADKLFEEEHPKPAFGWAARDQSGVLSPFKFSRRATGEKDVAFKVLYCGICHSDLHMVKN  60
RcoCADgi_255587709      MVANLFEKDHPRKAFGWAARDQSGVLSPFTFSRRETGEKDVSFKVLYCGMCHSDLHMVKN  60
ColCAD3                 ------------------------------------------------------MIKN   4
FraCADgi_13507210       ---MSIEQEHPNKASGWAARDSSGVLSPFNFSRRETGEKDVMFKVLYCGICHSDHHMVKN  57
ColCAD5                 MAKSSPEEEHPVKAFGWAARDTSGHLSPFNFSRRATGEGDVRFKVLYCGICHSDLHPIKN  60
PtcCADgi_183585165      MSKS-PEEEHPVKAFGWAARDQSGHLSPFNFSRRATGEEDVRFKVLYCGICHSDLHSIKN  59
ColCAD6                 --MAMETPNHTQTVAGWAAHNSSGKIVPYTFKRRENGVNDVTIKVMYCGICHTDLHHVKN  58
GhiCAD3gi_229368450     --MALETPNHTQTVAGWAAYDSSGKIAPYIFKRRENGVNDVTIQVMYCGICHTDLHHVKD  58
ColCAD7                 ----MGSLETERTTTGWAARDPSGVLSPYTYTLRNTGPEDVFIKVICCGICHTDLHQAKN  56
GhiCADgi_166865124      ----MGSLETERTTTGWAARDPSGVLSPYTYTLRNTGPEDVPVKVMCCGICHTDLHQAKN  56
ColCAD4                 ----MDSQTKSDNCLGWAARDPSGVLSPYTFSRRPLGSNDVSIKITHCGVCYADFIWSRN  56
ChiCAD5gi_268528129     ----MDSQTKTENCLGWAATDPTGVLSPYKFSRRPLGSDDVSIKITHCGVCYADVIWSRN  56
                                                                                  : :

ColCAD1                 EWGTAIYPMVPGHEIVGEVTEVGSKVEKPKVGDKVGAGVLVNSCRSCDNCANNLENYCPQ 119
ColCAD2                 EWGVSIYPLVPGHEIVGEVTEVGSKVQKPKVGDRVGVGCMVGSCHSCDSCTNNLENYCPK 119
PtcCADgi_224138226      EWGVTQYPLIPGHEIVGVVTEVGSKVEKPKVGDKVGVGCMVGSCRSCDSCTNNLENYCSK 120
RcoCADgi_255587709      EWGTSTYPLVPGHEIVGVVTEVGSKVEKIKVGDKVGVGCMVGSCRSCNNCRKDLENYCPK 120
ColCAD3                 DWGYSIYPLVPGHEIVGEVTEVGSKVSKPKVGDKVGVGYMVGSCPSCDDCSDNLENYCPK  64
FraCADgi_13507210       EWGFSTYPLVPGHEIVGEVTEVGSKVQKPKVGDRVGVGCIVGSCRSCENCTDHLENYCPK 117
ColCAD5                 EWNFSIYPLVPGHEIVGVVKVKIGDKVGVGCIIGACHTCESCANDLENYCPK 120
PtcCADgi_183585165      DWGFSMYPLVPGHEIVGEVTEVGSKVKKVNVGDKVGVGCLVGACHSCESCASDLENYCPK 119
ColCAD6                 DWGITMYPVVPGHEITGVITKIGNNVKNFKVGDRVGVGCLAASCLECEFCKSSQENYCEQ 118
GhiCAD3gi_229368450     DWGITMYPVVPGHEITGVITKVGSNVKNFKLGDRVGVGCLAASCLECEFCKNSQENYCEQ 118
ColCAD7                 DLGMSNYPMVPGHEVVPGEVLEVGSQVTKFRVGEIVGVGCIVGCCRNCRPCNTDNEQYCNK 117
GhiCADgi_166865124      DLGMSNYPMVPGHEVVGEVLEVGSDVSKFRVGDIVGVGCLVGCCRNCRPCDSDNEQYCLK 116
ColCAD4                 KHGDSMYPVVPGHEIAGVVKEVGSNVHRFKVGDPVGVGTYVNSCRDCEYCNDGLEVHCEK 116
ChiCAD5gi_268528129     MFGDSIYPLVPGHEIAGIVKEVGSNVQRIKVGDLVGVGTYVNSCRNCEYCNDGVEVQCVK 116
                         . :  ** :****:.*  :  ::*..*   ...:*:  **.*    .*   *     *  :

ColCAD1                 -AVFTYAAKNYDGTITYGGYSDTMVADEHFIIRIPDTLPLDAAAPLLCAGITVYSPLRYF 178
ColCAD2                 -MILTYGAKYYDGTITYGGYSDTMVADEHFIVRIPENLPLDAAAPLLCAGITVYSPLKYY 178
PtcCADgi_224138226      -KILTYGAKYYDGTVTYGGYSDNMVADEHFIVRIPNNLPLDAGAPLLCAGITVYSPLRYF 179
RcoCADgi_255587709      -MILTYGAKYYDGTTTYGGYSDIMVSDEHFVVRIPDNLPLDATAPLLCAGITVYSPLKYY 179
ColCAD3                 -MIPTCGAKYHDGTITYGGFSDTMVADEHFVVRIPDNMPLDAAAPLLCAGTTVYSPMKYY 123
FraCADgi_13507210       -QILTYGANYYDGTTTYGGCSDIMVAHEHFVVRIPDNLPLDGAAPLLCAGITTYSPLRYF 176
ColCAD5                 -AIATYNGTYYDGTMTYGGYSDSMVADERYVVQIPDGMALDSAAPLLCAGITVYSPLKYF 179
PtcCADgi_183585165      -MILTYASIYHDGTITYGGYSDHMVAMERYIIRFPDNMPLDGGAPLLCAGITVYSPLKYF 178
ColCAD6                 -IQFTYNGIFWDGSVTYGGYSQMLVADHRYVVRVPDNLPMDAAAPLLCAGITVFSPMKES 177
GhiCAD3gi_229368450     -IQFTYNGIFWDGSITYGGYSEMLVADHRYVVHVPDNLPMDAAAPLLCAGITVFSPMKDC 177
ColCAD7                 -KIWSYNDVYTDGKPTQGGFAASMVADQKFVVKIPDGMAAEQVAPLLCAGVTVYSPLKHF 175
GhiCADgi_166865124      -KIWSYNDVYTDGKPTQGGFAGSMVVDQKFVVKIPEGMAPEQVAPLLCAGVTVYSPLNHF 175
ColCAD4                 -IVLTFNCIDEDGTVTKGGYSNHIIVHERYCLRIFSNYPLASAAPLLCAGITVYAPMMRH 175
ChiCAD5gi_268528129     GPVLTFNHIDIDGTVTKGGYSSHIVVHERYCFKIPNNYPLASAAPLLCAGITVYTPMMRY 176
                           :          **.*  **  ::  ..::   .:.*.  .  ******* *.:  *:

ColCAD1                 Q-LDKPGFHIGVVGLGGLGHMAVKFAKAMGAKVTVISTSPNKKKEALENLGADSFLISAE 237
ColCAD2                 G-LDKPGLHVGVVGLGGLGHMAVKFAKAMGAKVTVISTSPNKKKEALENLGADSFLVSKD 237
PtcCADgi_224138226      G-LDKPGMHVGIVGLGGLGHVAVKFARAMGVKVTVISTSPNKKQEALENLGADSFLVSRD 238
RcoCADgi_255587709      G-LDKPGMQIGVVGLGGLGHMAVKFAKAMGAKVTVISTSPNKKQEATERLGADSFLVSRD 238
ColCAD3                 G-LDKPGLHLGVVGLGGLGHMAVKFAKAMGVKVTVISTSPSKKQEALEILGADSFLVSRD 182
FraCADgi_13507210       G-LDKPGMHVGVVGLGGLGHVAVKFAKAMGVKVTVISTSPKKEEEALKHLGADSFLVSRD 235
ColCAD5                 G-LGEAGNHIGIVGLGGLGHVAVKFAKALGSKVTVISTSPGKKKEALELLGADSFLVSRD 238
PtcCADgi_183585165      G-LDEPGKHIGIVGLGGLGHVAVKFAKAFGSKVTVISTSPSKKEEALKNLGADSFLVSRD 237
ColCAD6                 QLLESPGKKVGIVGLGGLGHMAVKMAKAFGHHVTVISTSPSKEKEAKQRLGADDFIVSTN 237
GhiCAD3gi_229368450     QLLESPGKKVGIVGLGGLGHVAVKMAKAFGHQVTVISTSPSKENEAKQRLGADYFLVSTD 237
ColCAD7                 G-LMESGLRGGILGLGGVGHMGVKIAKAMGHHVTVISSSDKKKVEALEHLGADDYVVSSD 234
GhiCADgi_166865124      G-LMGSGLRGGILGLGGVGHMGVKIAKAMGHHVTVISSSDKKKVEALEHLGADDYLVSSD 234
ColCAD4                 N-MNQPGKSLGVIGLGGLGHMAVKFGKAFGLHVTVLSTSISKKDEALSLLGADNFVVSSD 234
ChiCAD5gi_268528129     N-MNQPGKSLGVIGLGGLGHMAVKFGKAFGLSVTVLSTSISKKEEALSLLGADNFVVTSD 235
                         . .*   *::*****:**:.**::*.*    ***:*:*   *: **   .   **** :::: :
```

Figure 2a

```
ColCAD1              QDQLQTAMGTMDGIIDTVSAPEPLLPLIGLLKSHAKLILVGLPDKPLELHVFPMIIGRKT 297
ColCAD2              QDQIQAAMDTLDGIIDTVSAQEPILPLLGMLKTNGKLVLVGAPEKPLELPAFPLLGKRRL 297
PtcCADgi_224138226   QDQMQAAMGTLDGIIDTVSAVEPLLPLVALLKSHGKLVLVGAPEKPLELPVFPLITGRKT 298
RcoCADgi_255587709   QDQMKGAIGTMDGIIDTVSAMEPLSPLIGLLKSDGKLVLVGAPEKPLELPAFPLIGGRKL 298
ColCAD3              EDQLKAAKGTMNGIVDTVSAKEDLQPLLGLLKNHGKLVLIGVPVKPYELPAASLILGRKL 242
FraCADgi_13507210    QDHMQAAIGTMDCIIDTVSAQEPLLPLIGLLKSHCKLVMVGAPEKPLELPVFPLLMGRKM 295
ColCAD5              QDEMQAAMGTLDGIIDTVSAVEPIMPLLGLLKSHGKLIMVGAPIEPLELPVFSLIMGRKT 298
PtcCADgi_183585165   QFQMQAAAGTLDGIIDTVSAVEPLLPLFGLLKSHGKIILVGAPEKPLELPAFSLTAGRKT 297
ColCAD6              TEQMQRGKRTLDVILDTVSAKESLGPILEELKVNGTLVVVGAPDKPIDLPSFPLIFGKRA 297
GhiCAD3gi_229368450  AKQMQRGKRTLDVILDTVSAKESLGPILEELKVNGTLVVVGAPDRPIELPSFPLIFGKRA 297
ColCAD7              AESMQKIADSLDYIIDTVPVFEPLEPYLSVLKLDGKLILTGVINTPLQFVTPMVMLGRKV 294
GhiCADgi_166865124   AEGMQKAADSLDYIIDTVPVFEPLEPYLSLLKPDGKLILTGVINTPLQFVSPMVMLGRKS 294
ColCAD4              OEQMKGLSKSLDFIVDTASGDEPFDPYMSLLKIAGVYVLVGFP-SEVKFSPASLNLGMRT 293
ChiCAD5gi_268528129  QEQMKGLSKSLDFIIDTASGDEPFDPYLSLLKSACVYALVGFP-SEIKFSPASLNPGMKT 294
                       ::    :::  *:**..  *  :  .:**        :  *       .:    :    :

ColCAD1              VAGSGVGGIEETQEMMNFAAKYDLKPDIEVIPVDYVNTAMERLVKGDVKYRFVIDIGNTL 357
ColCAD2              VAGSMIGGMKETQEMIDFAAKENIKPDIEVIAMDYVNTAMDRLLKADVKYRFVIDIGNTL 357
PtcCADgi_224138226   VGGSCVGGIKETQEMIDFAAKENITADIEVIPMDYVNTAMERVLKADVRYRFVIDVGKTL 358
RcoCADgi_255587709   VGGSCIGGMKETQEMIDFAAKESITADIEVIPANYVNTAMERMLKADVRYRFVIDIGNTL 358
ColCAD3              VGGSNVGGLEETQEMIDFAAKENVTANVEVIPMDYVNTAFERLAKADVRYRFVVDIGNTL 302
FraCADgi_13507210    VAGSGIGGMMETQEMIDFAAKENITADIEVIPIDYLNTAMERLVKADVRYRFVIDIGNTL 355
ColCAD5              MAGSGIGGMKETQEMIDFAAKENIKADIEVIPMDYVNKAMERLEKGDVRYRFVIDIGNTL 358
PtcCADgi_183585165   VAGSGIGGMKETQEMIDFAAKENITADIEVISTDYLNTAMERLAKNDVRYRFVIDYGNTL 357
ColCAD6              VKGSMTGGMKETQEMMDVCGKENITCDIEVIKPDQINEALDRLSKNDVRYRFVIDIAGRS 357
GhiCAD3gi_229368450  VKGSMTGGMKETQEMMDVCGKENITCDVELIKPDKINQALDRLARNNDVRYRFVIDIAGTS 357
ColCAD7              ITGSFVGSMKETEEMLDFCKEKDLNSMIEVVKMDYINTAMERLEKNDVRYRFVVDVAGSK 354
GhiCADgi_166865124   ITGSFIGSMKETEEMLNFCKEENLTSMIEVVKMDYINTAMERLEKNDVRYRFVVDVAGSK 354
ColCAD4              ISGSVTGGVKVIQEMIDFCAAEKVYPQIEVIPIQYANEALERLEKRDVKYRFVIDIENSL 353
ChiCAD5gi_268528129  FAGSVTGGTKMIQEMIGFCAARKIYPQIEVIPIQYANEALERLVKKDVKYRFVIDIENTL 354
                     . **  *.    :**:...   .:   :*::     :  * *::*:  : **:****:*:

ColCAD1              KATSS 362(SEQ ID NO: 2)
ColCAD2              KFTP- 361(SEQ ID NO: 4)
PtcCADgi_224138226   KPDV- 362(SEQ ID NO: 63)
RcoCADgi_255587709   KPGH- 362(SEQ ID NO: 64)
ColCAD3              KTSS- 306(SEQ ID NO: 6)
FraCADgi_13507210    KASS- 359(SEQ ID NO: 65)
ColCAD5              ATTKP 363(SEQ ID NO: 10)
PtcCADgi_183585165   AATKP 362(SEQ ID NO: 66)
ColCAD6              KL--- 359(SEQ ID NO: 12)
GhiCAD3gi_229368450  KL--- 359(SEQ ID NO: 67)
ColCAD7              LE--- 356(SEQ ID NO: 14)
GhiCADgi_166865124   LDQ-- 357(SEQ ID NO: 68)
ColCAD4              K---- 354(SEQ ID NO: 8)
ChiCAD5gi_268528129  K---- 355(SEQ ID NO: 69)
```

Figure 2b

```
ColCCoAOMT2              -MATN-TQEQQTQAGRHQEVGHKSLLQSDALYQYILETSVYPREPEPMKE  48
GhiCCoAOMT2gi_229368460  -MATNTTQEQQPAAGRHQEVGHKSLLQSDALYQYILETSVYPMEPEPMKE  49
PtrCCoAOMTgi_3023436     -MATN-GEEQQSQAGRHQEVGHKSLLQSDALYQYILETSVYPREPECMKE  48
ColCCoAOMT1              -MAPT-QAEQQTQASRHQEVGHKSLLQSDKLYQYILETSVYPREPEAMKE  48
ColCCoAOMT3              MGSTGETQFTPTQVSDEEANLFAMQLASASVLPMVLKSAIELDLLEVMAK  50
GhiCCoAOMT1gi_253509567  MGSIGETQMTPTQVSDDEANLFAMQLASASVLPMVLKSAIELDLLEIMAK  50
                           :       . ...:  .   * * :   :*::: :    * *  :

ColCCoAOMT2              LRELTAKHP----WNLMTTSADEGQFLNMLLKLINAKNTMEIGVY-----  89
GhiCCoAOMT2gi_229368460  LRELTAKHP----WNLMTTSADEGQFLNMLLKLINAKNTMEIGVY-----  90
PtrCCoAOMTgi_3023436     LREVTAKHP----WNIMTTSADEGQFLNMLLKLVNAKNTMEIGVY-----  89
ColCCoAOMT1              LRELTAKHP----WNLMTTSADEGQFLNMLLKLINAKNTMEIGVY-----  89
ColCCoAOMT3              AGPGAFLSPTEVASQLPTKNPDAPVMLDRILRLLASYSILTCSLRNLPDG 100
GhiCCoAOMT1gi_253509567  AGPGAFLSPKEVASKLPTTNPDAPVMLDRILRLLASYNVLTCSLRTFPGG 100
                          :    *    ::  *...*   :*:  :*:*:  :  .  :    .:

ColCCoAOMT2              -----TGYSLLATALALPDDGKILAMD--INRENYELG-LPVIQKAGVAH 131
GhiCCoAOMT2gi_229368460  -----TGYSLLATALALPDDGKILAMD--INRENYELG-LPVIRKAGVAH 132
PtrCCoAOMTgi_3023436     -----TGYSLLATALAIPEDGKILAMD--INRENYELG-LPVIQKAGVAH 131
ColCCoAOMT1              -----TGYSLLATALALPEDGKILAMD--INRENYELG-LPVIQKAGVAH 131
ColCCoAOMT3              KVERLYGLGPVCKYLVKNEDGVALSALNLMNQDKVLMESWYYLKDAVLEG 150
GhiCCoAOMT1gi_253509567  KVERLYGLGPVCKFLTRNEDGVTLSALSLMNQDKVLMESWYYLKDAVLDG 150
                               *  . :.. *. :** *:   :*:::  :    ::.*  :

ColCCoAOMT2              KIEFKEGPALPVLDKLVEDEKNHGSYDFIFVDAD-------KDNYINYHK 174
GhiCCoAOMT2gi_229368460  KIEFKEGPAMPVLDKLVEDEKNHGSYDFIFVDAD-------KDNYLNYHK 175
PtrCCoAOMTgi_3023436     KIDFKEGPALPVLDQMIEDGKYHGSFDFIFVDAD-------KDNYINYHK 174
ColCCoAOMT1              KIDFKEGPALPVLDQMIEAGTYHGTFDFIFVDAD-------KDNYINYHK 174
ColCCoAOMT3              GIPFNKAYGMTAFEYHGTDPRFNKVFNRGMSDHSTITMKKILETYDGFEG 200
GhiCCoAOMT1gi_253509567  GIPFNKAYGMTAFEYHGTDPRFNKVFNRGMSDHSTITMKKILDTYDGFQG 200
                           * *::. .:..::          :  ::  : * .       :.* .::

ColCCoAOMT2              RLIDLVKVGG--------------------------------LIGYDNT 191
GhiCCoAOMT2gi_229368460  RLIELVKVGG--------------------------------LIGYDNT 192
PtrCCoAOMTgi_3023436     RLIELVKVGG--------------------------------LIGYDNT 191
ColCCoAOMT1              RLIELVKVGG--------------------------------VIGYDNT 191
ColCCoAOMT3              -LKTIVDVGGGVGATLNMIVSKHPSIKGINFDLPHVIEDAPALP-GVEHV 248
GhiCCoAOMT1gi_253509567  -LKTIVDVGGGTGATLSMIVSKYPTIKGINFDLPHVIEDAPSCPVGVEHV 249
                          *  **.***                                *  ::.

ColCCoAOMT2              LWNGSVVAPP-DAPLRKYVRYYR------DFVLELNKALAADP--RIEIC 232
GhiCCoAOMT2gi_229368460  LWNGSVVAPP-DAPLRKYVRYYR------DFVLELNKALAVDP--RIEIC 233
PtrCCoAOMTgi_3023436     LWNGSVVAPP-DAPMRKYVRYYR------DFVLELNKALAADP--RIEIC 232
ColCCoAOMT1              LWNGSVVAPP-DAPLRKYVLYYR------DFVLELNKALAADP--RIEIC 232
ColCCoAOMT3              GGDMFVSVPKGDAIFMKWICHDWSDEHCVKFLKKCYEALPDNGKVIVAEC 298
GhiCCoAOMT1gi_253509567  GGDMFVSVPKGDAIFMKWICHDWSDEHCAKFLKNCYEALPDNGKVIVAEC 299
                          :  .* .* ** :*::   :          .*: :  :**. :    :  *

ColCCoAOMT2              MLPVGDGITLCRRIK----------------------------------- 247
GhiCCoAOMT2gi_229368460  MLPVGDGITLCRRVK----------------------------------- 248
PtrCCoAOMTgi_3023436     MLPVGDGITLCRRIQ----------------------------------- 247
ColCCoAOMT1              QLPVGDGITLCRRIK----------------------------------- 247
ColCCoAOMT3              ILPDYPDASLATKLVVHIDCIMLAHNPGGKERTEKEFEALAKGAGFQGFQ 348
GhiCCoAOMT1gi_253509567  ILPDYPDPSLATKLVVHIDCIMLAHNPGGKERTAKEFEALAKGAGFQGFQ 349
                          **     . :*. ::

ColCCoAOMT2              -----------------(SEQ ID NO: 19)
GhiCCoAOMT2gi_229368460  -----------------(SEQ ID NO: 70)
PtrCCoAOMTgi_3023436     -----------------(SEQ ID NO: 71)
ColCCoAOMT1              -----------------(SEQ ID NO: 17)
ColCCoAOMT3              VKCCAFGTYIMEFLKTV 365(SEQ ID NO: 21)
GhiCCoAOMT1gi_253509567  ITCSAFGTNIMEFLKSV 366(SEQ ID NO: 72)
```

```
Co16HCT1              MIVNVKESTMVPPAEETPRVCLWNSNVDLVVPRFHTPSVYFYRPSGASNFFDPKVMKEAL 60
Ptc6HCTgi_183585181   MIINVKESTMVQPAEETPRRGLWNSNVDLVVPRFHTPSVYFYRPTGASNFFDAKVLKEAL 60
Cycar6HCTgi_73671233  MKIEVRESTMVRPAEETPRINLWNSNVDLVVPNFHTPSVYFYRPNGAANFFDPKVMKDAL 60
                      * ::*:***** ****** .*********** *********..*:.****.**:*:**

Co16HCT1              GKALVPFYPMAGRLKRDEDGRIEIDCNGAGVLFVEAETNAVIDDFGDFAPTLELRQLIPT 120
Ptc6HCTgi_183585181   SKALVPFYPMAGRLKRDDDGRIEIDCNAEGVLFVEAGTASVVADFGDFAPTLELKQLIPT 120
Cycar6HCTgi_73671233  SRALVPFYPMGGRLKRDEDGRIEIDCQCQGVLFVEAESDGVIDDFGDFAPTLELRKLIPA 120
                      .:********. *****:******* .**. :.* *********::**:

Co16HCT1              VDYSGGIETYPLLVLQVTYFKCGGASLGVGMQHHAADGFSGLHFINTWSDMARGLDLTIP 180
Ptc6HCTgi_183585181   VDYSGGISTYPLLVLQVTYFKCGGVSLGVGMQHHAADGFSGLHFVNTWSDMARGLDLTIP 180
Cycar6HCTgi_73671233  VDYTLGIESYSLLVLQVTYFKCGGVSLGVGMQHHAADGASGLHFINTWSDLARGLDLAVP 180
                      ***: **.:*.*************.************* *****:****:****** :*

Co16HCT1              PFIDRTLLRARDPPQPAFEHIEYQPPPALKSAPESTGSEG-----AAVSIFKLTREQLNA 235
Ptc6HCTgi_183585181   PFIDRTLLRARDPPQPAFHHVEYQPPPAMKTVLETSKPES-----TAVSIFKLTRDQLNT 235
Cycar6HCTgi_73671233  PFIDRTLLRSRDPPQPAFDHIEYQPAPPMKTAPTPTPTDDESVPETTVSIFKLTRDQVNA 240
                      *********:********.*:****.**:*:.  .:. ::      :*********:*:*.

Co16HCT1              LKAKSKFDGNTIAYSSYEMLSGHVWRSVCKARGLPDDQESKLYIATDGRARLRPPLPPGY 295
Ptc6HCTgi_183585181   LKAKAKEGGNNIGYSSYEMLAGHVWRSACKARGLPDDQETKLYIATDGRSRLRPTLPPGY 295
Cycar6HCTgi_73671233  LKGKSKEDGNTVNYSSYEMLSGHVWRCVCKARGLPDDQDTKLYIATDGRARLRPSLPRGY 300
                      **.*:**:.**.: ******:*****.***********::********:****.** **

Co16HCT1              FGNVIFTATPIAVAGELMSKPTWYAAGKIHDALVRMDNDYLKSALDYLELQPDLSALVRG 355
Ptc6HCTgi_183585181   FGNVIFTATPIAVAGEIQSKPTWYAAGKIHDSLVRMDNDYLRSALDFLELQPDLSALVRG 355
Cycar6HCTgi_73671233  FGNVIFTTTPIAVAGDLQSKPTWYAASKIHDALARMDDDYLKSALDYLELQPDLKALVRG 360
                      *******:*******: ********.****:*.***:***:****:******.*****

Co16HCT1              AHTFKCPNLGITSWSRLPIHDADFGWGRPIFMGPGGIPYEGLSFVLPSPTNDGSLSVAIA 415
Ptc6HCTgi_183585181   AHTFRCPNLGITSWVRLPIHDADFGWGRPIFMGPGGIAYEGLSFIIPSSTNDGSLSVAIS 415
Cycar6HCTgi_73671233  AHTFKCPNLGITSWARLPIHDADFGWGRPIFMGPGGIAYEGLSFVLPSPINDGSLSIVIS 420
                      ****:********* ********************* ******::**. ******:.*:

Co16HCT1              LQTEHMKLFEKIFYDDI-- 432(SEQ ID NO: 32)
Ptc6HCTgi_183585181   LQAEHMKLFEKFIYDIKE  433(SEQ ID NO: 76)
Cycar6HCTgi_73671233  LQAEHMKLFSKFLYDI--  436(SEQ ID NO: 77)
                      **:******.*::**
```

Figure 5

```
EglC3Hgi_295413824    MALPLILLSIPLLFLLLAHQLYQRLRFKLPPGPRAWPVVGNLYDIKPVRFRCFAEWSQAY 60
Palxpgrgi_166209291   --MNLLLIPISFITILLTYKIYQRLRFKLPPGPRPWPIVGNLYDVKPVRFRCFAEWAQAY 58
ColC3H                ------------------------------------------------------------
Ptcgi_224139664       -MALPLLVLVSIFVLLLAYILYQRLRFKLPPGPRPWPIVGNLYAIKPIRFRCFAEWAQAY 59

EglC3Hgi_295413824    GPIISVWFGSTLNVVVSSSELAKEVLKENDQQLADRHRSRSAAKFSRDGQDLIWADYGPH 120
Palxpgrgi_166209291   GPIISVWFGSTLNVIVSNTELAKEVLKENDQQLADRHRSRSAAKFSRDGKDLIWADYGPH 118
ColC3H                ------------------------------------------------------------
Ptcgi_224139664       GPVVSVWFGSTLNVVVCNAELAKQVLKENDQQLADRHRSRLAARFSRDGKDLIWADYGPH 119

EglC3Hgi_295413824    YVKVRKVCTLELFTPKRLEALRPIREDEVTAMVESIFKDCTNPDNSGKTLLVKKYLGAVA 180
Palxpgrgi_166209291   YVKVRKVCTLELFSPKRLEALRPIREDEVTAMVESIFNDCTNPENNGKTLMVKKYLGAVA 178
ColC3H                ---------------------MPIS---------------DAESKNKTLQVRDYLGAVA 23
Ptcgi_224139664       YVKVRRVSTLELFSAKRLEELRPIREDEVTFMAESIFKDCTNPENHGKSLLVKKYLGDVA 179
                                           **           :.: .*:* *:.*** **

EglC3Hgi_295413824    FNNITRLAFGKRFMNAEGVIDEQGLEFKAIVSNGLKLGASLAMAEHIPWLRWMFPLEEEA 240
Palxpgrgi_166209291   FNNITRLAFGKRFENAEGVMDEQGLEFKAIVSNGLKLGASLAMAEHIPWLRWMFPLEEDA 238
ColC3H                FNNITRLVFGKRFMNSEGIIDEQGKEFKGIVSNGTKIGASLAMAEHIPWLRWMFPLEEEA 83
Ptcgi_224139664       FNNITRLAFGKRFMNSEGIIDEQGQEFKAIVSNGVRLGGSLTMAEHIPWLQWMFPLEEEA 239
                     *******.***** *:**:;****.***.*****  ::*.**:*******:*******:*

EglC3Hgi_295413824    FAKHSARRDRLTRAIMEEHTVARQKSG-AKQHFVDALLTLKDKYDLSEDTIIGLLWDMIT 299
Palxpgrgi_166209291   FAKHGARRDRLTRAIMDEHTLARQTSGGAKQHFVDALLTLQEKYDLSEDTIIGLLWDMIT 298
ColC3H                FAKHAARRDNLTRTIMEEHTAARKKSGGAKQHFVDALLTLQEKYDLSDDTVIGLLWDMIT 143
Ptcgi_224139664       VEKHNARRDGLTRVIMEEHTNARKKSGGAKKHFVDALLTLQEKYDLSEVTITGLLWDMIT 299
                     . ** ****.***.**:***  **:.** **:*********::*****:  *: *******

EglC3Hgi_295413824    AGMDTTAISVEWAMAELIKNPRVQQKAQEELDRVVGFERVVTEPDFSNLPYLQCIAKEAL 359
Palxpgrgi_166209291   AGMDTTAISVEWAMAELIKNPRVQQKAQEELDSVVGLERVMTEADFSGLPYLLCVAKEAL 358
ColC3H                AGMDTTAIAAEWAMAELIKNPRVQQKAQEELDRVVGFERVMSETDFSSLPYLQSVTKEAF 203
Ptcgi_224139664       AGMDTTAITVEWAMAELIKNPRVQQKAQDELDRVVGFERVMTEADFPNLPYLQAVVKESL 359
                     ********:.*****************:***.****:***:.*.**..****  .::**::

EglC3Hgi_295413824    RLHPPTPLMLPHRSNSHVKIGGYDIPKGSNVHVNVWAIARDPAVWNSPLEFRPERFLEED 419
Palxpgrgi_166209291   RLHPPTPLMLPHRANANVKIGGYDIPKGSNVHVNVWAVARDPAAWKNPLEFRPERFLEED 418
ColC3H                RMHPPTPLMLPHKANANVKIGGYDIPKGSNVHVNVWAVANDPAVWKDPEVFRPERFLEED 263
Ptcgi_224139664       RLHPPTPLMLPHRANTTVKIGGYDIPKGSVVHVNVWAVARDPALWKNPLEFRPERFFEED 419
                     *:**********::*:.*. :**********.******:*.:*** :*  :********:***

EglC3Hgi_295413824    VDMKGHDFRLLPFGAGRRVCPGAQLGINLVTSMLGHLLHHFVWTPPQGTKPEEIDMSENP 479
Palxpgrgi_166209291   VDMKGHDFRLLPFGAGRRVCPGAQLGINLVTSMLGHLLHHFVWTPPEGVKAEEIDMSENP 478
ColC3H                VDMKGHDYRLLPFGAGRRVCPGAQLGINLVTSMLGHLLHHFCWTPPEGVKPEEIDMAENP 323
Ptcgi_224139664       VDMRGHDFRLLPFGAGRRVCPGAQLGINLVTSIIGHLLHHFHWTTPDGVKPEEIDMSERP 479
                     ***:***:************************..****** ** *:*.* ****:*.*

EglC3Hgi_295413824    GLVTYMSTPVQAVATPRLPSELYKRVPYEM 509(SEQ ID NO: 78)
Palxpgrgi_166209291   GLVTYMRTPLQAVATPRLPSHLYKRVAVDI 508(SEQ ID NO: 79)
ColC3H                GLVAYMKTPVQAVATPRLPSDLYKRVAVDI 353(SEQ ID NO: 34)
Ptcgi_224139664       GLVTYMMTPLQAVATPRLPSHLYKRMASDM 509(SEQ ID NO: 80)
                     ***:** **.********** ****:  ::
```

Figure 6

```
GarC4Hgi_9965897      MDLLFLEKALLGLFVAVVLAITISKLRGKRFKLPPGPLPVEVFGNWLQVGDDLNHRNLTD 60
GhiC4H2gi_268528127   MDLLFLEKALLGLFVAVVLAITISKLRGKRFKLPPGPLPVEVFGNWLQVGDDLNHRNLTD 60
ColC4H1               MDLLFLEKALIGLFVAVILAIAISKLRGKRYKLPPGPLPVEVFGNWLQVGDDLNHRNLTD 60
ColC4H2               MDLLFLEKALISLFVTIIVAIVVSKLRGKRYKLPPGPIPVEVFGNWLQVGDDLNHRNLTD 60
                      *********:.***:::.*:.:*****:***** ***.*.**********

GarC4Hgi_9965897      LAKKFGDIFLLRMGQRNLVVVSSPELAKEVLHTQGVEFGSRTRNVVFDIFTKGKQDMVFT 120
GhiC4H2gi_268528127   LAKKFGDIFLLRMGQRNLVVVSSPELAKEVLHTQGVEFGSRTRNVVFGIFTKGKQDMVFT 120
ColC4H1               LAKKYGDIFLLRMGQRNLVVVSSPELAKEVLHTQGVEFGSRTPNVVFDIFTKGKQDMVFT 120
ColC4H2               LAKKFGDIFLLRMGQRNLVVVSSPELAKEVLHTQGVEFGSRTPNVVFDIFTKGKQDMVFT 120
                      ****:******************************.*********

GarC4Hgi_9965897      VYGEHWRKMRRIMTVPFFTNKVVQQYRFGWEDEAARVVEDVRKNPEAATNGIVLRRRLQL 180
GhiC4H2gi_268528127   VYGEHWRKMRRIMTVPFFTNKVVQQYRFGWEDEAARVVEDVRKNPEAATNGIVLRRRLQL 180
ColC4H1               VY------------------VVQQYRFGWEEEAARVVEDVRKNPEAATNGIVLRRRLQL 161
ColC4H2               VYGEHWRKMRRIMTVPFFTNKVVQQYREGWEAEVAAVVEDVKKNPESATTGIVLRKRLQL 180
                      **                  ******.*** *.* *****:****:**:**.******

GarC4Hgi_9965897      MMYNNMYRIMFDTRFESEDDPLFVRLKALNGERSRLAQSFEYNYGDFIPILRPFLRGYLK 240
GhiC4H2gi_268528127   MMYNNMYRIMFDTRFESEDDPLFVRLKALNGERSRLAQSFEYNYGDFIPILRPFLRGYLK 240
ColC4H1               MMYNNMYRIMFDRRFESEEDPLFVKLKALNGERSRLAQSFEYNYGDFIPILRPFLRGYLK 221
ColC4H2               MMYNNMYRIMFDRRFESEDDPLFVKLKALNGERSRLAQSFDYNYGDFIPILRPFLRGYLK 240
                      ************ *****:******:**************.*******************

GarC4Hgi_9965897      ICKEVKDRRLQLFKDHFVEERKKLGSTKSMNNDGLKCAIDHILDAQQKGEINEDNVLYIV 300
GhiC4H2gi_268528127   ICKEVKDRRLQLFKDHFVEERKKLGSTKSMNNDGLKCAIDHILDAQQKGEINEDNVLYIV 300
ColC4H1               ICKEVKERRLQLFKDYFVEERKKLASTKSMSNEGLKCAIDHILDAQQKGEINEDNVLYIV 281
ColC4H2               LCKEVKEMRLQLFRDHFLEERKKLSSTKRPDNNALKCAIDHILDAQQKGEINEDNVLYIV 300
                      :*****: *****:*:*:******.***.  * :.************************

GarC4Hgi_9965897      ENINVAAIETTLWSIEWGIAELVNHPEIQKKLRHELDTVLGPGNQITEPDTEKLPYLQAV 360
GhiC4H2gi_268528127   ENINVAAIETTLWSIEWGIAELVNHPETQKKLRHELDTVLGPGNQITEPDTEKLPYLQAV 360
ColC4H1               ENINVAAIETTLWSIEWGIAELVNHPEIQKKLRDELDTLLGPGHQITEPDTYKLPYLQAV 341
ColC4H2               ENINVAAIETTLWSIEWGIAELVNHPEIQQKLRNEIDTVLGPGVQVTEPDTEKLPYLQAV 360
                      *************************** *:*** *:**:**** *:***** *******

GarC4Hgi_9965897      IKETLRLRMAIPLLVPHMNLHDAKLGGYDIPAESKILVNAWWLANNPANWKNPEEFRPER 420
GhiC4H2gi_268528127   IKETLRLRMAIPLLVPHMNLHDAKLGGYDIPAESKILVNAWWLANNPANWKNPEEFRPER 420
ColC4H1               IKETLRLRMAIPLLVPHMNLHDAKLAGYDIPAESKILVNAWWLANNPAQWKNPQEFRPER 401
ColC4H2               IKETLRLRMAIPLLVPHMNLHDAKLGGYDIPAESKILVNAWWLANNPAQWKNPEEFRPER 420
                      *************************.***************************.*****

GarC4Hgi_9965897      FFEEEAKVEANGNDFRYLPFGVGRRSCPGIILALPILGITLGRLVQNFELLPPPGCSQID 480
GhiC4H2gi_268528127   FFEEEAKVEANGNDFRYLPFGVGRRSCPGIILALPILGITLGRLVQNFELLPPPGCSQID 480
ColC4H1               FFEEESKVEANGNDFRYLPFGVGRRSCPGIILALPILGITLGRLVQNFELLPPPGCSKID 461
ColC4H2               FFEEEAKVEANGNDFRYLPFGVGRRSCPGIILALPILGITLGRLVQNFELLPPPGCSKLD 480
                      *****:************************************************:*

GarC4Hgi_9965897      TTEKGGQFSLHILKHSTIVAKPRQF 505(SEQ ID NO: 81)
GhiC4H2gi_268528127   TTEKGGQFSLHILKHSTIVAKPRQF 505(SEQ ID NO: 82)
ColC4H1               TSEKGGQFSLHILKHSTIVL----- 481(SEQ ID NO: 36)
ColC4H2               TSEKGGQFSLHILKHSTIVAKPRVF 505(SEQ ID NO: 38)
                      *:******************
```

Figure 7

```
ColPAL2          ---------------------------------------------------------
PtcPALgi_183585195  MEFCQDSRNGNGSLC--FNTNDPLNWGMAARSLKGSHLDEVKRMTEFYRKPVVKLGGETL  58
ColPAL1          ---------------------------------------------------------
JcoPALgi_113203757  MATIIGNGHQNGSLEGLCITRDPLSWGVAAESMKGSHLDEVKKMVSEYRKPLVKLGGETL  60

ColPAL2          ----------------MLEFSAKALS----------------------------------  10
PtcPALgi_183585195  TIGQVTAIASRDVGVMVELSEEARAGVKASSDWVMDSMSKGTDSYGVTTGFGATSHRRTK  118
ColPAL1          ---------------------------------------------------------
JcoPALgi_113203757  TVAQVAAIASHDAGVKVELAESARAGVKASSDWVMDSMNKGTDSYGVTTGFGATSHRRTK  120

ColPAL2          -------------------------RAHTLPHTATRAAMLVRINTLLQGYSGIRFEILEAIT  47
PtcPALgi_183585195  QGGELQKELIRFLNAGIFGNGTESSHTLPRSATRAAMLVRINTLLQGYSGIRFDMLEAIT  178
ColPAL1          ----------------------------MLVRINTLLQGYSGIRFEILEAIT  24
JcoPALgi_113203757  QGAALQRELIRFLNAGIFGNGTETCHTLPHSATRAAMLVRINTLLQGYSGIRFEILEAIT  180
                                             *****************:****

ColPAL2          KFLNVNITPCVPLRGSITASGDLVPLSYIAGLLTGRPNSKALGPNGEAMNPTEAFSRAGI  107
PtcPALgi_183585195  KLLNHNITPCLPLRCTITASGDLVPLSYIAGLLTGRPNSKAVGPNGEPLSPAEAFTQAGI  238
ColPAL1          KFLNQNITPCLPLRGTIASGDLVPLSYIAGLLTGRPNSKAVGPNGESLNAEEAFNRAGI  84
JcoPALgi_113203757  KLLNHNITPCLPLPGTITASGDLVPLSYIAGLLTGRPNSKAIGPSGESLDAVEAFRLADI  240
                   *:**  *****:****:.**********************::**  **   ***  * *

ColPAL2          HGGFFELQPKEGLALVNGTAVGSGLASLVLYEANVLAVLSEVLSAIFAEVMQGKPEFTDH  167
PtcPALgi_183585195  DGGFFELQPKEGLALVNGTAVGSGLASMVLFETNVLAILSEVLSAIFAEVMQGKPEFTDH  298
ColPAL1          ESGFFTLQPKEGLALVNGTAVGSGMASMVLFEANILAVLSEVLSAIFAEVMNGKPEFTDH  144
JcoPALgi_113203757  DSGFFRLQPKEGLALVNGTAVGSGIASMVLFEANVLAVLSELLSAIFAEVMMGKPEFTDH  300
                   .:***.******************:**:***:.**.**:*:************:******

ColPAL2          LTHKLKHHPGQIEAAAIMEHILDGSSYIKAAQKLHEMDPLQKPKQDRYALRTSPQWLGPQ  227
PtcPALgi_183585195  LTHKLKHHPGQIEAAAIMEHILDGSSYVKEAQKLHEIDPLQKPKQDRYALRTSPQWLGPL  358
ColPAL1          LTHKLKHHPGQIEAAAIMEHILDGSGYVKAAKKLHEMDPLQKPKQDRYALRTSPQWLGPQ  204
JcoPALgi_113203757  LTHKLKHHPGQIEAAAIMEHILDGSSYIKAAKQLHEIDPLQKPKQDRYALRTSPQWLGPQ  360
                   *************************.*:* *::***:**********************

ColPAL2          IEVIRSATKMIEREINSVNDNPLIDVSRDKALHGGNFQGTPIGVSMDNTRLAIAAIGKLM  287
PtcPALgi_183585195  IEVIRTSTKMIEREINSVNDNPLIDVSRNKALHGGNFQGTPIGVSMDNTRLAIASIGKLM  418
ColPAL1          IEVIRFATKSIEREINSVNDNPLIDVSRNKALHGGNFQGTPIGVSMDNARLAIASIGKLM  264
JcoPALgi_113203757  IEVIRFSTKSIEREINSVNDNPLIDVSRNKALHGGNFQGTPIGVSMDNARLAIASIGKLM  420
                   *****  :**  *****************:*****************:*****:*****

ColPAL2          FAQFSELVNDYYNNGLPSNLSASRNPSLDYGFKGAEIAMASYCSELQFLGNPVTNHVQSA  347
PtcPALgi_183585195  FAQFSELVNDFYNNGLPSNLTGGRNPSLDYGFKGAEIAMASYCSELQFLANPVTNHVQSA  478
ColPAL1          FAQFSELVNDFYNNGLPSNLSGGRNPSLDYGFKGAEIAMASYCSELQFLANPVTNHVQSA  324
JcoPALgi_113203757  FAQFSELVNDFYNNGLPSNLSGGRNPSLDYGFKGAEIAMASYCSELQFLANPVTSHVQSA  480
                   **********:*********:..*************************.****:*****

ColPAL2          EQHNQDVNSLGLISARKTAEAIDILKLMSSTFLIALCQAIDLRHLEENLKNTVKNTVSQI  407
PtcPALgi_183585195  EQHNQDVNSLGLISSRKTAEAVDILKLMSTTFLVGLCQAVDLRHIEENLKSTVKNTVSQV  538
ColPAL1          EQHNQDVNSLGLISARKTSEAVDILKLMSSTYLVALCQAIDLRHLEENLRNTVKNTVSQI  384
JcoPALgi_113203757  EQHNQDVNSLGLISSRKTQEAIDILKLMSSTFLVALCQAIDLRHLEENLKHAVKNTVTQV  540
                   **************:***.**:*******:*:*:.****:****:****:.:****:*:

ColPAL2          AKRVLTMGSNGELHPSRFCEKDLLRVVDREHLYAYIDDPCSASYPLMQKLRQVLVDHALM  467
PtcPALgi_183585195  AKRVLTMGFNGELHPSRFCEKDLLKVVDREHVPSYIDDPCSATYPLMQKLRQVLVEHAIT  596
ColPAL1          AKKVLTTGANGELHPSRFCEKDLLKAVDREYVFAYIDDPCSATYPLMQKLRQVLVEHALT  444
JcoPALgi_113203757  AKRVLTTGANGELHPSRFCGKDLLKVVDREQVFAYIDDPCSATYPLMQKLRQVLVEHALA  600
                   **:***  .**********  ****.:****  ::*******:***********:.:

ColPAL2          NGDNEKNSTTSIFQKIGAFEEELKTLLPKEVESARIEFENGN-AAIPNRIKECRSYPLYK  526
PtcPALgi_183585195  NGERERNSTTSIFQKIGSFEEELKTLLPKEVESARLEVENGN-PAIFNRIKECRSYPLYK  657
ColPAL1          NGESEKNASTSIFQKIAAFEEELKTLLPKEVESARVALENGSNVAVPNRIKECRSYPLYK  504
JcoPALgi_113203757  NGENEKNASTSVFQKIGAFEEELKTLLPKEVESAREAYESGS-AAIGNKIKECRSYPLYK  659
                   **  *:*::**:****::************************   *    *:******

ColPAL2          FVREVLGTSLLTGEKVTSPGEECDKVFSAICAGKLIDPLFQCLKEWNGAPLPTC  580 (SEQ ID NO: 43)
PtcPALgi_183585195  FVREELGTSLLTGEKVKSPGEEFDKVFTAICAGKLIDPLLECLKEWDGAPLPIC  711 (SEQ ID NO: 83)
ColPAL1          FVREELGTGLLLTGEKVRSPGEEFDKVFTAMCQGKLIDPMLECLKEWDGAPLPIC  558 (SEQ ID NO: 41)
JcoPALgi_113203757  FVREELGSGLLLTGEKVRSPGEEFDKVFTAMCEGKIIDPMMECLKEWNGAPLPIC  713 (SEQ ID NO: 84)
                   ****  **.*******  *****:***:*:*  **:***::*****:******
```

Figure 8

```
AthCCRgi_15237678      MLTD------EREVVCVTGASGCIGSWLVHQLLLRGYSVHATVKNLQDEKETKHLEGLEG  54
AlyCCRgi_297793385     -MST------EREVVCVTGASGCIGSWLVHLLLHRGYSVHATVKNLQDEKETKHLEALEG  53
ColCCR2                -MSK------QGEAVCVTGASGAIGSWLVKLLLARGYTVHGTVRNIKDEKETKHLESLEG  53
CofCCRgi_228480464     -MSSNTKAGGDGQVVCVTGGSGFIGSWLVRLLLDRGYTVHATVKDLKDEKETKHLEALEG  59
                        ::       : :.*****.** ******:  ** ***:**.**:::******** ***

AthCCRgi_15237678      AATRLHLFEMDLLQYDTVSAATNGCSGVFHLASPCIVDEVQDPQKQLLDPAVKGTINVLT 114
AlyCCRgi_297793385     AATRLHLFEMDLLQYDTVSAAVNGCSGVFHLASPCIVDEVQDPQKQLLDPAVKGTINVLT 113
ColCCR2                AESRLRLFQIDLLDYDAISAAIEGCAGVFHLASPCTVDQVHDPQKELLDPAIKGTLNVLT 113
CofCCRgi_228480464     AESRLRLFQIDLLDYDSIVAAVTGSSGVFHLASPCIVDQVKDPEREILEPAIKGTLNVLT 119
                       *.:**:**::***:**:: **. *.:********* **:*:**::: **:**:***:****

AthCCRgi_15237678      AAKEASVKRVVVTSSISAITPSPNWPADKIKNEECWAAEDYCRQNGLWYPLSKTLAEKAA 174
AlyCCRgi_297793385     AAKEAGVKRVVVTSSISAITPSPNWPADKIKNEECWADQDYCKQNGLWYPLSKTLAEKAA 173
ColCCR2                AAKELGVKRVVVTSSVSSITPSPNWPADKIKTEDCWTDIDYCKQNELWYPISKTLAEKAA 173
CofCCRgi_228480464     AAKELGVRRVVVTSSNTAITPSPNWPADKVKNEDCWTDVEYCKQNGLWYPLSKTLAEKAA 179
                       ****  *::*******  :*********:*.*:***:  :**:**.****:*********

AthCCRgi_15237678      WEFASEKGLDVVVVNPGTVMGPVIPPSLNASMHMLLRLLQGCTETYENFFMGSVEFKDVA 234
AlyCCRgi_297793385     WEFASQKGLDVVVVNPGTVMGPVIPPSINASMLMLLRLLQGCTETYENFFMGSVEFKDVA 233
ColCCR2                WEFSKEKGLDVVVVNPGTVMGPNIPPTLTASMWMLLRLLQGCTETYQDFFMGSVEFKDVA 233
CofCCRgi_228480464     WEFAKEKGLDVVVVNPGTVMGPIIPPALNASMLMLLRFLQCCTEIYENFFMGPVEVKDVA 239
                       ***: :***************  ***::.****  ****:**.***:*: ****.** ****

AthCCRgi_15237678      LAHILVYEDPYSKGRHLCVEAISHYGDFVAKVAELYPNYNVPKLPRETQPGLLRDKNASK 294
AlyCCRgi_297793385     LAHILVYENPSAKGRHLCVEAISHYGDFVAKVAELYPNYSVPKLPRETQLGLLRAKNAAK 293
ColCCR2                LAHILVYENPSASGRHMCLEAISHYGDFVAKVAELYPEYNVPSLPRDTQPGLLRAKNGGQ 293
CofCCRgi_228480464     LAHILVYENTSATGRHLCVEAISHYGDFTAMVAELYPEYNVPRLPKDTQPGLLRTKDGSK 299
                       ********: .:.:***:*:********.* *.*****:*.** **:.** ****.*:..:

AthCCRgi_15237678      KLIDLGLKFISMEEIIKEGVESLKSKGFIS 324 (SEQ ID NO: 85)
AlyCCRgi_297793385     KLMELGLEFSSMEDIIKEGVESLKSKGFIS 323 (SEQ ID NO: 86)
ColCCR2                KLMDLGLEFIPMEQIIKDAVESLKSKGLI- 322 (SEQ ID NO: 46)
CofCCRgi_228480464     KLMDLGFQFIPMEQIIKETVESLKSKGYIS 329 (SEQ ID NO: 87)
                       **:::**::* .***:**: ******** *
```

Figure 9

```
CLUSTAL 2.1 multiple sequence alignments

ColCCR3                  ------------------------------------------------------------
RcoCCRgi_255556687       MATQNKKEAVCVTGANGFIGSWLIQTLLQHGYTTIHASIYPASDPSHLFHLISSSSHGDI  60
AthCCRgi_15226955        ----MAKETVCVTGANGFIGSWIIRTLIEKGYTKIHASIYPGSDPTHLLQLPGSDSK---  53

ColCCR3                  ------------------------------------------------------------
RcoCCRgi_255556687       INLKLYEADLLDYDAICKAVEGCQGVFHVASPCTLEEPKDPEKELVLPAVQGTINVLEAA 120
AthCCRgi_15226955        --IKIFEADLLDSDAISRAIDGCAGVFHVASPCTLDPPVDPEKELVEPAVKGTINVLEAA 111

ColCCR3                  ---------------AIVPNPNWNPQTNGAFDETSWTDLEYCKSRQKWYPVSKTMAEKTA  45
RcoCCRgi_255556687       RKFKVRRVVLTSSISALVPNPNWP--AGKVFDESSWTDLDYCKSRQKWYPVSKSLAEKAA 178
AthCCRgi_15226955        KRFNVRRVVITSSISALVPNPNWP--EKVPVDESSWSDLDFCKSRQKWYPISKTLAEKAA 169
                                        *:******     .**:**:**:**********:**:;***:*

ColCCR3                  WEFAEKHGMDVVAINPATCIGPLLQPNLNASCAVLLQLLEGSKDTQEYHWLGAVHVKDVA 105
RcoCCRgi_255556687       WEFAEKHGMDVVAIHPSTCIGPLLQPSLNASSAVLQQLLEGSKDTQEYHWLGAVHVKDVA 238
AthCCRgi_15226955        WEFSEKHGTNIVTIHPSTCIGPLLQPNLNASCAVLLQLLQGSTETQEHHWLGVVHVKDVA 229
                         ***;****  ;:*;*;*;**;******.****.*** ***;**.;***;****.******

ColCCR3                  KAQILLFESPSASGRYLCTNGIYQFGTFAETVSHLFPQYPVHRFTGDTQPGLVSCKDAAK 165
RcoCCRgi_255556687       KAQVLLFEAPSASGRYLCTNGIYQFGDFADRVSKLFPEFPVHSFIGETQPGLTTCKDAAK 298
AthCCRgi_15226955        KGHVMLFETPDASGRFLCTNGIYQFSEFAALVSKLFPEFAVHKFDKETQPGLTSCNDAAK 289
                         *.::;***:*.****:********. ** **:***::.**  *  :*****.:*:****

ColCCR3                  RLIELGLIFTPVEEAVRETVESLQAKGFLKQQQPSFS 202(SEQ ID NO: 48)
RcoCCRgi_255556687       RLIELGLVFTPVEDAVGESVESLQAKGFLKHKT-SES 334(SEQ ID NO: 88)
AthCCRgi_15226955        RLIELGLVFTAVEDAVKETVQSLRDKGFL-------- 318(SEQ ID NO: 89)
                         *******:**.**:** *:*:**:.****
```

Figure 10

```
CLUSTAL 2.1 multiple sequence alignments

EgoF5Hgi_255970299      MDIFYFYSQLQSLVQTQLQQSPMTLLLSVVPLLLFLGLVARLRRKPPPPPGPRGLPVIGN  60
ColF5H                  ----------------------MALLFIVPFLLLLGLVSRLRRKP-PPPGPKGLPIIGN  36
PtcF5Hgi_6688937        ------------------------------------------------------------

EgoF5Hgi_255970299      MLMMGELTHRGLASLAKKYGGIFHLRMGFLHMVAVSSPDVARQVLQVHDGIFSNRPATIA 120
ColF5H                  MMMMDQLTHRGLAKLANKYGGIFHMKMGYLHMVAVSNPDMARQVLQVQDNIFSNRPATIA  96
PtcF5Hgi_6688937        --------------------GLFHMRMGYLHMVAGSSPEVARQVLQVQDNMFSNRPANIA  40

EgoF5Hgi_255970299      ISYLTYDRADMAFAHYGPFWRQMRKLCVMKLFSRKRAESWESVRDEVDIMVRTVAGSEGT 180
ColF5H                  ISYLTYDRADMAFAHYGPFWRQMRKLCVMKLFSRKRAESWESVRDEVDSMVRTVSANTGK 156
PtcF5Hgi_6688937        ISYLTYDRADMAFAHYGPFWRQMRKLCVMKLFSRKRAESWESVRDEVDSMVKTVESNIGK 100
                        *****************************************************:**:**  .. *.

EgoF5Hgi_255970299      AVNIGELVFELTRDIIYRAAFGTSSTEGQDEFISILQEFSKLFGAFNIADFIPYLSWIDP 240
ColF5H                  SINVGELIFNLTKNIIYRAAFGSSSQEGQDEFIGILQEFSKLFGAFNIADFIPWLTWVDP 216
PtcF5Hgi_6688937        PVNVGELIFTLTMNITYRAAFG-AKNEGQDEFIKILQEFSKLFGAFNISDFIPWLGWIDP 159
                        .:*:***:* ** :* ******  :.  ******* ************.***:* *:**

EgoF5Hgi_255970299      QGLTARLVKARQSLDGFIDHIIDDHMDKKRNKTSSGGGDQEVDTDMVDDLLAFYSDEAKV 300
ColF5H                  QGLNNRLKNARQALDKFIDTIIDEHIQKRNNKNNVS---DDVDTDMVDDLLAFYSEEAKV 273
PtcF5Hgi_6688937        QGLTARLVKARKALDKFIDHIIDDHIQKRK-QNNYS---EEAETDMVDDMLTFYSEETKV 235
                        ***. ** :**::** *** ***:*::*:.  :..    ::.:******* :***:*:**

EgoF5Hgi_255970299      NESDDLQNSIRLTRDNIKAIIMDVMFGGTETVASAIEWAMAELMRSPEDLKKVQQELADV 360
ColF5H                  NESEDLQNAIRLTRENIKAIIMDVMFGGTETVASAIEWALSELMRSPEDMKRVQQELADV 333
PtcF5Hgi_6688937        NESDDLQNAIKLTRDNIKAIIMDVMFGGTETVASAIEWAMAELLKSPEDIKRVQQELADV 275
                        ***.****:*:***:*********************:  **.:****:*:********

EgoF5Hgi_255970299      VGLDRRVEESDFEKLTYLKCCLKETLRLHPPIPLLLHETAEDAVISGYRIPARSRVMINA 420
ColF5H                  VGLDRKVEESDFDKLTFLKCTLKETLRLHPPIPLLLHETAEDAEVGGYRIPAKS------ 387
PtcF5Hgi_6688937        VGLERRVEESDFDKLTFFKCTLKETLRLHPPIPLLLHETSEDAEVAGYYVPKKTRVMINA 335
                        ***:*:******:***::** ***************** :***  :.**  :*  :  ::

EgoF5Hgi_255970299      WAIGRDPGSWTEPDKFKPSRFLESCMPDYKGSNFEFIPFGSGRRSCPGMQLCLYALDMAV 480
ColF5H                  ------------------------------------------------------------
PtcF5Hgi_6688937        YAIGRDKNSWEDPDSFKPSRFLEPGVPDFKGNHFEFIPFGSGRRSCPGMQLGLYALDLAV 395

EgoF5Hgi_255970299      AHLLHCFTWELPDGMKPSEMDMGDVFGLTAPRSTRLVAVPTPRLVGALY 529 (SEQ ID NO: 90)
ColF5H                  --------------------------------------------(SEQ ID NO: 50)
PtcF5Hgi_6688937        AHLLHCFTWELPDGMKPSELDMTDMFGLTAPRATRLVAVPRKRVVCPL- 443 (SEQ ID NO: 91)
```

Figure 11

```
CLUSTAL 2.1 multiple sequence alignments

ColCOMT              MGSTG-ETQFTFTQVSDEEANLFAMQLASASVLPMVLKSAIELDLLEVMAKAGPGAFLSP  59
GhiCOMTgi_253509569  MGSTG-ETQMTPTQVSDEEANLFAMQLTSASVLPMVLKSAIELDLLEIMAKAGPGAFLSP  59
EcaCOMTgi_262474806  MGSTGSETQMTFTQVSDEEANLFAMQLASASVLPMVLKAAIELDLLEIMAKAGPGAFLSP  60
                     *****  ***: *.************* :******** *********:********

ColCOMT              TEVASQLPTKNPDAPVMLDRILRLLASYSILTCSLRNLPDGKVERLYGLGPVCKYLVKNE  119
GhiCOMTgi_253509569  KELASQLPTSNPDAPVMLDRILRLLATYSILTCSLRTLPDGKVERLYGLGPVCKFLTKNE  119
EcaCOMTgi_262474806  GEVAAQLPTQNPEAPVMLDRIFRLLASYSVLTCTLRDLPDGKVERLYGLAPVCKFLVKNE  120
                     :  *:****.** ********:****:**:*** **.*************.****:*.***

ColCOMT              DGVALSAINLMNQDKVLMESWYYLKDAVLEGGIPFNKAYGMTAFEYHGTDPRFNKVFNRG  179
GhiCOMTgi_253509569  DGVTLSALSLMNQDKVLMESWYYLKDAVLEGGIPFNKVYGMTAFEYHGTDPRFNKVFNRG  179
EcaCOMTgi_262474806  DCVSIAALNLMNQDKILMESWYYLKDAVLEGGIPFNKAYGMTAFEYHGTDPRFNKIFNRG  180
                     * *::.**.******::********************.***************:****

ColCOMT              MSDHSTITMKKILETYDGFEGLKTLVDVGGGVGATLNMIVSKHPSIKGINFDLPHVIEDA  239
GhiCOMTgi_253509569  MSDHSTITMKKILETYDGFEGLKTLVDVGGGTGATLNMIVTKHPSIKGINFDLPHVIEDA  239
EcaCOMTgi_262474806  MSDHSTITMKKILETYKGFEGLETVVDVGGGTGAVLSMIVAKYPSMKGINFDLPHVIEDA  240
                     ****************.***** *:****** **.*.*** *.**:************

ColCOMT              PALPGVEHVGGDMFVSVPKGDAIFMKWICHDWSDEHCVKFLKKCYEALPDNGKVIVAECI  299
GhiCOMTgi_253509569  PAYPGVEHVGGDMFESVPKGDAIFMKWICHDWSDEHCSKFLKKCYEALPDSGKVIVAECI  299
EcaCOMTgi_262474806  PPLPGVKHVGGDMFVSVPKGDAIFMKWICHDWSDDHCAKFLKNCYDALPNNGKVIVAECV  300
                     *. ***:*******.*******************::** *** **:***.:*******.

ColCOMT              LPDYPDASLATKLVVHIDCIMLAHNPGGKERTEKEFEALAKGAGFQGFQVKCCAFGTYIM  359
GhiCOMTgi_253509569  LPDYPDPSLATKLVVHIDCIMLAHNPGGKERTEKEFEALARSAGFQGFQVKCCAFGTYIM  359
EcaCOMTgi_262474806  LPVYPDTSLATKNVIHIDCIMLAHNPGGKERTQKEFETLAKGAGFQGFQVMCCAFGTHVM  360
                     ** ***.***** *:*****************:****:**:.******** ******::*

ColCOMT              EFLKIV 365(SEQ ID NO: 52)
GhiCOMTgi_253509569  EFVKRV 365(SEQ ID NO: 92)
EcaCOMTgi_262474806  EFLKIA 366(SEQ ID NO: 93)
                     **:*  .
```

Figure 12

POLYNUCLEOTIDES ENCODING ENZYMES FROM THE JUTE LIGNIN BIOSYNTHETIC PATHWAY

RELATED APPLICATIONS

This application is a 371 national stage application of PCT/US12/034980, filed Apr. 25, 2012, which claims the benefit of priority to U.S. Provisional Patent Application Ser. No. 61/480,668 filed Apr. 29, 2011. The entire contents of each of these applications are hereby incorporated by reference.

FIELD OF THE INVENTION

The invention relates to the identification and characterization of various portions of the jute lignin biosynthetic pathway. More specifically, the invention relates to polynucleotides from jute plants that encode enzymes responsible for lignin synthesis, and methods for using these polynucleotides and enzymes for gene regulation and manipulation of lignin production to give fibers with desired lignin content and other characteristics.

BACKGROUND OF THE INVENTION

Lignin is a collective name for a complex aromatic heteropolymer of monolignol (hydroxycinnamyl alcohols), usually derived from phenylalanine in a multistep process. (Whetten, R. and Sederoff, R., (1995) Lignin Biosynthesis, *Plant Cell,* 7, pp. 1001-1013). These polymers, deposited primarily in cell walls, ensure the necessary mechanical strength of plant stems and most importantly, the hydrophobicity of a plant's vascular tissues. (Vanholme, R. et al. (2010) Lignin biosynthesis and structure, *Plant Physiol,* 153, pp. 895-905). Due to its hydrophobic nature, lignin serves as a major component of the vascular tissues and plays an essential role in water transport. In addition to its structural and transport-oriented role, lignin is a key component of a plant's defense system. (Goujon, T. et al. (2003) Genes involved in the biosynthesis of lignin precursors in *Arabidopsis thaliana, Plant Physiology and Biochemistry,* 41, pp. 677-687). Not surprisingly, environmental conditions influence the amount of lignin deposited. (Boerjan, W. et al. (2003) Lignin biosynthesis, *Annu Rev Plant Biol,* 54, pp. 519-546). For example, lignin biosynthesis is induced in response to various stress conditions like wounding, abiotic stress, and pathogen infection. Lignin limits pathogen invasion and protects the cell wall polysaccharides against microbial degradation. (Vanholme et al., 2010).

A large part of our current understanding of lignin biosynthesis comes from the complete understanding of this pathway in *A. thaliana* and *P. trichocarpa.* (Goujon, et al., 2003; Shi, et al. (2010) Towards a systems approach for lignin biosynthesis in *Populus trichocarpa*: transcript abundance and specificity of the monolignol biosynthetic genes, *Plant Cell Physiol,* 51, pp. 144-163). There are three basic monolignol monomers: p-coumaryl, coniferyl, and sinapyl alcohols. These monolignols are incorporated into the three lignin units, or building blocks: p-hydroxyphenyl (H), guaiacyl (G), and syringyl (S). See FIG. 1. These monolignols differ in the number of methoxy groups. P-hydroxyphenyl (H) has no methoxy group, guaiacyl (G) has one methoxy group, and syringyl (S) has two methoxy groups. (Goujon et al., 2003). However, in addition to these three monolignols, a few other phenylpropanoids, such as hydroxycinnamyl aldehydes, hydroxycinnamyl esters, and hydroxycinnamyl acetates may also be incorporated. (Boerjan et al., 2003).

After the biosynthesis of these basic lignin building blocks, they are transported to lignifying zones. In the lignifying zones, polymerization occurs by oxidative free-radical-based coupling by peroxidases or laccases and a mesh-like structure is formed by cross-linking with cellulose and hemicellulose. (Boerjan et al., 2003; Vanholme, R. et al. (2008) Lignin engineering, *Curr Opin Plant Biol,* 11, pp. 278-285). Lignification occurs in different phases during the secondary thickening of the cell wall when the polysaccharide matrix formation is complete. Lignin deposition is influenced by the nature of the polysaccharide matrix. In the primary cell wall, it is found as spherical structures; whereas in the secondary cell wall, it forms lamellae. (Boerjan et al., 2003).

Notwithstanding the indispensable role of lignin in the life of a plant, it is a major limiting factor in the cost-effective/efficient use of plant material in the pulp and biofuel industries. Lignin also limits the use of biomass for fiber, chemical, and energy production. Removal of lignin is a very expensive process and these industries would benefit from access to biomass having less lignin, or a lignin that is easy to degrade. In the last few decades, some understanding of the lignin biosynthetic pathway has been achieved, although portions of the process are not fully understood.

Despite the importance of lignin synthesis to the overall welfare of the jute plant, as well as its impact on several aspects of fiber quality, at present there is no available information detailing lignin biosynthesis in jute. Therefore, a need exists to identify, isolate and utilize genes and enzymes from the jute plant that are involved in the biosynthesis of lignin. The present invention addresses this need.

SUMMARY OF THE INVENTION

One aspect of the invention is an isolated nucleic acid molecule having at least 90% sequence identity to a nucleic acid sequence selected from the group consisting of: SEQ ID NO: 1, 3, 5, 7, 9, 11, 13, 15, 16, 18, 20, 22, 24, 25, 26, 28, 29, 31, 33, 35, 37, 39, 40, 42, 44, 45, 47, 49, and 51.

In one embodiment, an isolated nucleic acid molecule is selected from the group consisting of: SEQ ID NO: 1, 3, 5, 7, 9, 11, 13, and 15.

In one embodiment, an isolated nucleic acid molecule is selected from the group consisting of: SEQ ID NO: 16, 18, and 20.

In one embodiment, an isolated nucleic acid molecule is selected from the group consisting of: SEQ ID NO: 22, 24, 25, 26, 28, and 29.

In one embodiment, an isolated nucleic acid molecule is selected from the group consisting of: SEQ ID NO: 31.

In one embodiment, an isolated nucleic acid molecule is selected from the group consisting of: SEQ ID NO: 33.

In one embodiment, an isolated nucleic acid molecule is selected from the group consisting of: SEQ ID NO: 35, 37 and 39.

In one embodiment, an isolated nucleic acid molecule is selected from the group consisting of: SEQ ID NO: 40 and 42.

In one embodiment, an isolated nucleic acid molecule is selected from the group consisting of: SEQ ID NO: 44, 45, and 47.

In one embodiment, an isolated nucleic acid molecule is selected from the group consisting of: SEQ ID NO: 49.

In one embodiment, an isolated nucleic acid molecule is selected from the group consisting of: SEQ ID NO: 51.

One aspect of the invention is an isolated polypeptide molecule having at least 90% sequence identity to an amino acid sequence selected from the group consisting of SEQ ID NO: 2, 4, 6, 8, 10, 12, 14, 17, 19, 21, 23, 27, 30, 32, 34, 36, 38, 41, 43, 46, 48, 50, and 52.

In one embodiment, a pair of forward and reverse primers useful for the amplification of cDNA selected from the group consisting of SEQ ID NO 53 and SEQ ID NO 54; SEQ ID NO 55 and SEQ ID NO 56; SEQ ID NO 57 and SEQ ID NO 58; SEQ ID NO 59 and SEQ ID NO 60; and SEQ ID NO 61 and SEQ ID NO 62.

In certain embodiments, the present invention relates to any one of the aforementioned polynucleotide sequences or polypeptide sequences, wherein said sequence has at least 91%, 92%, 93%, 94%, 95%, 96%, 97%, 98%, 99%, or 100% sequence identity to any of the sequences identified by a SEQ ID NO.

One aspect of the invention is an expression vector comprising an isolated nucleic acid molecule of the present invention.

One aspect of the invention is an isolated antibody or antigen binding fragment thereof that specifically binds to a polypeptide molecule of the present invention.

One aspect of the invention is a transfected plant cell transfected by a vector of the present invention.

One aspect of the invention is a material derived from a transgenic plant of the present invention.

One aspect of the invention is a seed from a plant transfected by a vector of the present invention.

One aspect of the invention is a method for making a transgenic plant, comprising the steps of transfecting at least one plant cell with a vector of the present invention, and growing at least one plant cell into a plant.

One aspect of the invention is a method of improving growth, fiber yield, fiber strength, disease resistance, or water utilization in a jute plant, comprising incorporating in to a jute plant a non-native nucleic acid sequence of the present invention.

BRIEF DESCRIPTION OF THE DRAWINGS

FIGS. 2a and 2b: Protein sequence alignment of ColCAD1, ColCAD2, ColCAD3, ColCAD4, ColCAD5, ColCAD6, and ColCAD7 with plant CAD protein sequences. FIGS. 2a and 2b disclose SEQ ID NOS 2, 4, 63-64, 6, 65, 10, 66, 12, 67, 14, 68, 8 and 69, respectively, in order of appearance.

FIG. 3: Protein sequence alignment of ColCCoAOMT1, ColCCoAOMT2 and ColCCoAOMT3 with plant CCoAOMT protein sequences. FIG. 3 discloses SEQ ID NOS 19, 70-71, 17, 21 and 72, respectively, in order of appearance.

FIG. 4: Protein sequence alignment of Col4CL1, Col4CL4 and Col4CL6 with plant 4CL protein sequences. FIG. 4 discloses SEQ ID NOS 23, 73, 27, 74, 30 and 75, respectively, in order of appearance.

FIG. 5: Protein sequence alignment of Col6HCT1 with plant 6HCT protein sequences. FIG. 5 discloses SEQ ID NOS 32 and 76-77, respectively, in order of appearance.

FIG. 6: Protein sequence alignment of ColC3H with plant C3H protein sequences. FIG. 6 discloses SEQ ID NOS 78-79, 34 and 80, respectively, in order of appearance.

FIG. 7: Protein sequence alignment of ColC4H1 and ColC4H2 with plant C4H protein sequences. FIG. 7 discloses SEQ ID NOS 81-82, 36 and 38, respectively, in order of appearance.

FIG. 8: Protein sequence alignment of ColPAL1 and ColPAL2 with plant PAL protein sequences. FIG. 8 discloses SEQ ID NOS 43, 83, 41 and 84, respectively, in order of appearance.

FIG. 9: Protein sequence alignment of ColCCR2 with plant CCR protein sequences. FIG. 9 discloses SEQ ID NOS 85-86, 46, and 87, respectively, in order of appearance.

FIG. 10: Protein sequence alignment of ColCCR3 with plant CCR protein sequences. FIG. 10 discloses SEQ ID NOS 48 and 88-89, respectively, in order of appearance.

FIG. 11: Protein sequence alignment of ColF5H with plant F5H protein sequences. FIG. 11 discloses SEQ ID NOS 90, 50 and 91, respectively, in order of appearance.

FIG. 12: Protein sequence alignment of ColCOMT with plant COMT protein sequences. FIG. 12 discloses SEQ ID NOS 52 and 92-93, respectively, in order of appearance.

DETAILED DESCRIPTION OF THE INVENTION

Figure 1:
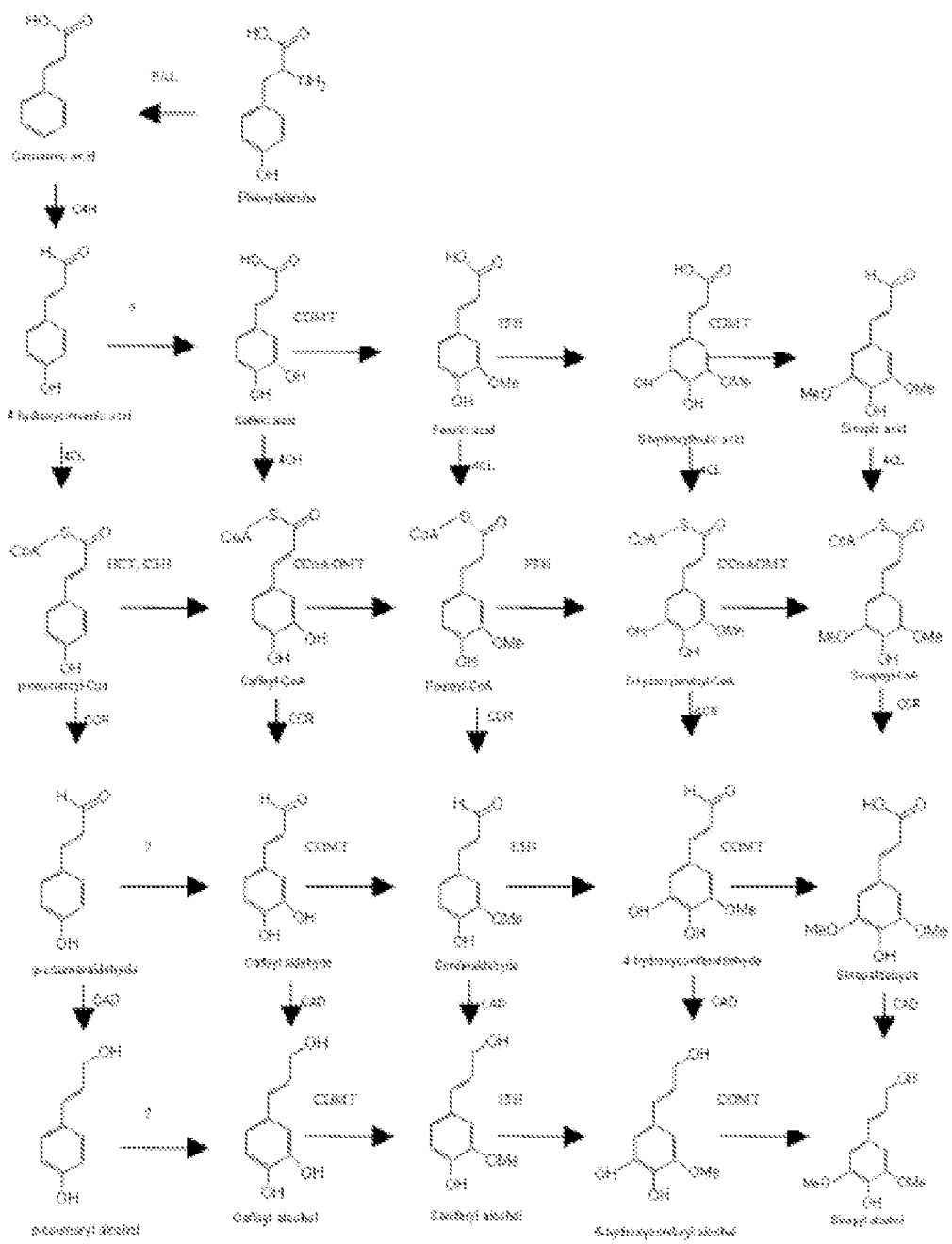
FIG. 1: Proposed monolignol biosynthesis pathway of jute.

Ten known enzyme families are associated with monolignol biosynthesis. (Goujon et al., 2003). The families are PAL (phenylalanine ammonia-lyase), C4H (cinnamate-4-hydroxylase), 4CL (4-coumarate:CoA ligase), HCT (p-hydroxycinnamoyl-CoA:shikimate/quinate p-hydroxycinnamoyl transferase), C3H (4-coumarate 3-hydroxylase), CCoAOMT (caffeoyl-CoA O-methyltransferase), CCR (cinnamoyl-CoA reductase), F5H (ferulate 5-hydroxylase), COMT (caffeic acid O-methyltransferase), and CAD (cinnamyl alcohol dehydrogenase). A proposed schematic of the monolignol biosynthetic pathway in Jute is shown in FIG. 1.

The lignin biosynthesis pathway in jute owes its complexity, in part, to the presence of several multifunctional enzymes, and to the constituent enzymes spanning several diverse gene families. The first enzyme of the phenylpropanoid pathway is PAL (phenylalanine ammonia-lyase), which causes the deamination of phenylalanine, producing cinnamic acid. The second enzyme of the pathway, C4H (cinnamate 4-hydroxylase), converts cinnamic acid to 4-hydroxycinnamic acid, which is followed by subsequent hydroxylation and methylation steps as the pathway becomes branched. The enzyme 4CL catalyzes the CoA ligation of hydroxycinnamic acids, generating activated phenolic precursors for lignin biosynthesis. (Hu et al. (1999) Repression of lignin biosynthesis promotes cellulose accumulation and growth in transgenic trees, *Nat Biotech*, 17, pp. 808-812.).

The next enzyme in the monolignol pathway (HCT) catalyses the production of p-coumaroyl-shikimate/quinate esters, which are the substrates for C3H. HCT was shown to transfer the acyl group of p-coumaroyl-CoA to shikimate or quinate. (Hoffman et al. (2005) *Plant Biosystems*, v. 139, No.

1, pp. 50-53). The hydroxylation steps at C3 and C5 are performed by two cytochrome P450 enzymes, 4-coumarate 3-hydroxylase (C3H) and ferulate 5-hydroxylase (F5H), respectively. The methylation steps are performed by CCoAOMT (caffeoyl-coenzyme A (CoA) O-methyltransferase) and COMT (caffeic-O-methyltransferase). CCoAOMT is a bifunctional enzyme which converts caffeoyl-CoA to feruloyl-CoA and 5-hydroxyferuloyl-CoA to sinapoyl-CoA and plays a role in the synthesis of feruloylated polysaccharides. (Inoue et al., 1998). CCoAOMT has been shown to be involved in lignin biosynthesis in the differential tracheary elements of *Zinnia elegans*. (Ye, Z. H. and Varner J. E. (1995) Differential expression of two O-methyltransferases in lignin biosynthesis in *Zinnia elegans, Plant Physiol.* 108, pp. 459-467). CCoAOMT is involved in the reinforcement of the plant cell wall, and is also involved in responses to wounding or pathogen challenge by the increased formation of cell wall-bound ferulic acid polymers.

Additional enzymes involved in the monolignol biosynthesis pathway are cinnamoyl coenzyme A reductase (CCR) and cinnamyl alcohol dehydrogense (CAD). CCR catalyzes the reduction of the hydroxycinnamoyl CoA esters to produce cinnamaldehydes, whereas CAD catalyzes their reduction to cinnamyl alcohols. (Goujon et al., 2003).

One of the last enzymes involved in the monolignol pathway is cinnamyl alcohol dehydrogenase (CAD), which catalyzes the NADPH dependent conversion of coniferaldehyde, 5-hydroxy-coniferaldehyde, and sinapaldehyde to the corresponding alcohols. (Kim, S. J. et al. (2004) Functional reclassification of the putative cinnamyl alcohol dehydrogenase multigene family in *Arabidopsis, Proc. Natl. Acad. Sci. USA,* 101, pp. 1455-60). In *Arabidopsis,* single mutants of the CAD genes AtCAD-C and AtCAD-D were found to have lower CAD activities, and the double-mutant, obtained by crossing the two mutants, had a 40% decrease in stem lignin content, thus demonstrating that these are the main CAD genes involved in stem lignin synthesis. (Sibout, R. et al. (2005) Cinnamyl Alcohol Dehydrogenase-C and -D are the primary genes involved in lignin biosynthesis in the floral stem of *Arabidopsis, Plant Cell,* 17, pp. 2059-76).

Two enzymes are specific to the monolignol biosynthesis pathway. They are caffeic acid O-methyltransferase (COMT) and cinnamoyl coenzyme A reductase (CCR). COMT was first identified in angiosperms. COMT is capable of converting caffeic acid to ferulic acid, as well as converting 5-hydroxyferulic acid to sinapic acid. (Dixon, R. A., et al. (2001) The biosynthesis of monolignols: a "metabolic grid," or independent pathways to guaiacyl and syringyl units? *Phytochemistry,* 57, pp. 1069-1084). Down regulation of the COMT gene in maize (*Zea mays*) has been shown to cause a significant reduction of COMT activity (a fall of 70 to 85%), resulting in the modification of lignin content and composition, indicating that this enzyme is a key enzyme for lignin synthesis.

Ferulic acid generated by COMT can be hydroxylated by ferulate 5 hydroxylase (F5H), which is a cytochrome P450-dependent monooxygenase, to form 5-hydroxy-ferulic acid. F5H is also capable of hydroxylating coniferaldehyde and coniferyl alcohol to form 5-hydroxy-coniferaldehyde and 5-hydroxy-coniferyl alcohol, respectively. (Meyer, K. et al. (1996) Ferulate-5-hydroxylase from *Arabidopsis thaliana* defines a new family of cytochrome P450-dependent monooxygenases, *Proc. Natl. Acad. Sci. USA,* 93, pp. 6869-74). F5H is believed to be a rate limiting step in syringyl lignin biosynthesis, a proposal supported by the observation that an *Arabidopsis* mutant deficient in F5H expression is also affected at the level of sinapate esters accumulation in siliques and seeds. (Ruegger, M. et al. (1999) Regulation of ferulate-5-hydroxylase expression in *Arabidopsis* in the context of sinapate ester biosynthesis, *Plant Physiol.,* 119, pp. 101-10).

The second enzyme specifically involved in lignol biosynthesis, CCR, catalyzes the conversion of feruloyl CoA and 5-hydroxy-feruloyl CoA into coniferaldehyde and 5-hydroxy-coniferaldehyde, respectively. This step leads directly to the biosynthesis of G (coniferaldehyde) and S (5-hydroxy-coniferaldehyde) lignin units. (Ma et al., 2005). In tobacco, down regulation of the CCR gene using antisense constructs, produced plants with abnormal development and reduced growth, as well as abnormal leaf morphology and collapsed vessels. There was also an associated reduction in the level of G lignin compounds. (Ralph, J. et al. (1998) NMR characterization of altered lignins extracted from tobacco plants down-regulated for lignification enzymes cinnamylalcohol dehydrogenase and cinnamoyl-CoA reductase, *Proc. Natl. Acad. Sci USA,* 95, pp. 12803-8).

Computational Identification of Genes and Transcripts

Remarkably, we have determined the sequences of the jute enzymes involved in lignin biosynthesis. The pathway of lignin biosynthesis has been well characterized and each enzyme is encoded by a gene family in most of the plant species. A total of 106 gene sequences of *A. thaliana* and *P. trichocarpa* were retrieved from NCBI and *P. trichocarpa* genome database (Goujon et al., 2003; Shi et al., 2010). Jute monolignol biosynthesis genes were identified from the gene models of the *Corchorus olitorius* genome assembly and transcriptome data of *C. olitorius* and *C. capsularis* using the program BLASTN with the e-value cut-off at 1e-20. (Altschul, S. F., et al. (1990) Basic local alignment search tool, *J Mol Biol,* 215, pp. 403-410). The resulting gDNA contigs were subjected to gene model prediction using the software AUGUSTUS. (Stanke, M. et al. (2004) AUGUSTUS: a web server for gene finding in eukaryotes, *Nucleic Acids Research,* 32, W309-W312). The gene models and the isotigs from the transcriptome data of *C. olitorius* and *C. capsularis* were searched against the NCBI nr (non-redundant) database for further confirmation.

An amino acid sequence alignment of putative proteins encoded by the ColCAD genes with other CAD proteins available in the NCBI database, using the CLUSTAL W program, is shown in FIGS. 2*a* and 2*b*. The following is a list of the proteins aligned with the putative ColCAD proteins, with the GeneBank Accession Numbers in parentheses: PtcCADL4 (*Populus tricocarpa* cinnamyl alcohol dehydrogenase-like protein, CADL4, gi224138226); RcoCAD (*Ricinus communis* alcohol dehydrogenase, putative, gi25558709); FraCAD (*Fragaria*×*ananassa,* cinnamyl alcohol dehydrogenase, gi13507210) (Chandler et al. (2002) Cloning, expression and immunolocalization pattern of a cinnamyl alcohol dehydrogenase gene from strawberry (*Fragaria*×*ananassa*), *J. Exp. Bot.,* 53 (375), pp. 1723-1734); GhiCAD5 (*Gossypium hirsatum,* cinnamyl alcohol dehydrogenase 5, gi268528129); PtcCAD (*Populus tricocarpa,* gi183585165) ((2010) Towards a systems approach for lignin biosynthesis in *Populus trichocarpa*: transcript abundance and specificity of the monolignol biosynthetic genes, *Plant Cell Physiol.,* 51 (1), pp. 144-163); GhiCAD3 (*Gossypium hirsatum,* gi229368450) (Genes of phenylpropanoid pathway cloning and expression in developing cotton fibre); and GhiCAD (*Gossypium hirsatum,* gi166865124) ((2009) Molecular and biochemical evidence for phenylpropanoid synthesis and presence of wall-linked phenolics in cotton fibers, *J Integr Plant Biol,* 51 (7), pp. 626-637).

An amino acid sequence alignment of putative proteins encoded by the ColCCoAOMT genes with other CCoAOMT proteins available in the NCBI database, using the CLUSTAL W program, is shown in FIG. 3. The following is a list of the proteins aligned with the putative ColCCoAOMT proteins, with the GeneBank Accession Numbers in parentheses: PtrCCoAOMT (*Populus tremuloides*, gi3023436); GhiCCoAOMT2 (*Gossypium hirsatum*, gi229368460); and GhiCCoAOMT1 (*Gossypium hirsatum*, gi253509567).

An amino acid sequence alignment of putative proteins encoded by the Col4CL genes with other 4CL proteins available in the NCBI database, using the CLUSTAL W program, is shown in FIG. 4. The following is a list of the proteins aligned with the putative Col4CL proteins, with the GeneBank Accession Numbers in parentheses: Ccap4CL1 (*Corchorus capsularis*, gi294514718); Rco4CL (*Ricinus communis*, gi255565415); and Ptc4CL (*Populus tricocarpa*, gi224074401).

An amino acid sequence alignment of putative proteins encoded by the Col6HCT genes with other Col6HCT proteins available in the NCBI database, using the CLUSTAL W program, is shown in FIG. 5. The following is a list of the proteins aligned with the putative Col6HCT proteins, with the GeneBank Accession Numbers in parentheses: CycarHCT (*Cynara cardunculus*, gi:73671233) ((2007) Isolation and functional characterization of a cDNA coding a hydroxycinnamoyltransferase involved in phenylpropanoid biosynthesis in *Cynara cardunculus, BMC Plant Biol.* 7, 14); and PtcHCT (*Poplus tricocarpa*, gi183585181).

An amino acid sequence alignment of putative proteins encoded by the ColC3H genes with other C3H proteins available in the NCBI database, using the CLUSTAL W program, is shown in FIG. 6. The following is a list of the proteins aligned with the putative ColC3H proteins, with the GeneBank Accession Numbers in parentheses: EglC3H (*Eucalyptus globulus*, gi:295413824); PtcC3H (*Poplus tricocarpa*, gi:224139664); and PalxPgrC3H (*Poplus alba×Populus grandidentata*, gi166209291).

An amino acid sequence alignment of putative proteins encoded by the ColC4H genes with other C4H proteins available in the NCBI database, using the CLUSTAL W program, is shown in FIG. 7. The following is a list of the proteins aligned with the putative ColC4H proteins, with the GeneBank Accession Numbers in parentheses: GarC4H (*Gossypium arborium*, gi9965897) and GarC4H (*Gossypium arborium*, gi9965899).

An amino acid sequence alignment of putative proteins encoded by the ColPAL genes with other PAL proteins available in the NCBI database, using the CLUSTAL W program, is shown in FIG. 8. The following is a list of the proteins aligned with the putative ColPAL proteins, with the GeneBank Accession Numbers in parentheses: JcoPAL (*Jatropha curcas*, gi113203757) and PtrPAL (*Populus trichocarpa*, gi:183585195).

An amino acid sequence alignment of putative proteins encoded by the ColCCR2 genes with other CCR proteins available in the NCBI database, using the CLUSTAL W program, is shown in FIG. 9. The following is a list of the proteins aligned with the putative ColCCR2 proteins, with the GeneBank Accession Numbers in parentheses: AthCCR (*Arabidopsis thaliana*, gi:15237678); CofCCR (*Camellia oleifera* gi228480464); and AlyCCR (*Arabidopsis lyrata*, gi:297793385).

An amino acid sequence alignment of putative proteins encoded by the ColCCR3 genes with other CCR proteins available in the NCBI database, using the CLUSTAL W program, is shown in FIG. 10. The following is a list of the proteins aligned with the putative ColCCR3 proteins, with the GeneBank Accession Numbers in parentheses: RcoCCR (*Ricinus communis*, gi:255556687) and AthCCR (*Arabidopsis thaliana*, gi:15226955).

An amino acid sequence alignment of putative proteins encoded by the ColF5H genes with other F5H proteins available in the NCBI database, using the CLUSTAL W program, is shown in FIG. 11. The following is a list of the proteins aligned with the putative ColF5H proteins, with the GeneBank Accession Numbers in parentheses: EgIF5H (*Eucalyptus globules*, gi:255970299) and PtcF5H (*Poplus tricocarpa*, gi:6688937).

An amino acid sequence alignment of putative proteins encoded by the ColCOMT genes with other COMT proteins available in the NCBI database, using the CLUSTAL W program, is shown in FIG. 12. The following is a list of the proteins aligned with the putative ColCOMT proteins, with the GeneBank Accession Numbers in parentheses: GhiCOMT (*Gossypium hirsatum*, gi:253509569) and EcaCOMT (*Eucalyptus camaldulensis*, gi:262474806).

Motif Analysis of the Promoter Regions

For each of the predicted gene models, both strands of the upstream regions of 2000 bp were extracted and searched for cis-motif sequences against the PlantCARE database (Lescot, M., et al. (2002) PlantCARE, a database of plant cis-acting regulatory elements and a portal to tools for in silico analysis of promoter sequences, *Nucleic Acids Res*, 30, pp. 325-327). If any portion of the selected sequences were found to be overlapping with a nearby gene, that part of the upstream region was excluded from further analysis. A list of important motifs was compiled that are known to be involved in the response to various developmental processes and stress (Table 1).

TABLE 1

List of motifs found in the promoter region of jute monolignol biosynthetic genes

| | Gene model | Salicylic acid | responsiveness | Myb binding | Wound | Transcription enhancer | Abscisic acid | Ethylene | Auxin | Gibberellin-responsive element | Low temp responsiveness |
|---|---|---|---|---|---|---|---|---|---|---|---|
| PAL | contig_310473_g31 | * | | | | | | | | | |
| | contig_301819_g4 | | | * | | | | | | | |
| | contig_302040_g24 | | * | * | | | * | | | * | |
| | contig_309920_g2 | | | | * | * | * | | | | |
| C4H | contig_311419_g56 | | | | | | | | | | |
| | contig_307848_g46 | | * | | | | | * | | | |
| | contig_384302_g42 | | | | | | | | | | |
| 4CL | contig_331398_g112 | | | | | | | | | | |
| | contig_299467_g73 | | | | | | | | * | * | |

TABLE 1-continued

List of motifs found in the promoter region of jute monolignol biosynthetic genes

|  | Gene model | Salicylic acid | responsiveness | Myb binding | Wound | Transcription enhancer | Abscisic acid | Ethylene | Auxin | Gibberellin-responsive element | Low temp responsiveness |
|---|---|---|---|---|---|---|---|---|---|---|---|
|  | contig_337813_g88 |  |  |  |  | * |  |  |  |  |  |
|  | contig_306165_g86 |  |  |  |  |  |  |  |  | * | * |
|  | contig_309926_g132 |  |  |  |  |  | * |  | * |  |  |
|  | contig_304308_g125 | * |  |  | * | * |  |  |  | * |  |
|  | contig_305998_g57 | * |  | * |  |  |  |  |  |  |  |
| HCT | contig_308231_g128 |  |  |  |  |  | * |  |  |  |  |
| C3H | contig_597141_g180 |  |  |  |  |  |  |  |  |  | * |
| CCoAOMT | contig_306979_g168 |  |  | * |  |  |  |  |  | * |  |
|  | contig_308402_g160 |  |  |  |  |  |  |  |  |  |  |
|  | contig_296218_g172 | * | * |  |  | * |  |  |  | * |  |
|  | contig_311951_g178 |  |  |  |  | * |  |  |  |  |  |
| CCR | contig_310406_g194 |  |  |  |  |  |  |  | * |  |  |
|  | contig_297048_g201 |  | * |  |  |  |  | * |  |  |  |
|  | contig_294439_g187 | * |  |  |  |  |  |  |  |  |  |
|  | contig_309320_g191 |  |  | * |  |  |  |  |  |  |  |
| F5H | contig_304192_g207 |  | * |  |  |  |  |  |  |  |  |
|  | contig_595270_g204 |  |  |  |  |  | * |  |  |  |  |
| COMT | contig_299952_g235 |  | * |  |  |  |  |  |  |  |  |
| CAD | contig_335778_g278 |  |  |  |  |  |  | * |  |  |  |
|  | contig_95812_g280 |  |  |  |  |  |  |  |  |  |  |
|  | contig_321021_g281 |  | * |  |  |  |  |  |  |  |  |
|  | contig_808760_g282 | * |  |  |  |  |  |  |  |  |  |
|  | contig_808760_g284 |  |  |  |  |  | * |  |  |  |  |
|  | contig_356907_g287 |  |  |  |  |  |  |  | * |  |  |
|  | contig_356907_g288 |  |  |  |  | * |  | * |  |  |  |
|  | contig_355903_g289 |  |  |  |  |  | * |  |  |  |  |
|  | contig_306706_g300 |  | * |  |  | * |  |  |  | * |  |
|  | contig_304576_g307 | * | * |  |  | * |  |  |  | * |  |

Polynucleotides of the present invention were isolated by high-throughput sequencing of cDNA libraries comprising jute plant tissue collected from *Corchorus olitorius* L. Some of the polynucleotides of the present invention may be partial sequences, in that, they do not represent a full-length gene encoding a full-length polypeptide. Such partial sequences may be extended by analyzing and sequencing various DNA libraries using primers and/or probes and well known hybridization and/or PCR techniques. Partial sequences may be extended until an open reading frame encoding a polypeptide, a full-length polynucleotide, a gene capable of expressing a polypeptide, or another useful portion of the genome is identified.

Identification of genomic DNA and heterologous species DNA can be accomplished by standard DNA/DNA hybridization techniques, under appropriately stringent conditions, using all or part of a polynucleotide sequence as a probe to screen an appropriate library. Alternatively, PCR techniques using oligonucleotide primers that are designed based on known genomic DNA, cDNA, or protein sequences can be used to amplify and identify genomic and cDNA sequences.

Polypeptides of the present invention may be produced by inserting a polynucleotide sequence of the present invention encoding the desired polypeptide into an expression vector and expressing the polypeptide in an appropriate host. Any of a variety of expression vectors known to those of ordinary skill in the art could be employed. Expression may be achieved in any appropriate host cell that has been transformed or transfected with an expression vector containing a polynucleotide molecule that encodes a recombinant polypeptide. Suitable host cells include prokaryotes, yeast, and higher eukaryotic cells.

Polypeptides that comprise the lignin biosynthetic pathways purified from jute, or produced by recombinant methods, may be used to generate monoclonal antibodies, antibody fragments or derivatives as defined herein, according to known methods. Antibodies that recognize and bind fragments of the polypeptides that comprise the lignin biosynthetic pathways of the invention are also contemplated, provided that the antibodies are specific for polypeptides that comprise the lignin biosynthetic pathway.

The genetic constructs of the present invention may also contain a selection marker that is effective in plant cells, to allow for the detection of transformed cells containing the inventive construct. Such markers, which are well known in the art, typically confer resistance to one or more toxins or create visual signals for its presence under fluorescent microscope. Alternatively, the presence of the desired construct in transformed cells can be determined by means of other techniques well known in the art, such as Southern and Western blots. The genetic construct of the present invention may be linked to a vector having at least one replication system, for example, *E. coli* or yeast (*Saccharomyces cerevisiae*), whereby after each manipulation, the resulting construct can be cloned and sequenced.

The genetic constructs of the present invention may be used to transform a variety of plants, such as monocotyledonous (e.g., rice) and dicotyledonous (e.g., jute, *Arabidopsis*). In a preferred embodiment, the inventive genetic constructs are employed to transform jute. As discussed above, transformation of a plant with a genetic construct of the present invention can be used to produce modified lignin content in the plant.

Techniques for stably incorporating genetic constructs into the genome of target plants are well known in the art and include *Agrobacterium tumefaciens* mediated introduction, electroporation, injection into meristematic tissue or reproductive organs, injection into immature embryos, and the like. The choice of technique will depend upon the target plant/tissue/host to be transformed.

The term "plant" includes whole plants, shoot vegetative organs/structures (e.g., leaves, stems, and tubers), roots, flowers, and floral organs/structures (e.g., bracts, sepals, petals, stamens, carpels, anthers, and ovules), seed (including embryo, endosperm, and seed coat) and fruit (the mature ovary), plant tissue (e.g., vascular tissue, ground tissue, and the like) and cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid, and hemizygous.

Figure 13:
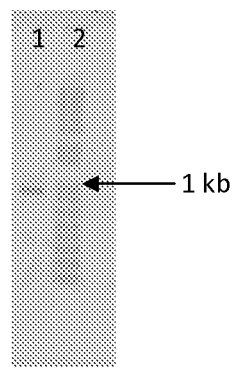
FIG. 13: DNA gel of ColCAD2. Lane 1 shows the isolated ColCAD2 DNA. Lane 2 shows a molecular weight marker.
Figure 14:
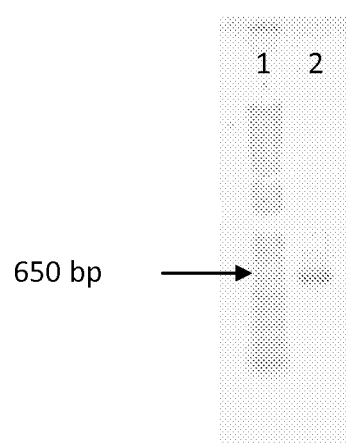
FIG. 14: DNA gel of ColCCoAOMT1. Lane 2 shows the isolated ColCCoAOMT1 DNA. Lane 1 shows a molecular weight marker.
Figure 15:
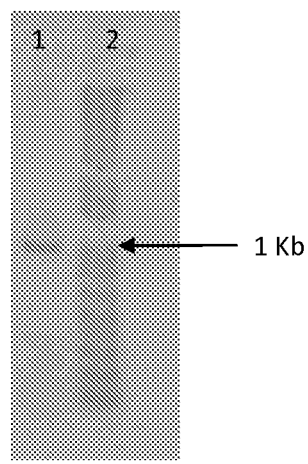
FIG. 15: DNA gel of Col4CL1. Lane 1 shows the isolated Col4CL1 DNA. Lane 2 shows a molecular weight marker.
Figure 16:
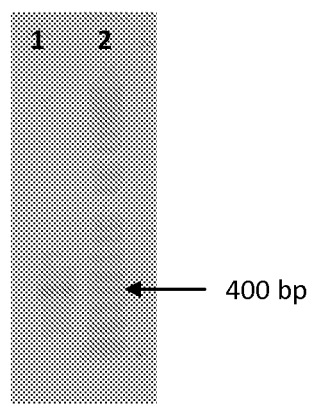
FIG. 16: DNA gel of ColCCR3. Lane 1 shows the isolated ColCCR3 DNA. Lane 2 shows a molecular weight marker.
Figure 17:
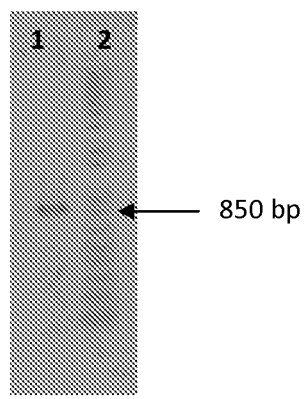
FIG. 17: DNA gel of ColF5H. Lane 1 shows the isolated ColF5H DNA. Lane 2 shows a molecular weight marker.

DNA gels of PCR reactions using forward and reverse primers for several jute enzymes are shown in FIGS. 13-17. In FIG. 13, the DNA gel is of CAD2 from *Corchorus olitorius*. Lane 1 is the PCR product of CAD2 using cDNA as a template. The forward primer and reverse primer are SEQ ID NO. 53 and 54, respectively. Lane 2 is the 1 Kb+ladder. In FIG. 14, the DNA gel is of CCoAOMT1 from *Corchorus olitorius*. Lane 1 is the 1 Kb+ladder, and Lane 2 is the PCR product of CCoAOMT1 using cDNA as a template. The forward primer and reverse primer are SEQ ID NO. 55 and 56, respectively. In FIG. 15, the DNA gel of 4CL1 from *Corchorus olitorius*. Lane 1 is the 1 Kb+ladder, and Lane 2 is the PCR product of 4CL1 using cDNA as a template. The forward primer and reverse primer are SEQ ID NO. 57 and 58, respectively. In FIG. 16, the DNA gel is of CCR3 from *Corchorus olitorius*. Lane 1 is the 1 Kb+ladder, and Lane 2 is the PCR product of CCR3 using cDNA as a template. The forward primer and reverse primer are SEQ ID NO. 59 and 60, respectively. In FIG. 17, the DNA gel is of F5H from *Corchorus olitorius*. Lane 1 is the 1 Kb+ladder, and Lane 2 is the PCR product of F5H using cDNA as a template. The forward primer and reverse primer are SEQ ID NO. 61 and 62, respectively.

DEFINITIONS

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. The practice of the present invention contemplates a wide variety of stably transformed plant cells.

An "expression cassette" refers to a nucleic acid construct, which when introduced into a host cell, results in transcription and/or translation of a RNA and/or polypeptide, respectively. The expression cassette may include a nucleic acid comprising a promoter sequence, with or without a sequence containing mRNA polyadenylation signals, and one or more restriction enzyme sites located downstream from the promoter allowing insertion of heterologous gene sequences. The expression cassette is capable of directing the expression of a heterologous protein when the gene encoding the heterologous protein is operably linked to the promoter by insertion into one of the restriction sites. The recombinant expression cassette allows expression of the heterologous protein in a host cell when the expression cassette containing the heterologous protein is introduced into the host cell. Expression cassettes can be derived from a variety of sources depending on the host cell to be used for expression. For example, an expression cassette can contain components derived from a viral, bacterial, insect, plant, or mammalian source. In the case of both expression of transgenes and inhibition of endogenous genes (e.g., by antisense, or sense suppression) the inserted polynucleotide sequence need not be identical and can be "substantially identical" to a sequence of the gene from which it was derived. Preferably the recombinant expression cassette allows expression at an early stage of infection and/or it allows expression in substantially all cells of an organism, such as a plant. Examples of expression cassettes suitable for transformation of plants can be found in U.S. Pat. Nos. 5,880,333 and 6,002,072; International Patent Publications Nos. WO/1990/002189 and WO/2000/026388; Ainley and Key (1990) *Plant Mol.* Biol., 14, pp. 949-967; and Birch (1997) *Annu. Rev. Plant Physiol. Plant Mol. Biol.*, 48, pp. 297-326, all of which are herein incorporated by reference.

The term "host cell" refers to a cell from any organism. Preferred host cells are derived from plants, bacteria, yeast, fungi, insects, or other animals. The term "recombinant host cell" (or simply "host cell") refers to a cell into which a recombinant expression vector has been introduced. It should be understood that the term "host cell" is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. Methods for introducing polynucleotide sequences into various types of host cells are well known in the art. Provided are host cells or progeny of host cells transformed with the recombinant expression cassettes of the present invention. The host cells may be plant cells. Preferably, the plant cells are jute cells.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g., enhancers) in an expression cassette. Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

The term "nucleic acid construct" or "DNA construct" is sometimes used to refer to a coding sequence or sequences operably linked to appropriate regulatory sequences and inserted into an expression cassette for transforming a cell. This term may be used interchangeably with the term "transforming DNA" or "transgene". Such a nucleic acid construct may contain a coding sequence for a gene product of interest, along with a selectable marker gene and/or a reporter gene. The term "selectable marker gene" refers to a gene encoding a product that, when expressed, confers a selectable phenotype such as antibiotic resistance on a transformed cell. The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. When the heterologous region encodes a plant gene, the gene will usually be flanked by DNA that does not flank the plant genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct" is also used to refer to a heterologous region, particularly one constructed for use in transformation of a cell.

The term "vector" is intended to refer to a nucleic acid molecule capable of transporting another nucleic acid to which it has been linked. One type of vector is a "plasmid," which refers to a circular double-stranded DNA loop into which additional DNA segments may be ligated. Another type of vector is a viral vector, where additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

"Percentage of sequence identity" is determined by comparing two optimally aligned sequences over a comparison window, where the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 25% sequence identity compared to a reference sequence as determined using the programs described herein; preferably BLAST using standard parameters, as described. Alternatively, percent identity can be any integer from 25% to 100%. More preferred embodiments include polynucleotide sequences that have at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% sequence identity compared to a reference sequence. These values can be appropriately adjusted to determine corresponding identity of proteins encoded by two nucleotide sequences by taking into account codon degeneracy, amino acid similarity, reading frame positioning, and the like.

The term "substantial identity" of amino acid sequences (and of polypeptides having these amino acid sequences) normally means sequence identity of at least 40% compared to a reference sequence as determined using the programs described herein; preferably BLAST using standard parameters, as described. Preferred percent identity of amino acids can be any integer from 40% to 100%. More preferred embodiments include amino acid sequences that have at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity compared to a reference sequence. Polypeptides that are "substantially identical" share amino acid sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

INCORPORATION BY REFERENCE

All of the U.S. patents, U.S. published patent applications, and published PCT applications that designate the U.S. cited herein are hereby incorporated by reference.

EQUIVALENTS

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed.

What is claimed is:

1. A nucleic acid molecule comprising a coding nucleotide sequence (cDNA) having 100% sequence identity to a nucleic acid sequence selected from the group consisting of: SEQ ID NO: 1, 3, 5, 7, 9, 11, 13, and 15, wherein said nucleic acid molecule encodes a cinnamyl alcohol dehydrogenase (CAD).

2. An expression vector comprising the nucleic acid molecule of claim 1.

3. A transgenic plant comprising the expression vector of claim claim 2.

4. A material derived from the transgenic plant of claim 3, wherein the material comprises said expression vector.

5. A seed from the transgenic plant of claim 3, wherein the seed comprises said expression vector.

6. A method for making a transgenic plant, comprising the steps of:

transfecting at least one plant cell with the expression vector of claim 2; and
growing said at least one plant cell into a plant.

7. A method of improving fiber yield, or fiber strength in a jute plant, comprising incorporating in the jute plant the nucleic acid molecule of claim 1.

8. The nucleic acid molecule of claim 1, wherein said nucleic acid sequence is SEQ ID NO: 1.

9. The nucleic acid molecule of claim 1, wherein said nucleic acid sequence is SEQ ID NO: 3.

10. The nucleic acid molecule of claim 1, wherein said nucleic acid sequence is SEQ ID NO: 5.

11. The nucleic acid molecule of claim 1, wherein said nucleic acid sequence is SEQ ID NO: 7.

12. The nucleic acid molecule of claim 1, wherein said nucleic acid sequence is SEQ ID NO: 9.

13. The nucleic acid molecule of claim 1, wherein said nucleic acid sequence is SEQ ID NO: 11.

14. The nucleic acid molecule of claim 1, wherein said nucleic acid sequence is SEQ ID NO: 13.

15. The nucleic acid molecule of claim 1, wherein said nucleic acid sequence is SEQ ID NO: 15.

* * * * *

SEQUENCE LISTING

```
<160> NUMBER OF SEQ ID NOS: 93

<210> SEQ ID NO 1
<211> LENGTH: 1089
<212> TYPE: DNA
<213> ORGANISM: Corchorus olitorius

<400> SEQUENCE: 1
atgggcagtt taccagagca agagcacccc aaagaggctt ttggatgggc agctagagac      60
acttctggcc acctttctcc cttcaaattc tccagaaggg caacaggaga aaaagatgtg     120
gcattcaaag tgctttattg tgggatatgc cactcagatc ttcatatgat caagaatgaa     180
tggggcactg ccatctaccc tatggtccct gggcatgaga ttgttggaga agtaacagag     240
gtaggaagca aggtagaaaa gttcaaagtt ggagacaaag ttggagctgg agtcttggtt     300
aattcgtgcc gctcttgcga taactgtgct aataatcttg aaaactactg cccacaagcc     360
gttttcactt atgctgcaaa aaactacgat ggaaccatta cctatggagg ctactccgac     420
accatggttg ccgatgagca cttcataatc cgaattccag acactctgcc tctcgacgcc     480
gccgctcccc tgctctgcgc cggaatcaca gtttatagtc ctttgagata tttccaactc     540
gacaaaccgg gtttccatat tggtgtggtt ggccttggtg gtttaggcca tatggctgtc     600
aaatttgcca aggctatggg ggccaaggtc acagtgatta gcacctctcc caacaagaag     660
aaggaagctt tggaaaatct tggtgctgat tcgtttttga ttagcgcaga gcaggatcag     720
ctccagactg ccatgggaac aatggatggt atcattgata cagtgtctgc tccacaccct     780
ttactgccat tgatcggttt gttaaagtct catgcaaagc ttattttggt tggtcttcca     840
gacaaaccac ttgagctaca tgtcttccct atgatcatag ggaggaagac ggtggcagga     900
agtggcgtgg gagggataga ggagactcag gagatgatga attttgcagc caaatatgac     960
ttgaaaccag acattgaagt tatacccgtt gactatgtca acactgccat ggaacgcctt    1020
gtcaaaggcg atgttaaata cagatttgtc atcgacattg ggaacacact gaaggctaca    1080
tcatcttaa                                                            1089

<210> SEQ ID NO 2
<211> LENGTH: 362
<212> TYPE: PRT
<213> ORGANISM: Corchorus olitorius

<400> SEQUENCE: 2

Met Gly Ser Leu Pro Glu Gln Glu His Pro Lys Glu Ala Phe Gly Trp
1               5                   10                  15

Ala Ala Arg Asp Thr Ser Gly His Leu Ser Pro Phe Lys Phe Ser Arg
            20                  25                  30

Arg Ala Thr Gly Glu Lys Asp Val Ala Phe Lys Val Leu Tyr Cys Gly
        35                  40                  45

Ile Cys His Ser Asp Leu His Met Ile Lys Asn Glu Trp Gly Thr Ala
    50                  55                  60

Ile Tyr Pro Met Val Pro Gly His Glu Ile Val Gly Glu Val Thr Glu
65                  70                  75                  80

Val Gly Ser Lys Val Glu Lys Phe Lys Val Gly Asp Lys Val Gly Ala
                85                  90                  95
```

-continued

```
Gly Val Leu Val Asn Ser Cys Arg Ser Cys Asp Asn Cys Ala Asn Asn
            100                 105                 110

Leu Glu Asn Tyr Cys Pro Gln Ala Val Phe Thr Tyr Ala Ala Lys Asn
        115                 120                 125

Tyr Asp Gly Thr Ile Thr Tyr Gly Gly Tyr Ser Asp Thr Met Val Ala
    130                 135                 140

Asp Glu His Phe Ile Ile Arg Ile Pro Asp Thr Leu Pro Leu Asp Ala
145                 150                 155                 160
Ala Ala Pro Leu Leu Cys Ala Gly Ile Thr Val Tyr Ser Pro Leu Arg
                165                 170                 175
Tyr Phe Gln Leu Asp Lys Pro Gly Phe His Ile Gly Val Val Gly Leu
            180                 185                 190
Gly Gly Leu Gly His Met Ala Val Lys Phe Ala Lys Ala Met Gly Ala
        195                 200                 205

Lys Val Thr Val Ile Ser Thr Ser Pro Asn Lys Lys Lys Glu Ala Leu
    210                 215                 220

Glu Asn Leu Gly Ala Asp Ser Phe Leu Ile Ser Ala Glu Gln Asp Gln
225                 230                 235                 240
Leu Gln Thr Ala Met Gly Thr Met Asp Gly Ile Ile Asp Thr Val Ser
                245                 250                 255
Ala Pro His Pro Leu Leu Pro Leu Ile Gly Leu Leu Lys Ser His Ala
            260                 265                 270
Lys Leu Ile Leu Val Gly Leu Pro Asp Lys Pro Leu Glu Leu His Val
        275                 280                 285
Phe Pro Met Ile Ile Gly Arg Lys Thr Val Ala Gly Ser Gly Val Gly
    290                 295                 300

Gly Ile Glu Glu Thr Gln Glu Met Met Asn Phe Ala Ala Lys Tyr Asp
305                 310                 315                 320
Leu Lys Pro Asp Ile Glu Val Ile Pro Val Asp Tyr Val Asn Thr Ala
                325                 330                 335
Met Glu Arg Leu Val Lys Gly Asp Val Lys Tyr Arg Phe Val Ile Asp
            340                 345                 350
Ile Gly Asn Thr Leu Lys Ala Thr Ser Ser
        355                 360

<210> SEQ ID NO 3
<211> LENGTH: 1086
<212> TYPE: DNA
<213> ORGANISM: Corchorus olitorius

<400> SEQUENCE: 3
atgagcagat tgccagagga agagcaccct aacaaggctt ttggatgggc agccagagac      60
acttctggag ttctctctcc cttcaaattt tccagaaggg caacagggga gaaggatgtg     120
gcattcaagg tgctttattg tgggatatgc cattctgatc ttcacatggt caagaatgaa     180
tggggcgttt ccatctaccc tcttgtccct gggcacgaga ttgttggaga agtgacagaa     240
gtgggaagca aggtacaaaa gttcaaagtt ggagacagag ttggtgtcgg ctgcatggtt     300
gggtcatgtc attcctgtga tagctgcacc aacaatctcg agaactattg cccaaaaatg     360
atacttactt atggggcaaa gtactatgat ggaactatta catatggagg ttactctgac     420
actatggttg cagatgaaca cttcattgtc cgaattcctg aaaatttgcc acttgatgct     480
gctgctcctc ttctttgtgc tggaatcaca gtttatagcc cattgaaata ttatggactt     540
gacaagcctg gtttgcatgt gggtgtggtt ggccttggtg ggctaggcca tatggctgtc     600
```

```
aaatttgcca aggctatggg ggccaaggtc acagtaatta gcacttctcc taataagaag    660
aaggaagctt tggaaaatct tggtgctgat tcattttggg tcagcaaaga ccaagatcag    720
attcaggccg ccatggacac attggatgga atcattgata cagtgtcagc tcaacatcct    780
atcctgccat tgcttgggat gttaaagact aatggaaagc ttgttctggt tggtgcaccg    840
gagaaaccac ttgagttgcc ggcgttccct ttactcggaa agaggaggct agtagcagga    900
agcatgattg ggggaatgaa ggagacacaa gagatgattg attttgcagc taaacacaac    960
attaaaccag acattgaagt tatagctatg gattatgtca acactgccat ggaccgcctt   1020
ctcaaagctg atgtcaaata cagatttgtc attgacattg caacacatt gaaaccaacc    1080 ccttaa                                                                1086
```

<210> SEQ ID NO 4
<211> LENGTH: 361
<212> TYPE: PRT
<213> ORGANISM: Corchorus olitorius

<400> SEQUENCE: 4

```
Met Ser Arg Leu Pro Glu Glu His Pro Asn Lys Ala Phe Gly Trp
1               5                   10                  15

Ala Ala Arg Asp Thr Ser Gly Val Leu Ser Pro Phe Lys Phe Ser Arg
            20                  25                  30

Arg Ala Thr Gly Glu Lys Asp Val Ala Phe Lys Val Leu Tyr Cys Gly
        35                  40                  45

Ile Cys His Ser Asp Leu His Met Val Lys Asn Glu Trp Gly Val Ser
    50                  55                  60

Ile Tyr Pro Leu Val Pro Gly His Glu Ile Val Gly Glu Val Thr Glu
65                  70                  75                  80

Val Gly Ser Lys Val Gln Lys Phe Lys Val Gly Asp Arg Val Gly Val
                85                  90                  95

Gly Cys Met Val Gly Ser Cys His Ser Cys Asp Ser Cys Thr Asn Asn
            100                 105                 110

Leu Glu Asn Tyr Cys Pro Lys Met Ile Leu Thr Tyr Gly Ala Lys Tyr
        115                 120                 125

Tyr Asp Gly Thr Ile Thr Tyr Gly Gly Tyr Ser Asp Thr Met Val Ala
    130                 135                 140

Asp Glu His Phe Ile Val Arg Ile Pro Glu Asn Leu Pro Leu Asp Ala
145                 150                 155                 160

Ala Ala Pro Leu Leu Cys Ala Gly Ile Thr Val Tyr Ser Pro Leu Lys
                165                 170                 175

Tyr Tyr Gly Leu Asp Lys Pro Gly Leu His Val Gly Val Val Gly Leu
            180                 185                 190

Gly Gly Leu Gly His Met Ala Val Lys Phe Ala Lys Ala Met Gly Ala
        195                 200                 205

Lys Val Thr Val Ile Ser Thr Ser Pro Asn Lys Lys Glu Ala Leu
    210                 215                 220

Glu Asn Leu Gly Ala Asp Ser Phe Leu Val Ser Lys Asp Gln Asp Gln
225                 230                 235                 240

Ile Gln Ala Ala Met Asp Thr Leu Asp Gly Ile Ile Asp Thr Val Ser
                245                 250                 255

Ala Gln His Pro Ile Leu Pro Leu Gly Met Leu Lys Thr Asn Gly
            260                 265                 270

Lys Leu Val Leu Val Gly Ala Pro Glu Lys Pro Leu Glu Leu Pro Ala
        275                 280                 285
```

```
Phe Pro Leu Leu Gly Lys Arg Arg Leu Val Ala Gly Ser Met Ile Gly
        290                 295                 300

Gly Met Lys Glu Thr Gln Glu Met Ile Asp Phe Ala Ala Lys His Asn
305                 310                 315                 320

Ile Lys Pro Asp Ile Glu Val Ile Ala Met Asp Tyr Val Asn Thr Ala
                325                 330                 335

Met Asp Arg Leu Leu Lys Ala Asp Val Lys Tyr Arg Phe Val Ile Asp
            340                 345                 350

Ile Gly Asn Thr Leu Lys Pro Thr Pro
            355                 360

<210> SEQ ID NO 5
<211> LENGTH: 921
<212> TYPE: DNA
<213> ORGANISM: Corchorus olitorius

<400> SEQUENCE: 5
atgatcaaga acgactgggg ctattccatc tatcctctcg tccctggaca tgaaatagtt      60
ggggaagtaa cagaggtggg ttctaaggta agcaagttca agttggaga caaggttgga     120 gttggataca tggttggatc atgccgttct tgcgatgatt gctccgataa tcttgaaaac     180
tactgtccga aaatgatacc tacttgtggg gcaaagtacc atgatggaac tattacatat     240
ggaggtttct ctgacactat ggttgccgat gaacacttcg ttgtccgaat tccgacaac      300 atgccccttg atgcggcggc tcctcttctt tgtgccggaa ccacagttta cagtccaatg     360
aaatattatg gactcgacaa gcctggtttg catttgggtg ttgttggatt gggagggctt     420
ggccatgttg ctgtgaaatt tgcaaaagct atgggggcca aggtgacagt gatcagcacc     480
tctcctagta agaagcagga agctttggaa attcttggtg ctgattcgtt tttggttagc     540
cgggacgaag atcagcttaa ggctgccaag gcacaatga atggtatagt ggatacggta     600
tctgccaaac atgatctgca gccattactt ggactgttga agaatcatgg aaagcttgtt     660
ctaattggtg ttccggtaaa gccatatgag ctaccagcag cttctttgat cttggggagg     720
aagctagtag gaggaagtaa cgtcggagga ttggaagaga ctcaagagat gattgatttt     780
gcagcaaaac acaatgtgac agcaaacgtt gaagtgattc cgatggatta tgtgaacact     840
gcctttgagc gacttgcaaa agccgatgtt agatatcgat ttgtcgttga cattggcaac     900
accttgaaga cttcgtctta a                                              921

<210> SEQ ID NO 6
<211> LENGTH: 306
<212> TYPE: PRT
<213> ORGANISM: Corchorus olitorius

<400> SEQUENCE: 6

Met Ile Lys Asn Asp Trp Gly Tyr Ser Ile Tyr Pro Leu Val Pro Gly
1               5                   10                  15

His Glu Ile Val Gly Glu Val Thr Glu Val Gly Ser Lys Val Ser Lys
                20                  25                  30

Phe Lys Val Gly Asp Lys Val Gly Val Gly Tyr Met Val Gly Ser Cys
            35                  40                  45

Arg Ser Cys Asp Asp Cys Ser Asp Asn Leu Glu Asn Tyr Cys Pro Lys
        50                  55                  60

Met Ile Pro Thr Cys Gly Ala Lys Tyr His Asp Gly Thr Ile Thr Tyr
65                  70                  75                  80
```

Gly Gly Phe Ser Asp Thr Met Val Ala Asp Glu His Phe Val Val Arg
            85                  90                  95

Ile Pro Asp Asn Met Pro Leu Asp Ala Ala Pro Leu Leu Cys Ala
        100                 105                 110

Gly Thr Thr Val Tyr Ser Pro Met Lys Tyr Tyr Gly Leu Asp Lys Pro
            115                 120                 125

Gly Leu His Leu Gly Val Val Gly Leu Gly Gly Leu Gly His Val Ala
    130                 135                 140

Val Lys Phe Ala Lys Ala Met Gly Ala Lys Val Thr Val Ile Ser Thr
145                 150                 155                 160

Ser Pro Ser Lys Lys Gln Glu Ala Leu Glu Ile Leu Gly Ala Asp Ser
                165                 170                 175

Phe Leu Val Ser Arg Asp Glu Asp Gln Leu Lys Ala Ala Lys Gly Thr
            180                 185                 190

Met Asn Gly Ile Val Asp Thr Val Ser Ala Lys His Asp Leu Gln Pro
        195                 200                 205

Leu Leu Gly Leu Leu Lys Asn His Gly Lys Leu Val Leu Ile Gly Val
    210                 215                 220

Pro Val Lys Pro Tyr Glu Leu Pro Ala Ala Ser Leu Ile Leu Gly Arg
225                 230                 235                 240

Lys Leu Val Gly Gly Ser Asn Val Gly Gly Leu Glu Glu Thr Gln Glu
                245                 250                 255

Met Ile Asp Phe Ala Ala Lys His Asn Val Thr Ala Asn Val Glu Val
            260                 265                 270

Ile Pro Met Asp Tyr Val Asn Thr Ala Phe Glu Arg Leu Ala Lys Ala
        275                 280                 285

Asp Val Arg Tyr Arg Phe Val Val Asp Ile Gly Asn Thr Leu Lys Thr
    290                 295                 300

Ser Ser
305

<210> SEQ ID NO 7
<211> LENGTH: 1065
<212> TYPE: DNA
<213> ORGANISM: Corchorus olitorius

<400> SEQUENCE: 7

```
atggattctc aaaccaaatc tgataactgc cttgggtggg ccgccagaga tccatctgga    60
gttctgtcac cctacacatt tagtcgccgg cctcttggaa gtaatgatgt ttccataaag   120
attaccact gtggagtttg ttatgctgat tcatttggt ctaggaataa gcatggagat    180
agtatgtacc ctgtggtccc cgggcatgaa attgctggtg ttgtcaagga ggttggctcg   240
aatgttcacc gcttcaaggt tggtgatcct gttggagtgg gaacttatgt taactcatgc   300
agagattgtg agtactgcaa tgatggcctt gaagttcatt gtgaaaaaat agttcttacc   360
tttaattgta ttgatgagga tggaacagtc actaaaggcg ttattctaa ccatatcatt    420
gtccacgaaa ggtactgctt aagaatacct agcaattatc ctttggcttc agcagcacct   480
ttgctttgtg ctggcatcac tgtttatgca ccaatgatgc gtcataacat gaatcagcct   540
ggcaaatcat taggagtgat tgggctcggt ggccttggtc acatggcagt gaagtttggg   600
aaggcttttg gttgcatgt aacagtttta agcacaagca tatctaagaa agatgaggcg   660
ttgagtcttc ttggtgcaga caactttgtt gtctcctctg accaagagca gatgaagggc   720
ctatcgaagt cattggactt tatagttgac actgcatctg tgatcatcc ctttgatccc   780
```

```
tacatgtcac tcctgaagat tgctggtgtt tatgtccttg ttgggttccc aagtgaagtc    840
aaattcagcc ctgcaagtct caatctgggt atgagaacaa tctcaggaag cgtaacgggg    900
ggagtaaaag tgatccagga gatgatagac ttttgtgctg ctcataaagt ttacccgcag    960
atagaagtaa tcccaattca atatgcaaat gaagctcttg agaggctaga aagagggat   1020 gtgaagtaca ggtttgtgat tgacatcgag aacagcctga aatga                  1065
```

<210> SEQ ID NO 8
<211> LENGTH: 354
<212> TYPE: PRT
<213> ORGANISM: Corchorus olitorius

<400> SEQUENCE: 8

```
Met Asp Ser Gln Thr Lys Ser Asp Asn Cys Leu Gly Trp Ala Ala Arg
1               5                   10                  15

Asp Pro Ser Gly Val Leu Ser Pro Tyr Thr Phe Ser Arg Arg Pro Leu
            20                  25                  30

Gly Ser Asn Asp Val Ser Ile Lys Ile Thr His Cys Gly Val Cys Tyr
        35                  40                  45

Ala Asp Phe Ile Trp Ser Arg Asn Lys His Gly Asp Ser Met Tyr Pro
    50                  55                  60

Val Val Pro Gly His Glu Ile Ala Gly Val Val Lys Glu Val Gly Ser
65                  70                  75                  80

Asn Val His Arg Phe Lys Val Gly Asp Pro Val Gly Val Gly Thr Tyr
                85                  90                  95

Val Asn Ser Cys Arg Asp Cys Glu Tyr Cys Asn Asp Gly Leu Glu Val
            100                 105                 110

His Cys Glu Lys Ile Val Leu Thr Phe Asn Cys Ile Asp Glu Asp Gly
        115                 120                 125

Thr Val Thr Lys Gly Gly Tyr Ser Asn His Ile Ile Val His Glu Arg
    130                 135                 140

Tyr Cys Leu Arg Ile Pro Ser Asn Tyr Pro Leu Ala Ser Ala Ala Pro
145                 150                 155                 160

Leu Leu Cys Ala Gly Ile Thr Val Tyr Ala Pro Met Met Arg His Asn
                165                 170                 175

Met Asn Gln Pro Gly Lys Ser Leu Gly Val Ile Gly Leu Gly Gly Leu
            180                 185                 190

Gly His Met Ala Val Lys Phe Gly Lys Ala Phe Gly Leu His Val Thr
        195                 200                 205

Val Leu Ser Thr Ser Ile Ser Lys Lys Asp Glu Ala Leu Ser Leu Leu
    210                 215                 220

Gly Ala Asp Asn Phe Val Val Ser Ser Asp Gln Glu Gln Met Lys Gly
225                 230                 235                 240

Leu Ser Lys Ser Leu Asp Phe Ile Val Asp Thr Ala Ser Gly Asp His
                245                 250                 255

Pro Phe Asp Pro Tyr Met Ser Leu Leu Lys Ile Ala Gly Val Tyr Val
            260                 265                 270

Leu Val Gly Phe Pro Ser Glu Val Lys Phe Ser Pro Ala Ser Leu Asn
        275                 280                 285

Leu Gly Met Arg Thr Ile Ser Gly Ser Val Thr Gly Val Lys Val
    290                 295                 300

Ile Gln Glu Met Ile Asp Phe Cys Ala Ala His Lys Val Tyr Pro Gln
305                 310                 315                 320

Ile Glu Val Ile Pro Ile Gln Tyr Ala Asn Glu Ala Leu Glu Arg Leu
```

```
                    325                 330                 335
Glu Lys Arg Asp Val Lys Tyr Arg Phe Val Ile Asp Ile Glu Asn Ser
            340                 345                 350
Leu Lys

<210> SEQ ID NO 9
<211> LENGTH: 1092
<212> TYPE: DNA
<213> ORGANISM: Corchorus olitorius

<400> SEQUENCE: 9
atggctaagt catcacctga agaagagcac cctgttaagg cctttggctg ggctgccagg      60
gacacttctg gtcatctctc tcctttcaac ttctccagaa gggcaactgg tgaaggagat     120
gtgaggttta aggtgttata ttgtggaata tgccattctg accttcattt tatcaagaat     180
gaatggaact tctccatcta tcctttggtt cccgggcatg aaattgtggg ggaagtgaca     240
gaagttggca aaaagttcaa aaggttaag attggagaca agtgggtgt gggatgcatt       300
attggtgctt gtcacacttg tgagagttgt gccaatgacc ttgaaaatta ctgtcctaaa     360
gcaattgcaa cctacaatgg gacttactat gatggaacca tgacatacgg aggctactcc     420
gattcaatgg ttgccgatga acgatacgtc gttcagattc ctgatggcat ggcccttgac     480
tctgctgccc cattgctctg tgctggaatt actgtttaca gtccattgaa gtattttgga     540
ttaggtgaag ctggtaatca cattggcatt gttggccttg gtggccttgg ccatgtagct     600
gttaagtttg ccaaggcttt ggggtccaaa gttacagtaa ttagcacttc ccctggtaag     660
aagaaggaag ccttggaact tcttggggct gattcgttct tggttagccg tgaccaagac     720
gagatgcagg ctgccatggg cacattggat gggatcatag acacagtctc tgccgttcat     780
ccaattatgc cattgcttgg tcttctgaaa tcccatggaa aactcattat ggtgggcgca     840
ccaatcgaac cacttgagtt acctgtcttt tcttttgatca tgggaaggaa gacgatggct     900
gggagtggaa ttggaggaat gaaagagaca caagagatga ttgattttgc agcaaaacac     960
aacataaaag cagacatcga agtgattccg atggattatg tgaacaaagc tatggaaaga    1020
cttgaaaagg gtgatgttag atacagattc gtaattgaca ttggaaacac cttggctact    1080
accaagccctt ag                                                        1092

<210> SEQ ID NO 10
<211> LENGTH: 363
<212> TYPE: PRT
<213> ORGANISM: Corchorus olitorius

<400> SEQUENCE: 10

Met Ala Lys Ser Ser Pro Glu Glu His Pro Val Lys Ala Phe Gly
1               5                   10                  15
Trp Ala Ala Arg Asp Thr Ser Gly His Leu Ser Pro Phe Asn Phe Ser
            20                  25                  30
Arg Arg Ala Thr Gly Glu Gly Asp Val Arg Phe Lys Val Leu Tyr Cys
        35                  40                  45
Gly Ile Cys His Ser Asp Leu His Phe Ile Lys Asn Glu Trp Asn Phe
    50                  55                  60
Ser Ile Tyr Pro Leu Val Pro Gly His Glu Ile Val Gly Glu Val Thr
65                  70                  75                  80
Glu Val Gly Lys Lys Val Gln Val Lys Ile Gly Asp Lys Val Gly
                85                  90                  95
```

Val Gly Cys Ile Ile Gly Ala Cys His Thr Cys Glu Ser Cys Ala Asn
            100                 105                 110

Asp Leu Glu Asn Tyr Cys Pro Lys Ala Ile Ala Thr Tyr Asn Gly Thr
        115                 120                 125

Tyr Tyr Asp Gly Thr Met Thr Tyr Gly Gly Tyr Ser Asp Ser Met Val
    130                 135                 140

Ala Asp Glu Arg Tyr Val Val Gln Ile Pro Asp Gly Met Ala Leu Asp
145                 150                 155                 160

Ser Ala Ala Pro Leu Leu Cys Ala Gly Ile Thr Val Tyr Ser Pro Leu
                165                 170                 175

Lys Tyr Phe Gly Leu Gly Glu Ala Gly Asn His Ile Gly Ile Val Gly
            180                 185                 190

Leu Gly Gly Leu Gly His Val Ala Val Lys Phe Ala Lys Ala Leu Gly
        195                 200                 205

Ser Lys Val Thr Val Ile Ser Thr Ser Pro Gly Lys Lys Lys Glu Ala
    210                 215                 220

Leu Glu Leu Leu Gly Ala Asp Ser Phe Leu Val Ser Arg Asp Gln Asp
225                 230                 235                 240

Glu Met Gln Ala Ala Met Gly Thr Leu Asp Gly Ile Ile Asp Thr Val
                245                 250                 255

Ser Ala Val His Pro Ile Met Pro Leu Leu Gly Leu Leu Lys Ser His
            260                 265                 270

Gly Lys Leu Ile Met Val Gly Ala Pro Ile Glu Pro Leu Glu Leu Pro
        275                 280                 285

Val Phe Ser Leu Ile Met Gly Arg Lys Thr Met Ala Gly Ser Gly Ile
    290                 295                 300

Gly Gly Met Lys Glu Thr Gln Glu Met Ile Asp Phe Ala Ala Lys His
305                 310                 315                 320

Asn Ile Lys Ala Asp Ile Glu Val Ile Pro Met Asp Tyr Val Asn Lys
                325                 330                 335

Ala Met Glu Arg Leu Glu Lys Gly Asp Val Arg Tyr Arg Phe Val Ile
            340                 345                 350

Asp Ile Gly Asn Thr Leu Ala Thr Thr Lys Pro
        355                 360

<210> SEQ ID NO 11
<211> LENGTH: 1080
<212> TYPE: DNA
<213> ORGANISM: Corchorus olitorius

<400> SEQUENCE: 11
atggctatgg aaacacctaa ccacactcag acggtagcag ggtgggctgc tcataattcc      60
tcaggcaaga tcgtccctta caccttcaaa agaagggaaa atggcgtgaa cgatgtgacc     120
attaaagtga tgtattgtgg gatctgccat actgatctcc accatgttaa gaacgattgg     180
ggtatcacca tgtatcctgt agttcccggg catgaaatta ctggggtgat caccaagatt     240
ggaaacaatg tgaagaattt caaagtggga gacagggtag gtgtgggttg cttggcagca     300
tcctgtttgg aatgcgagtt ctgtaaaagc tcgcaagaga actactgtga ccaaatccag     360
ttcacttaca atggcatctt tgggatggta gcgttactt atggcggcta ttcccaaatg     420
ttagtcgccg atcaccggta cgttgttcgt gtgccggata acctgccgat ggacgccgca     480
gcgccactgt tgtgtgccgg gatcaccgtt tcagcccca tgaaagatag ccaactgctc     540
gagtcaccgg gcaaaaaagt gggcatagtt ggtttaggcg gtctcggtca tgtcgctgtc     600

-continued

```
aaaatggcaa aggcatttgg tcatcatgtg accgtgataa gcacttctcc atcaaaagaa    660
aaggaagcta acagcgtttg gggcgcagat gatttcatag ttagcaccaa caccgaacaa    720
atgcagagag gaaagcgaac gctggatgtt attttggaca cagtttcagc taaacactcg    780
ctcggaccaa tcttggaact gcttaaagtg aatggtactt tagtggttgt gggagcacca    840
gacaagccaa tcgaccttcc ttcatttcca ttaatatttg ggaaaagagc agtgaagggg    900
agcatgacag gggggatgaa agagacacaa gaaatgatgg atgtgtgtgg caaacacaac    960
attacatgtg atatagaagt aattaaacct gatcagataa atgaagccct tgatcgactt   1020
tccaaaaatg atgttcgata cagatttgta atcgacattg ctggaaggtc aagctttaa    1080
```

<210> SEQ ID NO 12
<211> LENGTH: 359
<212> TYPE: PRT
<213> ORGANISM: Corchorus olitorius

<400> SEQUENCE: 12

```
Met Ala Met Glu Thr Pro Asn His Thr Gln Thr Val Ala Gly Trp Ala
1               5                   10                  15

Ala His Asn Ser Ser Gly Lys Ile Val Pro Tyr Thr Phe Lys Arg Arg
            20                  25                  30

Glu Asn Gly Val Asn Asp Val Thr Ile Lys Val Met Tyr Cys Gly Ile
        35                  40                  45

Cys His Thr Asp Leu His His Val Lys Asn Asp Trp Gly Ile Thr Met
    50                  55                  60

Tyr Pro Val Val Pro Gly His Glu Ile Thr Gly Val Ile Thr Lys Ile
65                  70                  75                  80

Gly Asn Asn Val Lys Asn Phe Lys Val Gly Asp Arg Val Gly Val Gly
                85                  90                  95

Cys Leu Ala Ala Ser Cys Leu Glu Cys Glu Phe Cys Lys Ser Ser Gln
            100                 105                 110

Glu Asn Tyr Cys Asp Gln Ile Gln Phe Thr Tyr Asn Gly Ile Phe Trp
        115                 120                 125

Asp Gly Ser Val Thr Tyr Gly Gly Tyr Ser Gln Met Leu Val Ala Asp
    130                 135                 140

His Arg Tyr Val Val Arg Val Pro Asp Asn Leu Pro Met Asp Ala Ala
145                 150                 155                 160

Ala Pro Leu Leu Cys Ala Gly Ile Thr Val Phe Ser Pro Met Lys Asp
                165                 170                 175

Ser Gln Leu Leu Glu Ser Pro Gly Lys Lys Val Gly Ile Val Gly Leu
            180                 185                 190

Gly Gly Leu Gly His Val Ala Val Lys Met Ala Lys Ala Phe Gly His
        195                 200                 205

His Val Thr Val Ile Ser Thr Ser Pro Ser Lys Glu Lys Glu Ala Lys
    210                 215                 220

Gln Arg Leu Gly Ala Asp Asp Phe Ile Val Ser Thr Asn Thr Glu Gln
225                 230                 235                 240

Met Gln Arg Gly Lys Arg Thr Leu Asp Val Ile Leu Asp Thr Val Ser
                245                 250                 255

Ala Lys His Ser Leu Gly Pro Ile Leu Glu Leu Lys Val Asn Gly
            260                 265                 270

Thr Leu Val Val Gly Ala Pro Asp Lys Pro Ile Asp Leu Pro Ser
        275                 280                 285

Phe Pro Leu Ile Phe Gly Lys Arg Ala Val Lys Gly Ser Met Thr Gly
```

```
                   290                     295                     300
Gly Met Lys Glu Thr Gln Glu Met Met Asp Val Cys Gly Lys His Asn
305                     310                     315                     320

Ile Thr Cys Asp Ile Glu Val Ile Lys Pro Asp Gln Ile Asn Glu Ala
                    325                     330                     335

Leu Asp Arg Leu Ser Lys Asn Asp Val Arg Tyr Arg Phe Val Ile Asp
            340                     345                     350

Ile Ala Gly Arg Ser Lys Leu
            355

<210> SEQ ID NO 13
<211> LENGTH: 1071
<212> TYPE: DNA
<213> ORGANISM: Corchorus olitorius

<400> SEQUENCE: 13
atgggcagtc ttgaaactga gagaacaacc acaggctggg ctgccagaga cccttctgga      60
gtcttgtctc cttacactta cactctcaga aacacaggtc cagaagatgt ttttatcaag     120
gttatttgct gtggaatctg ccacactgat cttcatcaag ccaaaaatga tcttggcatg     180
tcaaactacc caatggttcc tgggcatgaa gtggttgggg aggtgttgga agtaggatca     240
caggtgacca aattcagagt aggagagata gttggcgttg ttgtattgt tgggtgttgc      300 agaaactgcc gcccatgcaa cactgacaat gaacaatact gcaacaagaa gatttggtct     360
tacaatgatg tctacactga tggcaaaccc actcaaggtg ctttgctgc tccatggtc      420 gctgatcaaa agtttgtggt gaaaatccct gatggaatgg cagcagaaca ggtggctcca     480
ctcttgtgtg ctggtgtgac agtttacagc ccactgaaac actttggtct aatggagagt     540
gggttaagag gagggatttt ggggcttgga ggagtaggtc acatgggagt gaagatagcc     600
aaagcaatgg gacaccatgt gactgttatc agctcttcag acaagaaaaa agttgaggcc     660
ttggagcatc ttggtgctga tgattatgta gtcagctctg atgctgaaag catgcaaaag     720
attgctgatt cactcgacta tatcatcgat accgtgcctg tttttcatcc ccttgagcct     780
tacctttcag tgttgaaact tgatggaaag ttgatcttga ctggtgttat caatactcct     840
cttcagtttg ttacccccat ggtcatgctt gggagaaagg taattacagg gagtttcgtt     900
gggagcatga ggaaacaga ggagatgctt gatttctgta agagaaagga tttaaactca     960
atgattgaag ttgtgaagat ggattatatc aacacagcca tggagaggct cgagaagaat    1020
gatgttcgct acaggttcgt cgtggatgtt gccggaagca aacttgagta a              1071

<210> SEQ ID NO 14
<211> LENGTH: 356
<212> TYPE: PRT
<213> ORGANISM: Corchorus olitorius

<400> SEQUENCE: 14

Met Gly Ser Leu Glu Thr Glu Arg Thr Thr Gly Trp Ala Ala Arg
1               5                   10                  15

Asp Pro Ser Gly Val Leu Ser Pro Tyr Thr Tyr Thr Leu Arg Asn Thr
                20                  25                  30

Gly Pro Glu Asp Val Phe Ile Lys Val Ile Cys Cys Gly Ile Cys His
            35                  40                  45

Thr Asp Leu His Gln Ala Lys Asn Asp Leu Gly Met Ser Asn Tyr Pro
        50                  55                  60

Met Val Pro Gly His Glu Val Val Gly Glu Val Leu Glu Val Gly Ser
```

-continued

```
             65                  70                  75                  80
        Gln Val Thr Lys Phe Arg Val Gly Glu Ile Val Gly Val Gly Cys Ile
                             85                  90                  95

Val Gly Cys Cys Arg Asn Cys Arg Pro Cys Asn Thr Asp Asn Glu Gln
                        100                 105                 110

Tyr Cys Asn Lys Lys Ile Trp Ser Tyr Asn Asp Val Tyr Thr Asp Gly
                    115                 120                 125

Lys Pro Thr Gln Gly Gly Phe Ala Ala Ser Met Val Ala Asp Gln Lys
                130                 135                 140

Phe Val Val Lys Ile Pro Asp Gly Met Ala Ala Glu Gln Val Ala Pro
        145                 150                 155                 160

Leu Leu Cys Ala Gly Val Thr Val Tyr Ser Pro Leu Lys His Phe Gly
                        165                 170                 175

Leu Met Glu Ser Gly Leu Arg Gly Gly Ile Leu Gly Leu Gly Gly Val
                    180                 185                 190

Gly His Met Gly Val Lys Ile Ala Lys Ala Met Gly His His Val Thr
                195                 200                 205

Val Ile Ser Ser Ser Asp Lys Lys Val Glu Ala Leu Glu His Leu
            210                 215                 220

Gly Ala Asp Asp Tyr Val Val Ser Ser Asp Ala Glu Ser Met Gln Lys
        225                 230                 235                 240

Ile Ala Asp Ser Leu Asp Tyr Ile Ile Asp Thr Val Pro Val Phe His
                        245                 250                 255

Pro Leu Glu Pro Tyr Leu Ser Val Leu Lys Leu Asp Gly Lys Leu Ile
                    260                 265                 270

Leu Thr Gly Val Ile Asn Thr Pro Leu Gln Phe Val Thr Pro Met Val
                275                 280                 285

Met Leu Gly Arg Lys Val Ile Thr Gly Ser Phe Val Gly Ser Met Lys
            290                 295                 300

Glu Thr Glu Glu Met Leu Asp Phe Cys Lys Glu Lys Asp Leu Asn Ser
        305                 310                 315                 320

Met Ile Glu Val Val Lys Met Asp Tyr Ile Asn Thr Ala Met Glu Arg
                        325                 330                 335

Leu Glu Lys Asn Asp Val Arg Tyr Arg Phe Val Val Asp Val Ala Gly
                    340                 345                 350

Ser Lys Leu Glu
                355

<210> SEQ ID NO 15
<211> LENGTH: 2492
<212> TYPE: DNA
<213> ORGANISM: Corchorus olitorius

<400> SEQUENCE: 15
attatcttgg gcatataccc catatttgaa ggcatgggat gtccctccat gaccatctgc      60
ctctaatttc agattcccat caatgtaaac cttcaacttt gctgcatcaa catcatggat     120
aacattcagc ttgaaccact tgtcatagat gtcccgaacc aggaccggac ttttgtagta     180
cgtgagcgaa ccattgtaga cccggagcat tagggtggtg gctcgaggag ggcttgctcc     240
aaaaacttgc atgatgcaaa atcctgatgt tccctggggc acataccagt atccttcaaa     300
ctgccacacc cctgacgagt aattgtatcc atgtatggca atctcggttc ggggcttttgt    360 tttgctagta ggagtatgcg gcttgtctgt ggagtaaacc caacatctat gaacgccctc     420
aatgaagcta taacgctgcg cctcaggcac gttgtagggc ctctggatat ggtagtatgt     480
```

```
tcggttcagg ggaagagaga tgaacccttt cgtaagatca acctgttcgt ccgaagcaaa    540
ggcttgatac aaaagtgtac tgactagaat aattaatatc aagtagaagc aagtcatttt    600
ggttaaggct ggtgacaatt gcatgtatga aaaagtgaa tgttaatgat tgatgggttt      660
aattagtatg ggacattgat ctttgcatat gagtaattaa tatatagaaa tgagaaggaa    720
tttgttaatg attcaatgct tattgtatct gtagagtggc agatgatcat aatagcttaa    780
ttttgatggt ttgattccta gtggaaccat atatatagct ttattaaata gctaggccag    840
aataattttg caaatatca gcaataaaga dacacaataa gataaagatt ctatcgatta     900
acagctcaag aatggacatc agcaagcaaa cagcagcaaa acatttcata tgaagtcatg    960
agtcacgggc ttaaacatag catagcaagg gggaaacaat gtaaaagaca aaagcagtag    1020
ttagaggaac taaagaagca aaatccaata ccatgaatca gattcccagc agataaaaca    1080
actaaatggg catagaagcg agggatcgac gatttatcag ttctttaatt atgctagcgc    1140
gtgatcgatg aactttattc taacatctag actacccagt tgggattcta atatctggac    1200
ttcctagttg aaagtgaacc tagctactct gacaaggaat tgccacatc gatcacaaaa     1260 cggtatctga catcagattt tgcaagcctg tccattgctg tgttaatctc atccatccga    1320
atcagctcaa tgtctgcact aatattgtgc ttggcacaaa agtctagcat ctcttgtgtt    1380
tctttcatcc ctccaatatc acttcctcca acaagcttcc ggcctaaaac taaaggaaag    1440
atgggcaatt caaggggctt attgggcaat cccaaagtga ccagttttcc attcaccttc    1500
agcagactaa gcagtggaag cagggagtga actgcagaca ccgtgtcaat gatatagtcc    1560
atggtgccaa cggccgactt cattttgca ggatcattgg aaagaagaaa tgagtcagca     1620
ccaagtctat taattgcttc ttcttccttc tttggggagc tactaatgac agtaactttc    1680
aacccaaagg ccttaccgat tttcacagca acatgaccaa gcccaccaag tcctgcaact    1740
cccaaatgct tgcctgcctc agtcattcca tagtatttca tagggctgta cactgtgatc    1800
ccggcacata atagtggtgc acccgcatcc agtggcatgt tatcaggaaa ccgaaccaca    1860
aagcgctggt caacaacaat catatctgaa taaccaccat aatttcttgt cccatccaca    1920
taattagagt tataggtaaa tatcatctga gggcaatagt tctccaggtc ctgctggcag    1980
cactcacatt tcttgcagga gccaaccatg accccaaccc caacccggtc tccctctttg    2040
aattttgtca ccttattccc cacttttgtt gcaacaccaa caatttcatg cccaggaaca    2100
acagggtaac gggtgaaacc ccattcattt ctaagggtat gcaggtcgga atggcacact    2160
ccacagtaga gtattttcaa ggtgacatct tcctcaccat tttcccttct ggagaactgg    2220
aaaggagaga gagttccgga ggaatcccga gcagcataac caaaagcctt tgtgggtgc     2280 tcttcttctg gtgattttga catttctttt tcgactctgt tttttgtttt tactttactc    2340 ttttttttgtt ctcttcactg ttgaagaagt ggttcttatt gttttaaggt tgcaaaatct   2400
aacagatggg tataggacaa tttataggag gagatggtgg ttccttagac actgtttacg    2460
tacacccctt gtatacctttt attagttata ga                                 2492
```

<210> SEQ ID NO 16
<211> LENGTH: 744
<212> TYPE: DNA
<213> ORGANISM: Corchorus olitorius

<400> SEQUENCE: 16

```
atggctccaa ctcaggcaga acagcaaact caagctagta ggcaccagga agttggccac    60
```

-continued

```
aagagtctct tgcagagtga taaactctac caatatatac ttgagaccag tgtttatcct    120
agggagcctg aagccatgaa agagctcagg gagcttactg caaaacatcc atggaatctc    180
atgactactt cagctgatga agggcagttt ttgaacatgt tgcttaagct tattaatgcc    240
aagaacacca tggaaattgg tgtttacact ggctattcac tccttgccac tgccttgct     300 ctgcctgaag atggcaagat tttggccatg gacatcaacc gtgaaaacta tgaattgggt    360
ttaccagtaa tccaaaaagc cggtgttgct cacaagattg acttcaaaga aggccctgct    420
cttcctgttc ttgaccaaat gattgaagct gggacatacc atggaacatt cgatttcatc    480
tttgttgatg ctgacaagga caactacatt aactaccaca gaggctgat tgagctagtt     540 aaggttgggg gagtcatcgg ctacgacaac accctatgga acggttccgt ggtggcgcct    600
cccgatgctc cattaaggaa gtatgtcttg tattacagag actttgtctt ggagcttaac    660
aaagccctag ctgctgatcc aaggattgaa atctgccaac ttcctgttgg cgatggaatt    720
accctctgcc gtcggattaa gtga                                           744
```

<210> SEQ ID NO 17
<211> LENGTH: 247
<212> TYPE: PRT
<213> ORGANISM: Corchorus olitorius

<400> SEQUENCE: 17

```
Met Ala Pro Thr Gln Ala Glu Gln Gln Thr Gln Ala Ser Arg His Gln
1               5                   10                  15

Glu Val Gly His Lys Ser Leu Leu Gln Ser Asp Lys Leu Tyr Gln Tyr
            20                  25                  30

Ile Leu Glu Thr Ser Val Tyr Pro Arg Glu Pro Glu Ala Met Lys Glu
        35                  40                  45

Leu Arg Glu Leu Thr Ala Lys His Pro Trp Asn Leu Met Thr Thr Ser
    50                  55                  60

Ala Asp Glu Gly Gln Phe Leu Asn Met Leu Leu Lys Leu Ile Asn Ala
65                  70                  75                  80

Lys Asn Thr Met Glu Ile Gly Val Tyr Thr Gly Tyr Ser Leu Leu Ala
                85                  90                  95

Thr Ala Leu Ala Leu Pro Glu Asp Gly Lys Ile Leu Ala Met Asp Ile
            100                 105                 110

Asn Arg Glu Asn Tyr Glu Leu Gly Leu Pro Val Ile Gln Lys Ala Gly
        115                 120                 125

Val Ala His Lys Ile Asp Phe Lys Glu Gly Pro Ala Leu Pro Val Leu
    130                 135                 140

Asp Gln Met Ile Glu Ala Gly Thr Tyr His Gly Thr Phe Asp Phe Ile
145                 150                 155                 160

Phe Val Asp Ala Asp Lys Asp Asn Tyr Ile Asn Tyr His Lys Arg Leu
                165                 170                 175

Ile Glu Leu Val Lys Val Gly Gly Val Ile Gly Tyr Asp Asn Thr Leu
            180                 185                 190

Trp Asn Gly Ser Val Val Ala Pro Pro Asp Ala Pro Leu Arg Lys Tyr
        195                 200                 205

Val Leu Tyr Tyr Arg Asp Phe Val Leu Glu Leu Asn Lys Ala Leu Ala
    210                 215                 220

Ala Asp Pro Arg Ile Glu Ile Cys Gln Leu Pro Val Gly Asp Gly Ile
225                 230                 235                 240

Thr Leu Cys Arg Arg Ile Lys
                245
```

<210> SEQ ID NO 18
<211> LENGTH: 744
<212> TYPE: DNA
<213> ORGANISM: Corchorus olitorius

<400> SEQUENCE: 18

```
atggcaacca ataccccaaga gcagcaaact caggctggca gacaccagga ggttggccac    60
aagagtcttt tgcaaagtga tgctctttac cagtatatcc ttgagacaag tgtgtatcca   120
agagagcctg aacccatgaa ggagctcagg gaattgactg ccaagcatcc atggaatctg   180
atgacaacat cagcagatga agggcaattc ctgaacatgc ttctgaagct gatcaatgcc   240
aagaacacca tggaaattgg tgtttacact ggctactctc tcttagccac agcccttgct   300
cttcctgacg atggcaagat cttggccatg gacattaaca gggaaaacta cgagttgggt   360
ctgcctgtaa tccaaaaagc aggcgttgca cacaaaattg aattcaaaga gggccctgct   420
ttgcctgttc ttgacaaact agtcgaagat gaaaagaatc atggatcata tgacttcatc   480
ttcgtggatg ctgacaaaga caactacata aactaccaca gaggttaat agaccttgtg    540
aaagttggag gcttaatcgg ctacgacaac actctatgga atggctctgt tgtcgcccca   600
cctgatgctc ctctcaggaa atatgtcagg tattacagag actttgtttt ggaactcaac   660
aaggctctcg ccgccgaccc caggattgag atctgtatgc ttcccgtcgg cgatggaatc   720
acccttttgcc gtcgaatcaa atga                                          744
```

<210> SEQ ID NO 19
<211> LENGTH: 247
<212> TYPE: PRT
<213> ORGANISM: Corchorus olitorius

<400> SEQUENCE: 19

Met Ala Thr Asn Thr Gln Glu Gln Gln Thr Gln Ala Gly Arg His Gln
1               5                   10                  15

Glu Val Gly His Lys Ser Leu Leu Gln Ser Asp Ala Leu Tyr Gln Tyr
            20                  25                  30

Ile Leu Glu Thr Ser Val Tyr Pro Arg Glu Pro Glu Pro Met Lys Glu
        35                  40                  45

Leu Arg Glu Leu Thr Ala Lys His Pro Trp Asn Leu Met Thr Thr Ser
    50                  55                  60

Ala Asp Glu Gly Gln Phe Leu Asn Met Leu Leu Lys Leu Ile Asn Ala
65                  70                  75                  80

Lys Asn Thr Met Glu Ile Gly Val Tyr Thr Gly Tyr Ser Leu Leu Ala
                85                  90                  95

Thr Ala Leu Ala Leu Pro Asp Asp Gly Lys Ile Leu Ala Met Asp Ile
            100                 105                 110

Asn Arg Glu Asn Tyr Glu Leu Gly Leu Pro Val Ile Gln Lys Ala Gly
        115                 120                 125

Val Ala His Lys Ile Glu Phe Lys Glu Gly Pro Ala Leu Pro Val Leu
    130                 135                 140

Asp Lys Leu Val Glu Asp Glu Lys Asn His Gly Ser Tyr Asp Phe Ile
145                 150                 155                 160

Phe Val Asp Ala Asp Lys Asp Asn Tyr Ile Asn Tyr His Lys Arg Leu
                165                 170                 175

Ile Asp Leu Val Lys Val Gly Gly Leu Ile Gly Tyr Asp Asn Thr Leu
            180                 185                 190

Trp Asn Gly Ser Val Val Ala Pro Pro Asp Ala Pro Leu Arg Lys Tyr
        195                 200                 205

Val Arg Tyr Tyr Arg Asp Phe Val Leu Glu Leu Asn Lys Ala Leu Ala
    210                 215                 220

Ala Asp Pro Arg Ile Glu Ile Cys Met Leu Pro Val Gly Asp Gly Ile
225                 230                 235                 240

Thr Leu Cys Arg Arg Ile Lys
                245

<210> SEQ ID NO 20
<211> LENGTH: 1098
<212> TYPE: DNA
<213> ORGANISM: Corchorus olitorius

<400> SEQUENCE: 20

```
atgggttcaa ctggtgaaac ccaattcact ccaactcaag tctccgatga ggaagcaaac    60
ttgttcgcca tgcaattggc tagtgcctca gttcttccca tggtcctcaa atctgccata   120
gaacttgacc tacttgaagt catggccaag gctggacctg gtgctttctt gtccccaaca   180
gaagtagctt cccaattgcc caccaagaac cctgatgcac ccgtcatgct cgaccgtatc   240
ttgcggctcc ttgctagtta ctccatttta acttgctcct taaggaatct tcctgatggc   300
aaagttgaga ggctctatgg ccttggccct gtctgtaaat acctggtcaa gaatgaagat   360
ggtgtcgctc tttccgccct taatctcatg aatcaagaca aggtcctaat ggagagctgg   420
tactacttga agatgcagt gttggaaggt ggaattccat caacaaggc ctatggcatg    480
accgcgttcg agtaccatgg cactgaccct agattcaaca aggttttcaa caggggaatg   540
tctgatcact caactatcac catgaagaag attctcgaga cctacgatgg attcgagggg   600
ctcaaaacat tggttgacgt tggtggtggt gttggtgcca cgcttaacat gatcgtctcc   660
aagcacccctt ccattaaggg cattaacttt gatttgcctc atgtcattga ggatgctcca   720
gctcttcctg tgttgagca tgttggtgga gatatgtttg taagtgttcc aaaaggagat   780
gccattttca tgaagtggat atgtcatgat ggagcgatg aacactgcgt aaaattcttg    840
aagaagtgct atgaagcttt gccagacaat gggaaagtca tcgttgccga atgcattctt   900
cctgattacc cagatgctag ccttgccaca aagctagttg ttcatatcga ttgtatcatg   960
ttggctcaca cccctggtgg gaaagaaagg acagagaagg aatttgaagc cttggcaaag  1020
ggggcaggtt ttcaaggttt ccaagtaaag tgttgtgctt ttggcactta catcatggag  1080
ttcctcaaaa ctgtttaa                                                1098
```

<210> SEQ ID NO 21
<211> LENGTH: 365
<212> TYPE: PRT
<213> ORGANISM: Corchorus olitorius

<400> SEQUENCE: 21

Met Gly Ser Thr Gly Glu Thr Gln Phe Thr Pro Thr Gln Val Ser Asp
1               5                   10                  15

Glu Glu Ala Asn Leu Phe Ala Met Gln Leu Ala Ser Ala Ser Val Leu
            20                  25                  30

Pro Met Val Leu Lys Ser Ala Ile Glu Leu Asp Leu Leu Glu Val Met
        35                  40                  45

Ala Lys Ala Gly Pro Gly Ala Phe Leu Ser Pro Thr Glu Val Ala Ser
    50                  55                  60

Gln Leu Pro Thr Lys Asn Pro Asp Ala Pro Val Met Leu Asp Arg Ile

```
            65                  70                  75                  80
Leu Arg Leu Leu Ala Ser Tyr Ser Ile Leu Thr Cys Ser Leu Arg Asn
                    85                  90                  95
Leu Pro Asp Gly Lys Val Glu Arg Leu Tyr Gly Leu Gly Pro Val Cys
                   100                 105                 110
Lys Tyr Leu Val Lys Asn Glu Asp Gly Val Ala Leu Ser Ala Leu Asn
               115                 120                 125
Leu Met Asn Gln Asp Lys Val Leu Met Glu Ser Trp Tyr Tyr Leu Lys
           130                 135                 140
Asp Ala Val Leu Glu Gly Gly Ile Pro Phe Asn Lys Ala Tyr Gly Met
145                 150                 155                 160
Thr Ala Phe Glu Tyr His Gly Thr Asp Pro Arg Phe Asn Lys Val Phe
                    165                 170                 175
Asn Arg Gly Met Ser Asp His Ser Thr Ile Thr Met Lys Lys Ile Leu
                180                 185                 190
Glu Thr Tyr Asp Gly Phe Glu Gly Leu Lys Thr Leu Val Asp Val Gly
            195                 200                 205
Gly Gly Val Gly Ala Thr Leu Asn Met Ile Val Ser Lys His Pro Ser
       210                  215                  220
Ile Lys Gly Ile Asn Phe Asp Leu Pro His Val Ile Glu Asp Ala Pro
225                 230                 235                 240
Ala Leu Pro Gly Val Glu His Val Gly Gly Asp Met Phe Val Ser Val
                    245                 250                 255
Pro Lys Gly Asp Ala Ile Phe Met Lys Trp Ile Cys His Asp Trp Ser
                260                 265                 270
Asp Glu His Cys Val Lys Phe Leu Lys Cys Tyr Glu Ala Leu Pro
            275                 280                 285
Asp Asn Gly Lys Val Ile Val Ala Glu Cys Ile Leu Pro Asp Tyr Pro
        290                 295                 300
Asp Ala Ser Leu Ala Thr Lys Leu Val Val His Ile Asp Cys Ile Met
305                 310                 315                 320
Leu Ala His Asn Pro Gly Gly Lys Glu Arg Thr Glu Lys Glu Phe Glu
                    325                 330                 335
Ala Leu Ala Lys Gly Ala Gly Phe Gln Gly Phe Gln Val Lys Cys Cys
                340                 345                 350
Ala Phe Gly Thr Tyr Ile Met Glu Phe Leu Lys Thr Val
            355                 360                 365

<210> SEQ ID NO 22
<211> LENGTH: 1635
<212> TYPE: DNA
<213> ORGANISM: Corchorus olitorius

<400> SEQUENCE: 22
atggcacccc aagcaccaga attgccacaa gaagatatca tttttcgatc aaaacttcct        60
gatatctata ttcctaagca tcttccttta cattcatatt gcttcgagaa catttcgaag       120
gttgcttcta agccttgttt gatcaatggg acgacgggtc agatttatac ttacgaagaa       180
gttgaactca cagctcgccg agtcgccgct gggcttcaca aactcggcgt tcaacaacgt       240
caagttataa tgcttttatt acccaatact cccgagtttg tcctgtcttt cctcggcgct       300
tcattcctcg cgccgttttg cacggcggcg aacccgtttt tcaccgcccc ggaggttgcc       360
aagcaagcca agcttccaa cgccaggatc ataatcactc aagcttcgta cgtcgacaaa        420
gtgaaggaat cgcccagga aaatgatgtc aaggtcatgt gcattgactc agctccggaa        480
```

```
ggatgtttac atttctccga gttaactcaa gctgacgaga acgatctccc ggaagtcgaa    540
atcaatcccg acgatgtcgt ggcacttcct tattcgtcgg gaaccaccgg gctcccaaaa    600
ggtgtgatgt taactcacaa aggtttggtt accagcgtgg ctcaacaggt cgacggtgaa    660
aacccaaatt tgtacttcca cagcgatgac gtcatcttat gtactctgcc catgttccat    720
atctatgccc tgaactcgat catgctttgc gggcttcggg ccggagctgc gattttgatc    780
atgcagaagt ttgacatcgg attattgttg gatttgattc agaaatacaa aattacgatt    840
gctccgatgg tgccacccat agttttggct attgccaagt catcggaaac tgaaaaatac    900
gacttgtctt cgataaggat ggtgaaatcc ggcgccgcgc cgttgggtaa agagctggaa    960
gatgctgtga gagccaagtt tcctggtgcc aaactcggtc agggatatgg gatgacagaa   1020
gcaggaccag ttctagcaat gtgcttggga tttgccaagg aaccatttga aatcaaatcc   1080
ggtgcctgtg gacggtggt tagaaatgca gagatgaaaa tcgttgaccc agacaccggt   1140
gcctcacttc caagaaacca ggctggagag atttgcatta gaggggatca gatcatgaaa   1200
ggttacctaa atgacccaga ggccacagct aggaccattg acaaagatgg ctggttacat   1260
accggtgata tcggttacat tgatgacgac atgaactct tcatcgttga tcgtttgaag   1320
gaattgatca aatataaggg tttccaggtt gctcctgctg agcttgaagc tatgcttatt   1380
gcccaccctg agattattga tgctgctgtc gtcgcaatga aggatgaggt agctggagaa   1440
gttcctgttg catttgttgt gaaatcagag aaatcaggaa tcactgagga tgaaatcaag   1500
caatatattt caaagcaggt tgtgttctac aagagaataa gccgtgtgtt cttcatggaa   1560
tcaattccaa aggcaccatc aggcaagatt ttgagaaagg aattgagagc taaattggct   1620 tctggaaaact actga                                                    1635
```

<210> SEQ ID NO 23
<211> LENGTH: 544
<212> TYPE: PRT
<213> ORGANISM: Corchorus olitorius

<400> SEQUENCE: 23

```
Met Ala Pro Gln Ala Pro Glu Leu Pro Gln Glu Asp Ile Ile Phe Arg
1               5                   10                  15

Ser Lys Leu Pro Asp Ile Tyr Ile Pro Lys His Leu Pro Leu His Ser
            20                  25                  30

Tyr Cys Phe Glu Asn Ile Ser Lys Val Ala Ser Lys Pro Cys Leu Ile
        35                  40                  45

Asn Gly Thr Thr Gly Gln Ile Tyr Thr Tyr Glu Glu Val Glu Leu Thr
    50                  55                  60

Ala Arg Arg Val Ala Ala Gly Leu His Lys Leu Gly Val Gln Gln Arg
65                  70                  75                  80

Gln Val Ile Met Leu Leu Pro Asn Thr Pro Glu Phe Val Leu Ser
                85                  90                  95

Phe Leu Gly Ala Ser Phe Leu Gly Ala Val Cys Thr Ala Ala Asn Pro
            100                 105                 110

Phe Phe Thr Ala Pro Glu Val Ala Lys Gln Ala Lys Ala Ser Asn Ala
        115                 120                 125

Arg Ile Ile Ile Thr Gln Ala Ser Tyr Val Asp Lys Val Lys Glu Phe
    130                 135                 140

Ala Gln Glu Asn Asp Val Lys Val Met Cys Ile Asp Ser Ala Pro Glu
145                 150                 155                 160
```

Gly Cys Leu His Phe Ser Glu Leu Thr Gln Ala Asp Glu Asn Asp Leu
            165                 170                 175

Pro Glu Val Glu Ile Asn Pro Asp Asp Val Val Ala Leu Pro Tyr Ser
        180                 185                 190

Ser Gly Thr Thr Gly Leu Pro Lys Gly Val Met Leu Thr His Lys Gly
        195                 200                 205

Leu Val Thr Ser Val Ala Gln Gln Val Asp Gly Glu Asn Pro Asn Leu
    210                 215                 220

Tyr Phe His Ser Asp Asp Val Ile Leu Cys Thr Leu Pro Met Phe His
225                 230                 235                 240

Ile Tyr Ala Leu Asn Ser Ile Met Leu Cys Gly Leu Arg Ala Gly Ala
                245                 250                 255

Ala Ile Leu Ile Met Gln Lys Phe Asp Ile Gly Leu Leu Leu Asp Leu
            260                 265                 270

Ile Gln Lys Tyr Lys Ile Thr Ile Ala Pro Met Val Pro Pro Ile Val
        275                 280                 285

Leu Ala Ile Ala Lys Ser Ser Glu Thr Glu Lys Tyr Asp Leu Ser Ser
    290                 295                 300

Ile Arg Met Val Lys Ser Gly Ala Ala Pro Leu Gly Lys Glu Leu Glu
305                 310                 315                 320

Asp Ala Val Arg Ala Lys Phe Pro Gly Ala Lys Leu Gly Gln Gly Tyr
                325                 330                 335

Gly Met Thr Glu Ala Gly Pro Val Leu Ala Met Cys Leu Gly Phe Ala
            340                 345                 350

Lys Glu Pro Phe Glu Ile Lys Ser Gly Ala Cys Gly Thr Val Val Arg
        355                 360                 365

Asn Ala Glu Met Lys Ile Val Asp Pro Asp Thr Gly Ala Ser Leu Pro
    370                 375                 380

Arg Asn Gln Ala Gly Glu Ile Cys Ile Arg Gly Asp Gln Ile Met Lys
385                 390                 395                 400

Gly Tyr Leu Asn Asp Pro Glu Ala Thr Ala Arg Thr Ile Asp Lys Asp
                405                 410                 415

Gly Trp Leu His Thr Gly Asp Ile Gly Tyr Ile Asp Asp Asp Glu
            420                 425                 430

Leu Phe Ile Val Asp Arg Leu Lys Glu Leu Ile Lys Tyr Lys Gly Phe
        435                 440                 445

Gln Val Ala Pro Ala Glu Leu Glu Ala Met Leu Ile Ala His Pro Glu
    450                 455                 460

Ile Ile Asp Ala Ala Val Val Ala Met Lys Asp Glu Val Ala Gly Glu
465                 470                 475                 480

Val Pro Val Ala Phe Val Val Lys Ser Glu Lys Ser Gly Ile Thr Glu
                485                 490                 495

Asp Glu Ile Lys Gln Tyr Ile Ser Lys Gln Val Val Phe Tyr Lys Arg
            500                 505                 510

Ile Ser Arg Val Phe Phe Met Glu Ser Ile Pro Lys Ala Pro Ser Gly
        515                 520                 525

Lys Ile Leu Arg Lys Glu Leu Arg Ala Lys Leu Ala Ser Gly Asn Tyr
    530                 535                 540

<210> SEQ ID NO 24
<211> LENGTH: 964
<212> TYPE: DNA
<213> ORGANISM: Corchorus olitorius

<400> SEQUENCE: 24

```
tgtgttaggg atatgggctg actgagactg gaggaggagc gactagggtg atagggcctg    60
aggagtcagc acggtatggg acggtcggtc gccttgcaga aaatatggaa gccaagatag   120
ttgaccctga aactggagag gccctgcctc ctgggcagag aggggaatta tggttgcgag   180
ggccaacagt aatgaagggt tatataggag atgagaaggc aactgctgaa accttggatt   240
cagaaggctg gttaaaaact ggtgatatat gttattttga ctctgagggg tttctctata   300
ttgtagatag attgaaggaa ttgatcaaat acaaggcata tcaggttcct cccgctgaat   360
tggaacagtt acttcattcc catcctaaaa ttgccgatgc agctgtgatt ccgtaccctg   420
atgaagaagc agggcagatt cccatggcct atgttgtaag aaatgccgga agtagcatca   480
ccgaggcaga agtcatggat ttcgttgcaa acaggttgc accatacaag aagatccgac    540
gtgttgcttt tatcgattct attccaaaat ctccggcagg aaagatctta aggagggagc   600
tgattaaaca ttctctttcc agtggtttat caaagttata caatctgga acatacaaca    660 gtcaacagag gagtttgccg actgctgaga agacctctt agtgaacatg aaaacctact    720
tggccatctg ctgaaggctt tgattccact gttggttatt gttacagttc aaaaacttca   780
gattgaaagt aaattctttt tagattttag acagcttggg attctaaatg agttccctta   840
ctggcggcat tgatcaccat agcaacagaa caataactaa attgtatact atttgtgttt   900
caagttttca ggggaaaaaa gaaattagtt gagtgttgtt gaacatgaca tgagatgagg   960
gaca                                                                964

<210> SEQ ID NO 25
<211> LENGTH: 1154
<212> TYPE: DNA
<213> ORGANISM: Corchorus olitorius

<400> SEQUENCE: 25
tctcggactt aaaatgttct tccacccctta caggtttgag tttaaacccc aagtcaagaa   60
tggtttcagc cttcaatatt ccctcttatt tcaagaatac aacagaacaa ttttcatgac   120
aagcaaagga ccaaggggag gaatagtaag aaaggacata tttttaagca taaggactac   180
caataagtaa taacatggtg attttttagta gtaacatttt tgactcacta cattaattaa   240
ttagcaaact acaatatcat catgattata aatccaaata aaaatctaca aatactagaa   300
ggaagaaatg aaaatttcaa ggcagggtag cagattgagc agccagctta gctctgagat   360
cttttctcaa tatctttcct gaaggagact tgggaattgc atgaacaaag taaatcttat   420
gcaatctctt gtagaaaacc acctgttttg caatgaattc tttgacagct tcttcagtaa   480
gttcaaaacc atttgatcta accacaaatg caacaggaac ttccccagca acttcatctt   540
tttgcggaac tacagctgca tctgcaattg atggatggct tacaaggaga gattcaagct   600
cagctggtgg cacttggaag cctttgaatt tgatgatttc ctttacccta tcaacaatga   660
aaatctcatc atcttcatca acataaccaa tgtcacctgt atgaagccaa ccctccacat   720
ctatggtggc tgctgtggcc gcgacatcat tcaaataacc taaaatttgt tcattagaaa   780
tgttgaacaa atcaggattg acagaatttc ttttatcaga tcaaacagtt ttaaagatgt   840
ataattagtt aaccttcat gatttgggat ccgcgaatgc aaatttcgcc aggttgattg    900
tagccgaggg agcagccggt ttcagggtca atgaccttaa gctcagcatt tctaaccaca   960
gtgccacatg aaccagactt ggttggaaag ggttgcttag caaatcctag gcacattgat  1020
agaactggtc cagcttctgt catcccatat ccctatattt gtgtggaaat gacatagtta  1080
```

```
atgcattgta aaaggtagag tgtgtaacac tacatggtat gattctatat aaatgtaata   1140
tggacagaca taac                                                     1154

<210> SEQ ID NO 26
<211> LENGTH: 1644
<212> TYPE: DNA
<213> ORGANISM: Corchorus olitorius

<400> SEQUENCE: 26
atggagaaat ctgggtatgg aagagatggg atttacaggt ctctaaggcc acctgtaatt     60
cttcccaagg atccaaatct ttccatgatt tcatttctgt ttagaaacat ttcttcttac    120
cctcaccatc cagccctcat tgatgctgat tccaatgaaa ttctaacttt ttctcagttc    180
aaatccactg tcatcaagct ttcccatgct tttctcaatc tgggtatcaa caaaaaagac    240
cgtgtcttga ttttgcacc aaattcgatc caattccctc tctgtttctt cgctgtaacc    300
gccattggcg ctattgctac aaccgccaac cccatttaca ctgtcaatga actctcgaaa    360
caaatcaaag attcgactcc caagcttctt gttactgttc ctgaattgtt cgacaaagtt    420
aaggatttca gcttcctgt tatattgctt ggtcctaaac agaacaaacc cccatctcca    480
tctgatgtaa aaaatgtccc aaaaatctta tcttttcatg accttctcga tttagcgggg    540
agcgtgacag agcttcccgc ggtttctgtt aagcaaactg atacggcgtc acttttatac    600
tcctccggca cgacagggt aagtaaaggt gttgttttga cgcataggaa tttcattgca    660
gcggctttga tgataaccaa ggaccaagaa cttgccggcg ataagcaccg gttttcttg    720 tgtgttttgc ccttgttcca tgtctttgga ttggcggtta ttgcgttttc acagctgcag    780
ataggaaaca ctttggtttc tatggcaaag ttcgattttg ggttgttttt gaagaatgca    840
gagaagtata aagccaccca tttgtgggtt gtgccgccaa ttgtgcttgc catggctaag    900
cagagtgtgg ttaagaagtt tgatctttcc tcagtgaggc aaattggctc tggcgctgct    960
cctcttggga aggatttgat ggaggaatgt gcaaaaaatt ttcctcaggc tgtggttatg   1020
caggggtttg gaatgactga acttgtggc attgtctcag tggagaatcc tacagttggt   1080
gtccgacata ctggttcagc tggaatgctt gtttcaagca ttgaagctca ataatcagt   1140 actgagagtc taaagcctct tcctcccaat caattagggg aaatatgggt tcgagggcct   1200
aatatgatgc aaggttacta caacaatcca gaggcaacaa actaacaat agataaaaag   1260 ggttgggtac atacaggaga tcttggatac tttgatgaag atgggaatct ttatgttgtt   1320
gaccgaatta aagagttgat caaatataaa ggattccaga ttgcaccagc cgaacttgaa   1380
ggactacttg tatctcatcc tgaaatattg gatgctgttg tcatcccgta tcctgacgct   1440
gaagctggtg aggttccggt tgcatatgtt gttcgctccc ctaacagctc actgactgag   1500
gaggatgtcc aaaatttat agctaaacag gtggcaccgt tcaaaagact aaggagagtt   1560
acattcataa cgagtgtccc aaagtcggct tcaggaaaaa tcctgaggag agagcttata   1620
gcggaagtaa gatccaagat gtga                                          1644

<210> SEQ ID NO 27
<211> LENGTH: 547
<212> TYPE: PRT
<213> ORGANISM: Corchorus olitorius

<400> SEQUENCE: 27

Met Glu Lys Ser Gly Tyr Gly Arg Asp Gly Ile Tyr Arg Ser Leu Arg
1               5                   10                  15
```

```
Pro Pro Val Ile Leu Pro Lys Asp Pro Asn Leu Ser Met Ile Ser Phe
            20                  25                  30

Leu Phe Arg Asn Ile Ser Ser Tyr Pro His His Pro Ala Leu Ile Asp
        35                  40                  45

Ala Asp Ser Asn Glu Ile Leu Thr Phe Ser Gln Phe Lys Ser Thr Val
    50                  55                  60

Ile Lys Leu Ser His Ala Phe Leu Asn Leu Gly Ile Asn Lys Lys Asp
65                  70                  75                  80

Arg Val Leu Ile Phe Ala Pro Asn Ser Ile Gln Phe Pro Leu Cys Phe
                85                  90                  95

Phe Ala Val Thr Ala Ile Gly Ala Ile Ala Thr Thr Ala Asn Pro Ile
            100                 105                 110

Tyr Thr Val Asn Glu Leu Ser Lys Gln Ile Lys Asp Ser Thr Pro Lys
        115                 120                 125

Leu Leu Val Thr Val Pro Glu Leu Phe Asp Lys Val Lys Asp Phe Lys
    130                 135                 140

Leu Pro Val Ile Leu Leu Gly Pro Lys Gln Asn Lys Pro Pro Ser Pro
145                 150                 155                 160

Ser Asp Val Lys Asn Val Pro Lys Ile Leu Ser Phe His Asp Leu Leu
                165                 170                 175

Asp Leu Ala Gly Ser Val Thr Glu Leu Pro Ala Val Ser Val Lys Gln
            180                 185                 190

Thr Asp Thr Ala Ser Leu Leu Tyr Ser Ser Gly Thr Thr Gly Val Ser
        195                 200                 205

Lys Gly Val Val Leu Thr His Arg Asn Phe Ile Ala Ala Ala Leu Met
210                 215                 220

Ile Thr Lys Asp Gln Glu Leu Ala Gly Asp Lys His Arg Val Phe Leu
225                 230                 235                 240

Cys Val Leu Pro Leu Phe His Val Phe Gly Leu Ala Val Ile Ala Phe
                245                 250                 255

Ser Gln Leu Gln Ile Gly Asn Thr Leu Val Ser Met Ala Lys Phe Asp
            260                 265                 270

Phe Gly Leu Phe Leu Lys Asn Ala Glu Lys Tyr Lys Ala Thr His Leu
        275                 280                 285

Trp Val Val Pro Pro Ile Val Leu Ala Met Ala Lys Gln Ser Val Val
    290                 295                 300

Lys Lys Phe Asp Leu Ser Ser Val Arg Gln Ile Gly Ser Gly Ala Ala
305                 310                 315                 320

Pro Leu Gly Lys Asp Leu Met Glu Glu Cys Ala Lys Asn Phe Pro Gln
                325                 330                 335

Ala Val Val Met Gln Gly Phe Gly Met Thr Glu Thr Cys Gly Ile Val
            340                 345                 350

Ser Val Glu Asn Pro Thr Val Gly Val Arg His Thr Gly Ser Ala Gly
        355                 360                 365

Met Leu Val Ser Ser Ile Glu Ala Gln Ile Ile Ser Thr Glu Ser Leu
    370                 375                 380

Lys Pro Leu Pro Pro Asn Gln Leu Gly Glu Ile Trp Val Arg Gly Pro
385                 390                 395                 400

Asn Met Met Gln Gly Tyr Tyr Asn Asn Pro Glu Ala Thr Lys Leu Thr
                405                 410                 415

Ile Asp Lys Lys Gly Trp Val His Thr Gly Asp Leu Gly Tyr Phe Asp
            420                 425                 430

Glu Asp Gly Asn Leu Tyr Val Val Asp Arg Ile Lys Glu Leu Ile Lys
```

```
                435                 440                 445
Tyr Lys Gly Phe Gln Ile Ala Pro Ala Glu Leu Glu Gly Leu Leu Val
    450                 455                 460

Ser His Pro Glu Ile Leu Asp Ala Val Val Ile Pro Tyr Pro Asp Ala
465                 470                 475                 480

Glu Ala Gly Glu Val Pro Val Ala Tyr Val Val Arg Ser Pro Asn Ser
                485                 490                 495

Ser Leu Thr Glu Glu Asp Val Gln Asn Phe Ile Ala Lys Gln Val Ala
            500                 505                 510

Pro Phe Lys Arg Leu Arg Arg Val Thr Phe Ile Thr Ser Val Pro Lys
        515                 520                 525

Ser Ala Ser Gly Lys Ile Leu Arg Arg Glu Leu Ile Ala Glu Val Arg
    530                 535                 540

Ser Lys Met
545

<210> SEQ ID NO 28
<211> LENGTH: 1089
<212> TYPE: DNA
<213> ORGANISM: Corchorus olitorius

<400> SEQUENCE: 28
tccaacacca acggcggcac caccgccgcc acggacacct tatgcctctg tatcaattcc      60
aacaacgccc ctatctcaaa tttctgcatc agcaaaaccg cagcccctgc tctcaaggaa     120
cacaaaagca cgctgttgag tgagtaaatg tgaaacaatg gcaaaacgca taacacaacg     180
tcgtcgtttt tcaggtaaag attggggttc tctccatcta cttgctgcgc tacgctcgtg     240
atcaagcttt tgtgggtcaa aacgactcct ttgggtaacc ctgttgttcc tgaagagaat     300
ggtaaagcaa cagggtcatc agggtcaatg gaaacttcgg ggatatcgtt tcatttccc     360 tctgataaca ccgtgaaatg caagcagttt tctgggggat catcgatggt tacaactttg     420
aaatcttggc caatttttagg gaagttttgg ttttgggtcg tctcatcctt aagcttgtcg     480
acatattggg attgcgtgat aataatctta gcccgagcag cttttgaattg tttgaagatt     540 tcgtttgatg tgtaaaaagg gttggcagtt gtggaaactg ctccaatcat ggaagctccc     600
atgaaagaga agacgaattc agcacagttt gggaggagaa tcatgatgac atcgcccttc     660
tcgatgccta aatttgacaa accagcggct gtctttcgag aaatcaagtg agtttcagag     720
aaagtgtagg ttttggcaga ggatattcca gagatcaaac atggcttgtc agggaaagag     780
gagagttttt caaagcagta agtatggaga gggaggtgat tggagatggg aatgtcaggc     840
aatttggacc tgaaaatgtg atgattagtt tgaggggaag gttttggtgt tgtcgaaagc     900
tctgctgcag gcttttgtgg ttcaacagga tgatcagcta tggagatcat ggtggtaatt     960
tggtttgatg agtacttgtt gggattttg ggttagaggg aaagtgaatg aaaggaaaga     1020
aaagagaaat aaatataagg taataagaag tggcaagcaa gggccaagga gaggtaggtg     1080
gaagaggaa                                                               1089

<210> SEQ ID NO 29
<211> LENGTH: 1689
<212> TYPE: DNA
<213> ORGANISM: Corchorus olitorius

<400> SEQUENCE: 29
atggcaacga gcttgaactc ccatttcagc ttcccaacct ccgaatccaa acaactcgt      60
```

```
tttcctgact ggtattcacc ggaaacagga atctatacca gcaagcatgc ctccgtatcc    120
atccccacta atccatatct tgatgttgtt tccttcattt tctctcacca acatcaaggg    180
gtcactgctt tcattgattc ctcatctggg ttttcaatat cttactcaaa gctcttacct    240
ttggtccaat ctatggcttc tggtctccac cacctgggtg tttccaaagg tgacgtggtc    300
ttgcttttgt tgccaaattc tcttcactat cctattattt tcttcagtgt tttatattta    360
ggcgcaatcg ttaccctat gaatccactg agtagcattt ccgagatcaa gaaacagatt    420
gctgattcta atgtgcgttt cgctttcact cttcttgaaa cggttgacaa actggagaag    480
ttgggtgttc atgcaattgg ggtaccggaa acatgaact tggattcaga aaaggttgat    540
tttttacctt tttataagct tatggcgggg caatctggta ataaggcccc aaggccagtg    600
attaagcagc aagacactgc ggcgataatg tattcatcgg gaactacagg aacgagtaag    660
ggagttgtat taacacatgg gaatttcata gcaatgattg agcttttttgt aaaatttgaa    720 gcttcacagt atgaatatcc aggttcagag attgtatatt tagctgctct accaatgttc    780
catatatatg ggctatcact gtttgtggtt ggattgttat cgttggggtc tacagttgtt    840
gtcatgagga aatttaatgc tggtgaattg gtaaaagtaa ttgataagtt tgggatcacc    900
cactttccag ttgttccacc tatactcaca gcattgacaa taagcgccaa gggtgtttgt    960
gaaaataact tcaagagctt gaaacaggtt tcttgcggtg ctgctcctat aagcaggaaa    1020
tccatagagg attttgttca ggctttccct catgttgatt tcattcaggg ctatgggatg    1080
acagaatcaa ctgcagtagg aactcggggc ttcaacaccg gaaaacatca taaatattct    1140
tcaataggac ttctagcacc aaacatgcaa gctaaagtgg tggatctgaa ttctggttct    1200
tctatgcctc ctggtgatta cggcgagctt tggttaagag gacctgcaat tatgcaacga    1260
tacttgaata tgttgaagc caccctgatg tcaatccaca gagatggttg gctacgtact    1320
ggtgacattg cttgttttga tgaagatggc tatatgtatt tatctgaccg cttaaaagag    1380
attataaagt acaaaggcta tcagatagct cctgccgatt tagaggccat attaattacc    1440
catcctgaga tacttgacgc tgctgtaact ggagccagtg atgaagcatg tggtgagatt    1500
cctgtggcat ttgtggtgag gaggcatggt tgcacactga cccatggcgc tgtcatggac    1560
ttcgtggcta agcaggttgc acccttataag aaagtaagaa aggtggtgtt tcaaaattca    1620
ataccgaggt ctgctgcagg aaagatcctc cgaagagaac tcaagaagtt cttatgttca    1680
aggctttaa                                                             1689
```

<210> SEQ ID NO 30
<211> LENGTH: 562
<212> TYPE: PRT
<213> ORGANISM: Corchorus olitorius

<400> SEQUENCE: 30

```
Met Ala Thr Ser Leu Asn Ser His Phe Ser Phe Pro Thr Ser Glu Ser
1               5                   10                  15

Lys Thr Thr Arg Phe Pro Asp Trp Tyr Ser Pro Glu Thr Gly Ile Tyr
            20                  25                  30

Thr Ser Lys His Ala Ser Val Ser Ile Pro Thr Asn Pro Tyr Leu Asp
        35                  40                  45

Val Val Ser Phe Ile Phe Ser His Gln His Gln Gly Val Thr Ala Phe
    50                  55                  60

Ile Asp Ser Ser Ser Gly Phe Ser Ile Ser Tyr Ser Lys Leu Leu Pro
65                  70                  75                  80
```

```
Leu Val Gln Ser Met Ala Ser Gly Leu His Leu Gly Val Ser Lys
                85                  90                  95

Gly Asp Val Val Leu Leu Leu Pro Asn Ser Leu His Tyr Pro Ile
            100                 105                 110

Ile Phe Phe Ser Val Leu Tyr Leu Gly Ala Ile Val Thr Pro Met Asn
        115                 120                 125

Pro Leu Ser Ser Ile Ser Glu Ile Lys Lys Gln Ile Ala Asp Ser Asn
130                 135                 140

Val Arg Phe Ala Phe Thr Leu Leu Glu Thr Val Asp Lys Leu Glu Lys
145                 150                 155                 160

Leu Gly Val His Ala Ile Gly Val Pro Glu Asn Met Asn Leu Asp Ser
                165                 170                 175

Glu Lys Val Asp Phe Leu Pro Phe Tyr Lys Leu Met Ala Gly Gln Ser
            180                 185                 190

Gly Asn Lys Ala Pro Arg Pro Val Ile Lys Gln Gln Asp Thr Ala Ala
        195                 200                 205

Ile Met Tyr Ser Ser Gly Thr Thr Gly Thr Ser Lys Gly Val Val Leu
210                 215                 220

Thr His Gly Asn Phe Ile Ala Met Ile Glu Leu Phe Val Lys Phe Glu
225                 230                 235                 240

Ala Ser Gln Tyr Glu Tyr Pro Gly Ser Glu Ile Val Tyr Leu Ala Ala
                245                 250                 255

Leu Pro Met Phe His Ile Tyr Gly Leu Ser Leu Phe Val Val Gly Leu
            260                 265                 270

Leu Ser Leu Gly Ser Thr Val Val Met Arg Lys Phe Asn Ala Gly
        275                 280                 285

Glu Leu Val Lys Val Ile Asp Lys Phe Gly Ile Thr His Phe Pro Val
290                 295                 300

Val Pro Pro Ile Leu Thr Ala Leu Thr Ile Ser Ala Lys Gly Val Cys
305                 310                 315                 320

Glu Asn Asn Phe Lys Ser Leu Lys Gln Val Ser Cys Gly Ala Ala Pro
                325                 330                 335

Ile Ser Arg Lys Ser Ile Glu Asp Phe Val Gln Ala Phe Pro His Val
            340                 345                 350

Asp Phe Ile Gln Gly Tyr Gly Met Thr Glu Ser Thr Ala Val Gly Thr
        355                 360                 365

Arg Gly Phe Asn Thr Gly Lys His His Lys Tyr Ser Ser Ile Gly Leu
370                 375                 380

Leu Ala Pro Asn Met Gln Ala Lys Val Val Asp Leu Asn Ser Gly Ser
385                 390                 395                 400

Ser Met Pro Pro Gly Asp Tyr Gly Glu Leu Trp Leu Arg Gly Pro Ala
                405                 410                 415

Ile Met Gln Arg Tyr Leu Asn Asn Val Glu Ala Thr Leu Met Ser Ile
            420                 425                 430

His Arg Asp Gly Trp Leu Arg Thr Gly Asp Ile Ala Cys Phe Asp Glu
        435                 440                 445

Asp Gly Tyr Met Tyr Leu Ser Asp Arg Leu Lys Glu Ile Ile Lys Tyr
450                 455                 460

Lys Gly Tyr Gln Ile Ala Pro Ala Asp Leu Glu Ala Ile Leu Ile Thr
465                 470                 475                 480

His Pro Glu Ile Leu Asp Ala Ala Val Thr Gly Ala Ser Asp Glu Ala
                485                 490                 495

Cys Gly Glu Ile Pro Val Ala Phe Val Val Arg Arg His Gly Cys Thr
```

Leu Thr His Gly Ala Val Met Asp Phe Val Ala Lys Gln Val Ala Pro
            515                 520                 525

Tyr Lys Lys Val Arg Lys Val Val Phe Ser Asn Ser Ile Pro Arg Ser
        530                 535                 540

Ala Ala Gly Lys Ile Leu Arg Arg Glu Leu Lys Lys Phe Leu Cys Ser
545                 550                 555                 560

Arg Leu

<210> SEQ ID NO 31
<211> LENGTH: 1299
<212> TYPE: DNA
<213> ORGANISM: Corchorus olitorius

<400> SEQUENCE: 31

```
atgattgtga acgtgaaaga atcaacaatg gtacctccgg cggaggagac tccacgggtt     60
tgcttatgga actccaatgt ggacttggtg gtgcccaggt tccatacccc gagcgtctac    120
ttctataggc catcgggtgc atccaacttc tttgacccaa aggtcatgaa ggaggctctg    180
ggcaaggcct tggtgccgtt ttaccccatg gcggggcggt tgaagaggga tgaagatgga    240
aggattgaga ttgattgcaa tggtgcaggg gtgctctttg ttgaggctga gactaatgct    300
gtcattgatg attttggtga ttttgctccc actttggagc tcaggcagct cattccaact    360
gttgattatt ctggtggcat cgagacttac ccgctcttgg ttttgcaggt cacttatttc    420
aaatgtggtg gagcatcact tggtgttggc atgcaacatc atgcggcaga tggcttttct    480
ggtctccatt ttatcaatac atggtccgat atggctcgtg gtcttgacct cacaattcca    540
ccattcatcg atcgtaccct gctccgtgcc cgggatccac cgcaacctgc attcgagcac    600
attgaatacc aaccacctcc tgcattgaaa tctgcacctg aatccacagg ttctgaaggt    660
gcagcagtct ccatttttcaa attgacccga gaacagctaa atgcacttaa agctaagtcc    720
aaggaagatg ggaacactat tgcttatagc tcatatgaga tgttgtcagg tcatgtatgg    780
agatcagtct gcaaagcacg tggacttcct gatgatcaag agtcaaaatt gtacattgcc    840
actgatggaa gggctaggtt gcgcccccca cttccacctg gttactttgg aaatgttatt    900
ttcaccgcta cccaattgc agtggccggt gagctaatgt caaagccaac atggtatgct    960
gctgggaaaa ttcatgatgc cttggttcgc atggacaatg attatctaaa gtcagccctc   1020
gattacctag aacttcagcc tgatttatct gcccttgttc gtggagcaca tacatttaag   1080
tgtccgaatc ttgggattac tagttggtca aggctgccaa tccacgatgc agattttgga   1140
tggggccgac ccatatttat gggtcctggt ggaatccctt atgagggggtt atcttttgtg   1200
ttaccaagtc caaccaatga tgggagctta tcagttgcca tcgctctgca aaccgaacac   1260
atgaaactgt ttgagaagat cttttatgat gacatataa                          1299
```

<210> SEQ ID NO 32
<211> LENGTH: 432
<212> TYPE: PRT
<213> ORGANISM: Corchorus olitorius

<400> SEQUENCE: 32

Met Ile Val Asn Val Lys Glu Ser Thr Met Val Pro Pro Ala Glu Glu
1               5                   10                  15

Thr Pro Arg Val Cys Leu Trp Asn Ser Asn Val Asp Leu Val Val Pro
            20                  25                  30

Arg Phe His Thr Pro Ser Val Tyr Phe Tyr Arg Pro Ser Gly Ala Ser
             35                  40                  45

Asn Phe Asp Pro Lys Val Met Lys Glu Ala Leu Gly Lys Ala Leu
 50                  55                  60

Val Pro Phe Tyr Pro Met Ala Gly Arg Leu Lys Arg Asp Glu Asp Gly
 65                  70                  75                  80

Arg Ile Glu Ile Asp Cys Asn Gly Ala Gly Val Leu Phe Val Glu Ala
                 85                  90                  95

Glu Thr Asn Ala Val Ile Asp Asp Gly Asp Phe Ala Pro Thr Leu
             100                 105                 110

Glu Leu Arg Gln Leu Ile Pro Thr Val Asp Tyr Ser Gly Gly Ile Glu
         115                 120                 125

Thr Tyr Pro Leu Leu Val Leu Gln Val Thr Tyr Phe Lys Cys Gly Gly
         130                 135                 140

Ala Ser Leu Gly Val Gly Met Gln His His Ala Ala Asp Gly Phe Ser
145                 150                 155                 160

Gly Leu His Phe Ile Asn Thr Trp Ser Asp Met Ala Arg Gly Leu Asp
                 165                 170                 175

Leu Thr Ile Pro Pro Phe Ile Asp Arg Thr Leu Leu Arg Ala Arg Asp
             180                 185                 190

Pro Pro Gln Pro Ala Phe Glu His Ile Glu Tyr Gln Pro Pro Pro Ala
         195                 200                 205

Leu Lys Ser Ala Pro Glu Ser Thr Gly Ser Glu Gly Ala Ala Val Ser
         210                 215                 220

Ile Phe Lys Leu Thr Arg Glu Gln Leu Asn Ala Leu Lys Ala Lys Ser
225                 230                 235                 240

Lys Glu Asp Gly Asn Thr Ile Ala Tyr Ser Ser Tyr Glu Met Leu Ser
                 245                 250                 255

Gly His Val Trp Arg Ser Val Cys Lys Ala Arg Gly Leu Pro Asp Asp
             260                 265                 270

Gln Glu Ser Lys Leu Tyr Ile Ala Thr Asp Gly Arg Ala Arg Leu Arg
         275                 280                 285

Pro Pro Leu Pro Pro Gly Tyr Phe Gly Asn Val Ile Phe Thr Ala Thr
         290                 295                 300

Pro Ile Ala Val Ala Gly Glu Leu Met Ser Lys Pro Thr Trp Tyr Ala
305                 310                 315                 320

Ala Gly Lys Ile His Asp Ala Leu Val Arg Met Asp Asn Asp Tyr Leu
                 325                 330                 335

Lys Ser Ala Leu Asp Tyr Leu Glu Leu Gln Pro Asp Leu Ser Ala Leu
             340                 345                 350

Val Arg Gly Ala His Thr Phe Lys Cys Pro Asn Leu Gly Ile Thr Ser
         355                 360                 365

Trp Ser Arg Leu Pro Ile His Asp Ala Asp Phe Gly Trp Gly Arg Pro
         370                 375                 380

Ile Phe Met Gly Pro Gly Gly Ile Pro Tyr Glu Gly Leu Ser Phe Val
385                 390                 395                 400

Leu Pro Ser Pro Thr Asn Asp Gly Ser Leu Ser Val Ala Ile Ala Leu
                 405                 410                 415

Gln Thr Glu His Met Lys Leu Phe Glu Lys Ile Phe Tyr Asp Asp Ile
             420                 425                 430

<210> SEQ ID NO 33
<211> LENGTH: 1062
<212> TYPE: DNA

<213> ORGANISM: Corchorus olitorius

<400> SEQUENCE: 33

```
atgccaattt cggatgcaga aagcaagaat aaaactttgc aagtaaggga ttacttggga      60
gcagtggcat tcaacaacat aacaaggcta gtatttggga agcgttttat gaactctgag     120
ggcataattg acgagcaagg caaagaattc aagggcattg tgtcaaatgg aactaagatt     180
ggtgcatccc ttgccatggc agagcacatt ccatggcttc gttggatgtt tcccttggaa     240
gaggaagcat ttgccaagca tgcagcaagg agggacaatc ttaccagaac catcatggag     300
gagcacaccg ctgctcgcaa gaagagcggt ggtgctaagc agcatttgt tgatgccttg      360
ctcacattgc aagaaaagta tgacctcagc gacgacacag ttattggact actttgggac    420
atgattacag caggcatgga tacaacagca attgcagcag agtgggcaat ggcagagtta     480
atcaagaacc caagagtgca gcaaaaggca aagaggagc tagatcgtgt ggtaggattc      540
gaaagggtga tgtccgaaac tgatttctca agcctgcctt accttcaaag tgtaaccaag     600
gaggcattca gaatgcaccc cccaactcct ctaatgctac cccacaaagc caacgccaat    660
gtcaaaatcg aggttatga catccccaag ggatcaaatg tgcatgtcaa cgtctgggca     720
gtggccaatg atccggctgt atggaaggac cctgaagtgt tccggccaga gcgattcctg    780
gaggaggatg tggacatgaa gggtcatgat tatcgcttgc ttccttttgg tgcggggagg    840
agggtatgcc ctggagcaca acttgggatc aacctggtca catccatgtt gggtcactta    900
ctgcaccatt ttgtttggac accaccagag ggagtaaagg ccgaggaaat cgacatggct    960
gaaaatcccg acttgttgc ctacatgaag actcctgtgc aggctgtggc cactcctagg    1020
ctgccttccg atctctacaa acgtgtagct gttgacatat aa                      1062
```

<210> SEQ ID NO 34
<211> LENGTH: 353
<212> TYPE: PRT
<213> ORGANISM: Corchorus olitorius

<400> SEQUENCE: 34

```
Met Pro Ile Ser Asp Ala Glu Ser Lys Asn Lys Thr Leu Gln Val Arg
1               5                   10                  15

Asp Tyr Leu Gly Ala Val Ala Phe Asn Asn Ile Thr Arg Leu Val Phe
            20                  25                  30

Gly Lys Arg Phe Met Asn Ser Glu Gly Ile Ile Asp Glu Gln Gly Lys
        35                  40                  45

Glu Phe Lys Gly Ile Val Ser Asn Gly Thr Lys Ile Gly Ala Ser Leu
    50                  55                  60

Ala Met Ala Glu His Ile Pro Trp Leu Arg Trp Met Phe Pro Leu Glu
65                  70                  75                  80

Glu Glu Ala Phe Ala Lys His Ala Ala Arg Arg Asp Asn Leu Thr Arg
                85                  90                  95

Thr Ile Met Glu Glu His Thr Ala Ala Arg Lys Lys Ser Gly Gly Ala
            100                 105                 110

Lys Gln His Phe Val Asp Ala Leu Leu Thr Leu Gln Glu Lys Tyr Asp
        115                 120                 125

Leu Ser Asp Asp Thr Val Ile Gly Leu Leu Trp Asp Met Ile Thr Ala
    130                 135                 140

Gly Met Asp Thr Thr Ala Ile Ala Ala Glu Trp Ala Met Ala Glu Leu
145                 150                 155                 160

Ile Lys Asn Pro Arg Val Gln Gln Lys Ala Gln Glu Glu Leu Asp Arg
```

165                 170                 175
Val Val Gly Phe Glu Arg Val Met Ser Glu Thr Asp Phe Ser Ser Leu
            180                 185                 190

Pro Tyr Leu Gln Ser Val Thr Lys Glu Ala Phe Arg Met His Pro Pro
        195                 200                 205

Thr Pro Leu Met Leu Pro His Lys Ala Asn Ala Asn Val Lys Ile Gly
    210                 215                 220

Gly Tyr Asp Ile Pro Lys Gly Ser Asn Val His Val Asn Val Trp Ala
225                 230                 235                 240

Val Ala Asn Asp Pro Ala Val Trp Lys Asp Pro Glu Val Phe Arg Pro
                245                 250                 255

Glu Arg Phe Leu Glu Glu Asp Val Asp Met Lys Gly His Asp Tyr Arg
            260                 265                 270

Leu Leu Pro Phe Gly Ala Gly Arg Arg Val Cys Pro Gly Ala Gln Leu
        275                 280                 285

Gly Ile Asn Leu Val Thr Ser Met Leu Gly His Leu Leu His His Phe
    290                 295                 300

Val Trp Thr Pro Pro Glu Gly Val Lys Ala Glu Glu Ile Asp Met Ala
305                 310                 315                 320

Glu Asn Pro Gly Leu Val Ala Tyr Met Lys Thr Pro Val Gln Ala Val
                325                 330                 335

Ala Thr Pro Arg Leu Pro Ser Asp Leu Tyr Lys Arg Val Ala Val Asp
            340                 345                 350

Ile

<210> SEQ ID NO 35
<211> LENGTH: 1446
<212> TYPE: DNA
<213> ORGANISM: Corchorus olitorius

<400> SEQUENCE: 35

```
atggatcttc tcttcctgga gaaggccctt attggtcttt tcgtggctgt catcttagcc      60
atcgccatct ctaaactccg gggaaagcgt tacaagctcc ctcctggtcc tttacccgtt     120
cccgtcttcg gcaactggct ccaagtgggc gacgacttga accaccgtaa cctaactgac     180
ttggccaaga aatatggcga catattcctc ctccgaatgg ggcagcgcaa cctggtggtg     240
gtgtcgtctc cggaactagc caaagaggtg ctccacaccc aggagtggaa ttcgggtca      300 agaacccgga atgtggtgtt tgacatattc accggcaagg gtcaagacat ggtgttcacg     360
gtgtacgttg tccagcagta ccggtttgga tgggaggagg aagccgctcg cgttgtggag     420
gatgtcaaga aaaatcccga ggctgccacc aatggcatcg ttctgaggag gaggttgcag     480
ctcatgatgt acaacaatat gtacagaatc atgttcgacc ggaggttcga gagcgaggag     540
gatcctctgt tgttaaaact caaggctttg aacggggaga ggagtcgatt ggctcagagt     600
tttgagtaca attatggaga ttttattcct attttgaggc cttttcttga gggttacttg     660
aagatctgca aggaggttaa agagaggagg ttgcaactct tcaaggacta ctttgtcgaa     720
gagagaaaga aacttgcaag cacgaagagc atgagcaacg aaggattgaa atgtgccata     780 gatcatatt tggatgctca gcagaaaggg gagatcaacg aggacaatgt tctgtatatc     840
gtcgagaaca tcaatgttgc cgcaattgag acaacattat ggtcgatcga gtgggcatt      900 gcagagctgg tgaaccaccc tgaaatccag aagaagctgc gagatgaact tgacactctt     960
cttggacccg gccaccagat caccgaaccc gacacctaca aactccctta ccttcaggct    1020
```

-continued

```
gtcatcaagg agactttgag gcttcgtatg gccattcctc tgctcgtccc ccacatgaac   1080
ctccacgatg ctaagcttgc cggctatgat atccccgctg agagcaaaat cttggtcaat   1140
gcatggtggc tcgccaacaa ccctgcccag tggaaaaacc cccaggagtt taggcccgag   1200
aggttctttg aagaggaatc taaggttgag gccaatggca atgacttcag gtaccttcca   1260
tttggggttg aagaagaag ttgccctgga attattctcg ctttgcccat ccttggtatc    1320
actttgggcc gcttagtaca gaatttcgag ctcttgcctc caccaggaca gtccaagatt   1380
gataccctcg agaaggtgg acagttcagt ttgcacattt tgaagcattc caccattgtt    1440
ttgtaa                                                               1446
```

<210> SEQ ID NO 36
<211> LENGTH: 481
<212> TYPE: PRT
<213> ORGANISM: Corchorus olitorius

<400> SEQUENCE: 36

```
Met Asp Leu Leu Phe Leu Glu Lys Ala Leu Ile Gly Leu Phe Val Ala
1               5                   10                  15

Val Ile Leu Ala Ile Ala Ile Ser Lys Leu Arg Gly Lys Arg Tyr Lys
            20                  25                  30

Leu Pro Pro Gly Pro Leu Pro Val Pro Val Phe Gly Asn Trp Leu Gln
        35                  40                  45

Val Gly Asp Asp Leu Asn His Arg Asn Leu Thr Asp Leu Ala Lys Lys
    50                  55                  60

Tyr Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Val Gln Gln Tyr Arg
        115                 120                 125

Phe Gly Trp Glu Glu Glu Ala Ala Arg Val Val Glu Asp Val Lys Lys
    130                 135                 140

Asn Pro Glu Ala Ala Thr Asn Gly Ile Val Leu Arg Arg Arg Leu Gln
145                 150                 155                 160

Leu Met Met Tyr Asn Asn Met Tyr Arg Ile Met Phe Asp Arg Arg Phe
                165                 170                 175

Glu Ser Glu Glu Asp Pro Leu Phe Val Lys Leu Lys Ala Leu Asn Gly
            180                 185                 190

Glu Arg Ser Arg Leu Ala Gln Ser Phe Glu Tyr Asn Tyr Gly Asp Phe
        195                 200                 205

Ile Pro Ile Leu Arg Pro Phe Leu Arg Gly Tyr Leu Lys Ile Cys Lys
    210                 215                 220

Glu Val Lys Glu Arg Arg Leu Gln Leu Phe Lys Asp Tyr Phe Val Glu
225                 230                 235                 240

Glu Arg Lys Lys Leu Ala Ser Thr Lys Ser Met Ser Asn Glu Gly Leu
                245                 250                 255

Lys Cys Ala Ile Asp His Ile Leu Asp Ala Gln Gln Lys Gly Glu Ile
            260                 265                 270

Asn Glu Asp Asn Val Leu Tyr Ile Val Glu Asn Ile Asn Val Ala Ala
        275                 280                 285

Ile Glu Thr Thr Leu Trp Ser Ile Glu Trp Gly Ile Ala Glu Leu Val
```

```
                     290                 295                 300

Asn His Pro Glu Ile Gln Lys Lys Leu Arg Asp Glu Leu Asp Thr Leu
305                 310                 315                 320

Leu Gly Pro Gly His Gln Ile Thr Glu Pro Asp Thr Tyr Lys Leu Pro
                325                 330                 335

Tyr Leu Gln Ala Val Ile Lys Glu Thr Leu Arg Leu Arg Met Ala Ile
            340                 345                 350

Pro Leu Leu Val Pro His Met Asn Leu His Asp Ala Lys Leu Ala Gly
        355                 360                 365

Tyr Asp Ile Pro Ala Glu Ser Lys Ile Leu Val Asn Ala Trp Trp Leu
    370                 375                 380

Ala Asn Asn Pro Ala Gln Trp Lys Asn Pro Gln Glu Phe Arg Pro Glu
385                 390                 395                 400

Arg Phe Phe Glu Glu Glu Ser Lys Val Glu Ala Asn Gly Asn Asp Phe
                405                 410                 415

Arg Tyr Leu Pro Phe Gly Val Gly Arg Arg Ser Cys Pro Gly Ile Ile
                420                 425                 430

Leu Ala Leu Pro Ile Leu Gly Ile Thr Leu Gly Arg Leu Val Gln Asn
            435                 440                 445

Phe Glu Leu Leu Pro Pro Gly Gln Ser Lys Ile Asp Thr Ser Glu
        450                 455                 460

Lys Gly Gly Gln Phe Ser Leu His Ile Leu Lys His Ser Thr Ile Val
465                 470                 475                 480

Leu

<210> SEQ ID NO 37
<211> LENGTH: 1518
<212> TYPE: DNA
<213> ORGANISM: Corchorus olitorius

<400> SEQUENCE: 37
atggacctcc tcttcctcga aaaagctctc atttcccttt tcgtcaccat aattgtagcc      60
attgtagtct ccaagctccg cggcaagcgt tacaaacttc cccctggccc aatcccagtc     120
cctgttttcg gcaactggct ccaagtcggc gatgacttga accaccgcaa cctcaccgac     180
ttggccaaga agttcggaga cattttcttg ctccgtatgg gacagcgcaa cctcgtcgtt     240
gtgtcttccc cggagctggc caaagaagtc ctccataccc aggagttgag tttggttca     300 agaactagaa atgtggtgtt tgatattttc acagggaaag gtcaggacat ggttttcact     360
gtctatggtg aacattggcg caaaatgagg agaatcatga ccgtcccttt cttcaccaac     420
aaggttgttc aacagtatag acatgggtgg gaagcggagg ttgccgccgt cgttgaggat     480
gtgaagaaga acccagagtc ggccaccact gggattgttc tgaggaagag attgcagctt     540
atgatgtaca caatatgta ccggatcatg tttgatagaa ggtttgagag tgaagatgat     600
cctttgtttg ttaagctcaa ggctttgaat ggtgagagga gtagattggc acagagcttt     660
gattacaact atggtgattt catcccaatt ttgaggcctt tcttgagagg gtatttgaag     720
ttatgcaagg aagtcaaaga aatgagattg caactctta gggaccattt ccttgaggag     780
aggaagaagc tttcaagcac aaaaaggcct gacaacaatg ctctgaagtg tgccattgat     840
cacattcttg atgctcagca gaaaggagaa atcaatgaag ataatgttct ctacattgtt     900
gagaatatca atgttgctgc cattgaaaca actttgtggt caattgaatg ggaattgct     960 gagcttgtga accatcctga gatccagcag aagctccgca tgaaatcga cactgtactc    1020
```

-continued

```
ggaccaggag tgcaagttac cgaacccgac acccacaagc ttccatatct ccaggcagtg      1080
atcaaggaga ccctccggct ccggatggcc atccctctat tagtgccaca catgaacctc      1140
catgatgcta agcttggtgg ctatgacatc ccagctgaaa gcaagatcct tgttaacgca      1200
tggtggttag ccaacaaccc ggctcaatgg aagaacccgg aagagttcag gcccgaaagg      1260
tttttcgagg aggaagctaa ggttgaagcc aatggaaatg acttcaggta ccttccattt      1320
ggtgttggaa ggaggagttg cccaggaatt attcttgcct tgccaatctt aggaatcaca      1380
ttgggacgtt tggtgcaaaa ctttgagcta ttgcctcctc ctggacagtc aaagcttgat      1440
acctcagaga aaggaggaca attcagcttg cacattctca gcattcaac tattgttgca      1500 aagccacgag tcttttaa                                                   1518
```

<210> SEQ ID NO 38
<211> LENGTH: 505
<212> TYPE: PRT
<213> ORGANISM: Corchorus olitorius

<400> SEQUENCE: 38

```
Met Asp Leu Leu Phe Leu Glu Lys Ala Leu Ile Ser Leu Phe Val Thr
1               5                   10                  15

Ile Ile Val Ala Ile Val Val Ser Lys Leu Arg Gly Lys Arg Tyr Lys
            20                  25                  30

Leu Pro Pro Gly Pro Ile Pro Val Pro Val Phe Gly Asn Trp Leu Gln
        35                  40                  45

Val Gly Asp Asp Leu Asn His Arg Asn Leu Thr Asp Leu Ala Lys Lys
    50                  55                  60

Phe Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
    130                 135                 140

Gln Tyr Arg His Gly Trp Glu Ala Glu Val Ala Ala Val Val Glu Asp
145                 150                 155                 160

Val Lys Lys Asn Pro Glu Ser Ala Thr Thr Gly Ile Val Leu Arg Lys
                165                 170                 175

Arg Leu Gln Leu Met Met Tyr Asn Asn Met Tyr Arg Ile Met Phe Asp
            180                 185                 190

Arg Arg Phe Glu Ser Glu Asp Asp Pro Leu Phe Val Lys Leu Lys Ala
        195                 200                 205

Leu Asn Gly Glu Arg Ser Arg Leu Ala Gln Ser Phe Asp Tyr Asn Tyr
    210                 215                 220

Gly Asp Phe Ile Pro Ile Leu Arg Pro Phe Leu Arg Gly Tyr Leu Lys
225                 230                 235                 240

Leu Cys Lys Glu Val Lys Glu Met Arg Leu Gln Leu Phe Arg Asp His
                245                 250                 255

Phe Leu Glu Glu Arg Lys Lys Leu Ser Ser Thr Lys Arg Pro Asp Asn
            260                 265                 270

Asn Ala Leu Lys Cys Ala Ile Asp His Ile Leu Asp Ala Gln Gln Lys
        275                 280                 285
```

```
Gly Glu Ile Asn Glu Asp Asn Val Leu Tyr Ile Val Glu Asn Ile Asn
            290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Gln Lys Leu Arg Asn Glu Ile
                325                 330                 335

Asp Thr Val Leu Gly Pro Gly Val Gln Val Thr Glu Pro Asp Thr His
            340                 345                 350

Lys Leu Pro Tyr Leu Gln Ala Val Ile Lys Glu Thr Leu Arg Leu Arg
            355                 360                 365

Met Ala Ile Pro Leu Leu Val Pro His Met Asn Leu His Asp Ala Lys
370                 375                 380

Leu Gly Gly Tyr Asp Ile Pro Ala Glu Ser Lys Ile Leu Val Asn Ala
385                 390                 395                 400

Trp Trp Leu Ala Asn Asn Pro Ala Gln Trp Lys Asn Pro Glu Glu Phe
            405                 410                 415

Arg Pro Glu Arg Phe Phe Glu Glu Ala Lys Val Glu Ala Asn Gly
            420                 425                 430

Asn Asp Phe Arg Tyr Leu Pro Phe Gly Val Gly Arg Arg Ser Cys Pro
            435                 440                 445

Gly Ile Ile Leu Ala Leu Pro Ile Leu Gly Ile Thr Leu Gly Arg Leu
450                 455                 460

Val Gln Asn Phe Glu Leu Leu Pro Pro Gly Gln Ser Lys Leu Asp
465                 470                 475                 480

Thr Ser Glu Lys Gly Gly Gln Phe Ser Leu His Ile Leu Lys His Ser
            485                 490                 495

Thr Ile Val Ala Lys Pro Arg Val Phe
            500                 505

<210> SEQ ID NO 39
<211> LENGTH: 1580
<212> TYPE: DNA
<213> ORGANISM: Corchorus olitorius

<400> SEQUENCE: 39
ggattgttat ctctctcagg tcataatttt aaaacatggc tcatccttct aagaaagcaa      60
ttcttgccat tataacacta tccttgatct ttgttcttgc taccaccaaa aacttgtccc     120 tcacccttt gccactcttt cttgtcacct acttttatt gcagaaacgt tctaattctt      180
ccaatgccct ccctccaggt cctctctctg ttcccatatt tggaaactgg ctccaggttg     240
gaaatgacct aaaccaccgg ctcctagctt ccttggctga aacctatggc ccagtcttcc     300
tcctaaaact tggctccaag aatctagcag tggtttcaga cccagagcta gcctcccagg     360
ttcttcacac ccaaggggtc gaattcggtt ccaggccacg caacgtggtg tttgacattt     420
tcacgggcaa tgggcaggac atggtgttca cagtttacgg agaccattgg cgaaaaatgc     480
gcagaattat gacttttgcca tttttcacta caaagttgt gcacaattac agtaacatgt    540
gggaggaaga gatggagctt gtggttagtg acttgaagag agatgaggaa ttggtgaaga     600
gcaaagggat tgttatcaga aaacgtctgc agcttatgct ttataacatc atgtatagga     660
tgatgtttga tgccaagttc gagtccatgg aagacccttt attcgttgag caaccaggt      720 tcaattccga gagaagccgc ttggctcaga gttttgagta caattatggt gatttcattc     780
cattgctcag accctttttg agagggtact tgaacaagtg cagggatttg cagagcaggc    840
```

-continued

```
ggcttgcctt cttcaacaac tattatgtta agaaaagaag ggaaattatg ggtgctaatg       900
gagagaagca caaaatcagc tgtgcaattg attacataat agatgctgaa atgaagggag       960
agattagtga agaaaatgtg ctctacattg tggaaaacat caatgttgca gccattgaaa      1020
ccactctgtg gtcaatggag tgggcaatag ctgaggtggt gaaccaccca aatgtgcagc      1080
aaaagatccg ccaagaaatc tcacaagtcc tcaaggaga ggctgtcaca gaatcaaacc       1140
tccttgaatt gccttacttg caagccactg tcaaggagac actacggtta cacacccccaa     1200 ttcctctgtt ggttcctcac atgaaccttg aagaggcaaa attgggaggg ttcacaattc      1260
caaaggagtc caaggttgta gtcaatgcct ggtggctggc caacaatcca aaatggtggg      1320
aaaatccaga ggaattcagg ccagagcggt ttttggaaga agaatcggcc acacaagccg      1380
tcgccggagg gaaagttgat ttcaggtatt tgccatttgg aatgggaagg cgtagctgcc      1440
ctggtatcat actggcactg ccaatcctgg ggcttatcat tgccaaattg gttacaaatt      1500
ttgaaatcaa agctccccaa ggaacacaca agattgatgt gagtgagaaa ggagggcaat      1560
tcagtttaca catagcaaac                                                  1580

<210> SEQ ID NO 40
<211> LENGTH: 1677
<212> TYPE: DNA
<213> ORGANISM: Corchorus olitorius

<400> SEQUENCE: 40
atgcttgtca gaatcaacac tttgttgcag ggttattctg gaatcagatt cgaaattttg        60
gaagcaatta ccaaatttct gaaccagaac ataactccat gtttgccact cgtggaaca       120 attacagctt caggggatct ggttccactt tcttacattg caggacttct taccggaaga      180
ccaaattcca aggcggttgg acctaacggt gaatcgttaa acgccgagga agctttcaat      240
cgtgccggga tcgaatctgg gttctttacc ttgcagccca aggaaggtct tgctcttgtt      300
aatgggacag cagttgggtc tggaatggct tctatggttc tttttgaagc caacatttta      360
gctgtattgt ccgaagtttt gtctgcaatt tcgctgaag tcatgaatgg taaacctgaa       420
tttaccgacc atttgacaca taaattgaag catcatcctg acaaatcga agctgctgca       480 attatggaac atattttgga tggaagtggg tatgttaaag cggcgaagaa attacatgaa      540
atggatccat tgcagaaacc aaagcaagat cgttatgctt taagaacttc cccacaatgg      600
cttggtccac agattgaagt gatcagattt gcaacaaagt caattgaaag agaaatcaat      660
tctgttaatg acaacccttt gatcgatgtt tctagaaaca aggctcttca tggtggaaac      720
ttccaaggaa ctcctattgg tgtttctatg gataatgctc gtttggctat tgcttcaatt      780
gggaaactca tgtttgctca attttctgaa cttgttaatg attttacaa caatgggctc       840 ccatcaaatc tgtcaggtgg aaggaatccc agtttggatt atggattcaa aggtgctgaa      900
attgccatgg cttcttattg ttccgaactt caattccttg ctaatcctgt taccaatcat      960
gtccaaagtg ctgagcaaca taatcaggat gttaattcct tgggattgat ttccgcaagg     1020
aaaacttcag aagctgttga tattttgaag cttatgtctt ctacttactt agttgctctg     1080
tgccaagcta ttgatttgag gcatttggaa gaaaacttga ggaacacggt aaagaacact     1140
gtgagccaga ttgctaagaa ggttttgacc actggtgcca atggtgaact tcacccttca     1200
agattctgtg agaaggactt gctcaaagcc gttgaccgcg aatacgtttt cgcttacatt     1260
gatgatcctt gcagtgctac ttacccattg atgcagaaat tgagacaagt tcttgttgag     1320
catgcattga caaatggtga gagtgagaag aatgcaagca cttcaatttt ccagaaaatt     1380
```

```
gcagcatttg aagaggaatt gaagactttg ttgcctaagg aagttgagag tgcaagagtg   1440
gcacttgaga atgggtcaaa tgtggcagtg ccaaacagaa tcaaggaatg cagaagttac   1500
ccattgtata aatttgtgag ggaagagctt ggaactgggc ttttgactgg tgaaaaagtt   1560
aggtcacctg gtgaggaatt tgacaaggtt ttcacagcta tgtgccaggg gaaactcatt   1620
gatccaatgc ttgagtgtct caaggaatgg gacggtgccc ctcttcccat ctgctag     1677
```

```
<210> SEQ ID NO 41
<211> LENGTH: 558
<212> TYPE: PRT
<213> ORGANISM: Corchorus olitorius

<400> SEQUENCE: 41
```

```
Met Leu Val Arg Ile Asn Thr Leu Leu Gln Gly Tyr Ser Gly Ile Arg
1               5                   10                  15

Phe Glu Ile Leu Glu Ala Ile Thr Lys Phe Leu Asn Gln Asn Ile Thr
            20                  25                  30

Pro Cys Leu Pro Leu Arg Gly Thr Ile Thr Ala Ser Gly Asp Leu Val
        35                  40                  45

Pro Leu Ser Tyr Ile Ala Gly Leu Leu Thr Gly Arg Pro Asn Ser Lys
    50                  55                  60

Ala Val Gly Pro Asn Gly Glu Ser Leu Asn Ala Glu Ala Phe Asn
65                  70                  75                  80

Arg Ala Gly Ile Glu Ser Gly Phe Phe Thr Leu Gln Pro Lys Glu Gly
                85                  90                  95

Leu Ala Leu Val Asn Gly Thr Ala Val Gly Ser Gly Met Ala Ser Met
            100                 105                 110

Val Leu Phe Glu Ala Asn Ile Leu Ala Val Leu Ser Glu Val Leu Ser
            115                 120                 125

Ala Ile Phe Ala Glu Val Met Asn Gly Lys Pro Glu Phe Thr Asp His
        130                 135                 140

Leu Thr His Lys Leu Lys His His Pro Gly Gln Ile Glu Ala Ala Ala
145                 150                 155                 160

Ile Met Glu His Ile Leu Asp Gly Ser Gly Tyr Val Lys Ala Ala Lys
                165                 170                 175

Lys Leu His Glu Met Asp Pro Leu Gln Lys Pro Lys Gln Asp Arg Tyr
            180                 185                 190

Ala Leu Arg Thr Ser Pro Gln Trp Leu Gly Pro Gln Ile Glu Val Ile
        195                 200                 205

Arg Phe Ala Thr Lys Ser Ile Glu Arg Glu Ile Asn Ser Val Asn Asp
    210                 215                 220

Asn Pro Leu Ile Asp Val Ser Arg Asn Lys Ala Leu His Gly Gly Asn
225                 230                 235                 240

Phe Gln Gly Thr Pro Ile Gly Val Ser Met Asp Asn Ala Arg Leu Ala
                245                 250                 255

Ile Ala Ser Ile Gly Lys Leu Met Phe Ala Gln Phe Ser Glu Leu Val
            260                 265                 270

Asn Asp Phe Tyr Asn Asn Gly Leu Pro Ser Asn Leu Ser Gly Gly Arg
        275                 280                 285

Asn Pro Ser Leu Asp Tyr Gly Phe Lys Gly Ala Glu Ile Ala Met Ala
    290                 295                 300

Ser Tyr Cys Ser Glu Leu Gln Phe Leu Ala Asn Pro Val Thr Asn His
305                 310                 315                 320
```

```
Val Gln Ser Ala Glu Gln His Asn Gln Asp Val Asn Ser Leu Gly Leu
                325                 330                 335
Ile Ser Ala Arg Lys Thr Ser Glu Ala Val Asp Ile Leu Lys Leu Met
            340                 345                 350
Ser Ser Thr Tyr Leu Val Ala Leu Cys Gln Ala Ile Asp Leu Arg His
        355                 360                 365
Leu Glu Glu Asn Leu Arg Asn Thr Val Lys Asn Thr Val Ser Gln Ile
    370                 375                 380
Ala Lys Lys Val Leu Thr Thr Gly Ala Asn Gly Glu Leu His Pro Ser
385                 390                 395                 400
Arg Phe Cys Glu Lys Asp Leu Leu Lys Ala Val Asp Arg Glu Tyr Val
                405                 410                 415
Phe Ala Tyr Ile Asp Asp Pro Cys Ser Ala Thr Tyr Pro Leu Met Gln
            420                 425                 430
Lys Leu Arg Gln Val Leu Val Glu His Ala Leu Thr Asn Gly Glu Ser
        435                 440                 445
Glu Lys Asn Ala Ser Thr Ser Ile Phe Gln Lys Ile Ala Ala Phe Glu
    450                 455                 460
Glu Glu Leu Lys Thr Leu Leu Pro Lys Glu Val Glu Ser Ala Arg Val
465                 470                 475                 480
Ala Leu Glu Asn Gly Ser Asn Val Ala Val Pro Asn Arg Ile Lys Glu
                485                 490                 495
Cys Arg Ser Tyr Pro Leu Tyr Lys Phe Val Arg Glu Glu Leu Gly Thr
            500                 505                 510
Gly Leu Leu Thr Gly Lys Val Arg Ser Pro Gly Glu Glu Phe Asp
        515                 520                 525
Lys Val Phe Thr Ala Met Cys Gln Gly Lys Leu Ile Asp Pro Met Leu
    530                 535                 540
Glu Cys Leu Lys Glu Trp Asp Gly Ala Pro Leu Pro Ile Cys
545                 550                 555
```

<210> SEQ ID NO 42
<211> LENGTH: 1743
<212> TYPE: DNA
<213> ORGANISM: Corchorus olitorius

<400> SEQUENCE: 42

```
atgctggagt tttcggccaa ggcactgagt cgtgcccata cgttgccgca cacggcgacg      60
agggcggcta tgcttgtgag atcaacact cttttgcaag atattctgg cattagattt      120
gagatcctag aagctataac caagttcctc aatgtgaaca ttaccccatg tgtgccactt     180
agggatcaa ttactgcatc tggtgacttg gtgccattgt cctacatagc cgggcttttg     240
acaggcaggc ctaattccaa ggctcttggg cctaacggtg aggccatgaa ccccacagaa     300
gcttttagcc gggccggaat ccatggtggg ttttcgagt tgcagcccaa agagggtctt     360
gctttagtca atggtacagc cgttgggtca ggcttagcct ctttggtcct ttatgaggcc     420
aatgttttag cagtcctctc agaagtttta tcagcaattt ttgctgaagt tatgcaaggc     480
aaacctgaat tcactgacca tttaactcac aagttgaagc atcatccagg acaaattgaa     540
gctgctgcca ttatgaaca tattttggat ggtagctctt acattaaagc agcacaaaaa     600
ttgcatgaaa tggatcctct tcagaaacca aaacaggaca gatatgctct tagaacttcc     660
cctcaatggc ttggccctca aattgaagta atcaggtcag caaccaaaat gattgaaagg     720
gaaatcaatt cagtgaatga taatcccttta attgatgttt caagagacaa ggctttacat     780
```

-continued

```
ggagggaatt tccaaggtac cccaattggt gtttcaatgg acaacactcg tttagccatt    840
gctgcaattg gtaaactcat gtttgctcaa ttttctgagc ttgttaatga ttattacaac    900
aatggtttgc cttcaaatct gtctgctagc cgcaacccga gtttggatta tggtttcaaa    960
ggagctgaaa ttgcaatggc ttcttattgc tcagagcttc aattccttgg taatcctgtc   1020
actaaccatg tccaaagtgc tgagcaacat aaccaagatg tcaactcatt agggttgatc   1080
tcagcaagaa aaacagctga agctattgat atattgaagc tgatgtcttc aactttcttg   1140
attgctttat gccaagcaat tgacttgagg catttggaag agaatttgaa gaacactgtc   1200
aagaacacag ttagtcaaat tgccaagagg gtcttaacca tgggatcaaa cggtgaactt   1260
catccatcaa gattctgtga aaagatcttc tcagagttg tcgatcgcga acatctctat   1320
gcctatattg atgatccttg cagtgcaagt tacccattaa tgcagaagtt gagacaagta   1380
ctggtagacc atgccttgat gaatggtgac aatgagaaga actcaaccac ctccattttc   1440
cagaagattg gtgcctttga agaagaattg aaaaccctt tgcctaaaga agttgagagt   1500
gctagaatcg aattcgagaa tggaaatgca gcaattccta acagaatcaa agaatgcagg   1560
tcctatccat gtacaagtt tgtgagggaa gttcttggga ctagcttgtt aactggtgaa   1620
aaggtgatct ctccagggga agaatgtgac aaggttttct cagcaatttg tgcaggaaag   1680
ttgattgatc cattgtttca atgcttgaag gagtggaatg gtgctccttt gcctatatgc   1740
taa                                                                1743
```

<210> SEQ ID NO 43
<211> LENGTH: 580
<212> TYPE: PRT
<213> ORGANISM: Corchorus olitorius

<400> SEQUENCE: 43

```
Met Leu Glu Phe Ser Ala Lys Ala Leu Ser Arg Ala His Thr Leu Pro
1               5                   10                  15

His Thr Ala Thr Arg Ala Ala Met Leu Val Arg Ile Asn Thr Leu Leu
            20                  25                  30

Gln Gly Tyr Ser Gly Ile Arg Phe Glu Ile Leu Glu Ala Ile Thr Lys
        35                  40                  45

Phe Leu Asn Val Asn Ile Thr Pro Cys Val Pro Leu Arg Gly Ser Ile
    50                  55                  60

Thr Ala Ser Gly Asp Leu Val Pro Leu Ser Tyr Ile Ala Gly Leu Leu
65                  70                  75                  80

Thr Gly Arg Pro Asn Ser Lys Ala Leu Gly Pro Asn Gly Glu Ala Met
                85                  90                  95

Asn Pro Thr Glu Ala Phe Ser Arg Ala Gly Ile His Gly Gly Phe Phe
            100                 105                 110

Glu Leu Gln Pro Lys Glu Gly Leu Ala Leu Val Asn Gly Thr Ala Val
        115                 120                 125

Gly Ser Gly Leu Ala Ser Leu Val Leu Tyr Glu Ala Asn Val Leu Ala
    130                 135                 140

Val Leu Ser Glu Val Leu Ser Ala Ile Phe Ala Glu Val Met Gln Gly
145                 150                 155                 160

Lys Pro Glu Phe Thr Asp His Leu Thr His Lys Leu Lys His His Pro
                165                 170                 175

Gly Gln Ile Glu Ala Ala Ala Ile Met Glu His Ile Leu Asp Gly Ser
            180                 185                 190

Ser Tyr Ile Lys Ala Ala Gln Lys Leu His Glu Met Asp Pro Leu Gln
```

```
                195                 200                 205
Lys Pro Lys Gln Asp Arg Tyr Ala Leu Arg Thr Ser Pro Gln Trp Leu
210                 215                 220

Gly Pro Gln Ile Glu Val Ile Arg Ser Ala Thr Lys Met Ile Glu Arg
225                 230                 235                 240

Glu Ile Asn Ser Val Asn Asp Asn Pro Leu Ile Asp Val Ser Arg Asp
                245                 250                 255

Lys Ala Leu His Gly Gly Asn Phe Gln Gly Thr Pro Ile Gly Val Ser
            260                 265                 270

Met Asp Asn Thr Arg Leu Ala Ile Ala Ala Ile Gly Lys Leu Met Phe
        275                 280                 285

Ala Gln Phe Ser Glu Leu Val Asn Asp Tyr Tyr Asn Asn Gly Leu Pro
    290                 295                 300

Ser Asn Leu Ser Ala Ser Arg Asn Pro Ser Leu Asp Tyr Gly Phe Lys
305                 310                 315                 320

Gly Ala Glu Ile Ala Met Ala Ser Tyr Cys Ser Glu Leu Gln Phe Leu
                325                 330                 335

Gly Asn Pro Val Thr Asn His Val Gln Ser Ala Glu Gln His Asn Gln
            340                 345                 350

Asp Val Asn Ser Leu Gly Leu Ile Ser Ala Arg Lys Thr Ala Glu Ala
        355                 360                 365

Ile Asp Ile Leu Lys Leu Met Ser Ser Thr Phe Leu Ile Ala Leu Cys
370                 375                 380

Gln Ala Ile Asp Leu Arg His Leu Glu Glu Asn Leu Lys Asn Thr Val
385                 390                 395                 400

Lys Asn Thr Val Ser Gln Ile Ala Lys Arg Val Leu Thr Met Gly Ser
                405                 410                 415

Asn Gly Glu Leu His Pro Ser Arg Phe Cys Glu Lys Asp Leu Leu Arg
            420                 425                 430

Val Val Asp Arg Glu His Leu Tyr Ala Tyr Ile Asp Asp Pro Cys Ser
        435                 440                 445

Ala Ser Tyr Pro Leu Met Gln Lys Leu Arg Gln Val Leu Val Asp His
    450                 455                 460

Ala Leu Met Asn Gly Asp Asn Glu Lys Asn Ser Thr Thr Ser Ile Phe
465                 470                 475                 480

Gln Lys Ile Gly Ala Phe Glu Glu Leu Lys Thr Leu Leu Pro Lys
                485                 490                 495

Glu Val Glu Ser Ala Arg Ile Glu Phe Glu Asn Gly Asn Ala Ala Ile
            500                 505                 510

Pro Asn Arg Ile Lys Glu Cys Arg Ser Tyr Pro Leu Tyr Lys Phe Val
        515                 520                 525

Arg Glu Val Leu Gly Thr Ser Leu Leu Thr Gly Glu Lys Val Ile Ser
    530                 535                 540

Pro Gly Glu Glu Cys Asp Lys Val Phe Ser Ala Ile Cys Ala Gly Lys
545                 550                 555                 560

Leu Ile Asp Pro Leu Phe Gln Cys Leu Lys Glu Trp Asn Gly Ala Pro
                565                 570                 575

Leu Pro Ile Cys
            580

<210> SEQ ID NO 44
<211> LENGTH: 3455
<212> TYPE: DNA
<213> ORGANISM: Corchorus olitorius
```

<400> SEQUENCE: 44

```
tgaaatttca aaacatcata ttttactagc gaattaaaat ttagatatag aggaacatta    60
aatggtaggc taaatatacc catttaatat tgcttgatca attaaaagat caaaatatta   120
atgtcgacga gattatttttt cagtccaata ttctatctat aaaaaagaaa aggaaaataa   180
aaaaacaact tttgacatta aatctttctt gatattcata tcttcttcag cagcttaaca   240
caaaatatca tgatgagagg caacctaaga ctgaatccga agtgattgtt cctcttgttg   300
tgctggcaga ggaagatgac ctttctcttg caagctcttc actgtttcat ataggcattg   360
cttcactgtg gtgaattcca accccaagtc cctcagcttt tggtttgtga acttgtaggg   420
ctttgctctt gggttcttct catccgagca cctgcatgga ttttttaattg taattatata   480
tcataattag ttatgaaaaa aggattgaga attcttatt aatactaata ttttctatta   540
gcgttcgagt ctattagaaa attcattctt gataattaaa actacgagtc cagtactcta   600
caatcagacc tgaccggtat gtatgagttt taatcatacg ttgttcacct aacttccatt   660
tctatcattc aaagacaaaa agcctaaagc tatcttagag agtgtggaat tttcaaagac   720
aattctcaaa ggagaaatgg gaggaccaat tttggccatt gttgcagccc ccatagttc    780
atagaaaatt ccaagaaaag aggccttttc ttcacccata tttcccttaa ttgggaaatc   840
tccatgattg aactactttg agtaggtgtg gatagaatag aatagaatat cattttcatt   900
tttatcctaa gtctcttgaa atgtttgttt tgaaagtgac attaggttag gtgaagttct   960
ctctgcacca ctactattta tactaactca gtatatagta taccatttac atttaatttt  1020
caacttgaaa aagaatagaa agaaaattca gtccaaaaaa cctacacttc ttcttgtagt  1080
aggtaagatt atgtcatttg tcaaaactgg tgtactcact gcccttcccc ttccccactc  1140
tgaattaaga aaaacaaatg aaaattgct gtccatgctt atccacttaa ttatcttcca   1200
ataatctttt caatggcttc tacatctat tcttatcttg tttttatttt ccttccaaat   1260
tttcttcttc tcctttata taggaagtgg tgatgtcatg agtgatgaga aaattcttta   1320
ataaaattca atgtcataat ctttaatatt attttctttt tcataatggg tttcacccttt  1380
ggatttcatt aagtttggtt tggacccatg attgccctcc acttttttctt caataattat  1440
ttattatatc attatacttt ttattttcct tttccatttt ctcaagaaat tctccttgtg  1500
aacttttaac aaactttaga agaaaccata tatctacc aagatgatga aagccaatat   1560
ttctaattcc aaatctacct ttggaagtaa aatcattttc atatatatat ttcttctaca  1620
tttttatgga ccatatatat ttaatcttga agatgagaac atcaaagttc ttcctgtcac  1680
tatcttccaa caaacaaagg ttgacattat atatttaacc aagttgtgga taatatctaa  1740
agccttggtt ttttattttc gaatattgtc gcacatttaa gacttagagc aagcaaatat  1800
atattgaata cgtgttgatg ttcaaattat tgacaattca aatgacccaa ttaaaacaat  1860
gaataagatt atcatctaat ctaagttttc aatttctttt ttgttttttaa gatttaggtg  1920
tgccactctt actataagaa acgtgttcat ataaataatt catttcaaag agaagtaaag  1980
ttaggttaaa gaaagtgaaa tgatctttcc ctctagatat ttctagatgt taaaataatg  2040
gaattcggct ccaaacttac cagaaattta gtgcaagccc ctctaaattt atttttttgt  2100
tctatttttt gtctataata atattaataa taactagaca tttggcttaa tctttggtac  2160
atgaacccctt aaatattccc ttatattctt ctaatgatat tccatgccat gtaaatctaa  2220
aagtggaccc taataaatcc tcagatatgt ctatttatta tgtttttgtt gactataatg  2280
```

-continued

| | |
|---|---:|
| acaacatatc gaacctgtta atgtttgtta gtatgatatt tttctcccct gtttgcaaat | 2340 |
| tggatagaaa aaattgcaag aagcaagttt acattattcc tctgcaaaca aggggtgtcc | 2400 |
| cacttaccta ctacagcact agaaaatcac taataaaatt tgattactat actaaaatta | 2460 |
| attcttaatt agcaatttt tgttaattaa gtatacttaa aaaggaaatt agagaaatta | 2520 |
| cttacttggt agggatggga tactcaggga agaacttggc aagaatgtcc accacctctc | 2580 |
| cacggtggag gacgctctcg gcgcagaggt aacggccgga ggcggaggga ttctcgaaga | 2640 |
| caagaatgtg tgctaatgca acatctctaa catgaacata ggcttgaact gaattggcat | 2700 |
| aggtctttgc agagccagtt aagtacttaa gaatgtgaat aatgctagca tttacagttg | 2760 |
| attgtagcaa tggaccaagc accaaaactg gagttattgt gactaagtca accccttttt | 2820 |
| ccttggctgt ttcccaggct gcctgctctg ccacagtctt cccataacaa taccaattct | 2880 |
| gcaattttg ttttaaacat gaaaatttgt taattaagga aaggaaatgt ttaattttgt | 2940 |
| gctaattata gaatgaaaat ggtggttaac ttaaatccct ttgttgtttc tattttgggt | 3000 |
| aggggagatt attaaattgg taatactaac aatagattgt agccataagt ttacacattc | 3060 |
| attgcattaa ttagccaaaa catgcatggt gttgggattt ttattactaa aacaaaaaag | 3120 |
| ggaaagacca atttggacat ttaaaacaag catttgatca ggtgatagac caagccagca | 3180 |
| aaaccagact ttttgtctgg ttccctgtcc ttccttaatt tcccagaaac agaacaggaa | 3240 |
| atttcctggt caaacacaag gtcagttaat tttgactttt caatactctc actaatcatt | 3300 |
| tatgttatga cccaccacta tttttaacat tggcctgttt attactatgt ttttaattaa | 3360 |
| atacgcgtga cttggattct taatttcaat taattatttg tgattagtgg attcaattcc | 3420 |
| tgataatctc aagtatttac ttaattaaga aggtg | 3455 |

<210> SEQ ID NO 45
<211> LENGTH: 969
<212> TYPE: DNA
<213> ORGANISM: Corchorus olitorius

<400> SEQUENCE: 45

| | |
|---|---:|
| atgtcgaagc aaggagaggc cgtgtgcgtt accggagcca gcggcgccat tggctcttgg | 60 |
| ctcgtcaagc tcctcctggc tcgcggttac actgtccacg gaaccgtcag aaatatcaag | 120 |
| gatgagaaag aaacgaagca tctagaatct ttggaaggag cagaatccg tctccgtctc | 180 |
| ttccagatcg atctcctcga ttatgatgca atctccgccg ctatcgaagg ctgcgctggc | 240 |
| gtcttccacc tcgcctcccc ctgcaccgtc gatcaagttc acgaccctca gaaggagctt | 300 |
| ttggatcctg caattaaagg aacactcaat gtactgacag ctgccaagga gctcggtgtt | 360 |
| aagcgcgtgg ttgtcacgtc ttctgtctcc tccataacac ctagtccgaa ctggcctgca | 420 |
| gataagatta aaacagagga ttgctggact gatattgact actgcaagca aaatgagtta | 480 |
| tggtatccaa tttccaaaac actggctgag aaggcagcat gggaattttc caaggagaaa | 540 |
| ggtttggatg tggtggtggt gaaccctggc actgtgatgg gtccaaatat tcctccaacc | 600 |
| cttactgcta gcatgtggat gttgttgcgc ctattgcaag gctgcacaga gacatatcaa | 660 |
| gactttttca tgggatctgt ccatttcaaa gatgttgcat tagcacatat tttggtgtat | 720 |
| gagaacccat cagcaagtgg aaggcacatg tgtcttgagg ccatatctca ttatggtgat | 780 |
| tttgtcgcca agttgctgaa actttacccct gaatataatg tgcccagttt gccgagggac | 840 |
| actcaacctg gactattaag ggctaagaat ggaggtcaaa agctgatgga tttgggggttg | 900 |
| gaattcattc ccatggaaca gataatcaaa gatgctgtcg agagtttaaa aagcaagggc | 960 | cttatttaa                                                                                                    969

<210> SEQ ID NO 46
<211> LENGTH: 322
<212> TYPE: PRT
<213> ORGANISM: Corchorus olitorius

<400> SEQUENCE: 46

Met Ser Lys Gln Gly Glu Ala Val Cys Val Thr Gly Ala Ser Gly Ala
1               5                   10                  15

Ile Gly Ser Trp Leu Val Lys Leu Leu Leu Ala Arg Gly Tyr Thr Val
            20                  25                  30

His Gly Thr Val Arg Asn Ile Lys Asp Glu Lys Glu Thr Lys His Leu
        35                  40                  45

Glu Ser Leu Glu Gly Ala Glu Ser Arg Leu Arg Leu Phe Gln Ile Asp
    50                  55                  60

Leu Leu Asp Tyr Asp Ala Ile Ser Ala Ala Ile Glu Gly Cys Ala Gly
65                  70                  75                  80

Val Phe His Leu Ala Ser Pro Cys Thr Val Asp Gln Val His Asp Pro
                85                  90                  95

Gln Lys Glu Leu Leu Asp Pro Ala Ile Lys Gly Thr Leu Asn Val Leu
            100                 105                 110

Thr Ala Ala Lys Glu Leu Gly Val Lys Arg Val Val Thr Ser Ser
        115                 120                 125

Val Ser Ser Ile Thr Pro Ser Pro Asn Trp Pro Ala Asp Lys Ile Lys
130                 135                 140

Thr Glu Asp Cys Trp Thr Asp Ile Asp Tyr Cys Lys Gln Asn Glu Leu
145                 150                 155                 160

Trp Tyr Pro Ile Ser Lys Thr Leu Ala Glu Lys Ala Ala Trp Glu Phe
                165                 170                 175

Ser Lys Glu Lys Gly Leu Asp Val Val Val Asn Pro Gly Thr Val
            180                 185                 190

Met Gly Pro Asn Ile Pro Pro Thr Leu Thr Ala Ser Met Trp Met Leu
        195                 200                 205

Leu Arg Leu Leu Gln Gly Cys Thr Glu Thr Tyr Gln Asp Phe Phe Met
    210                 215                 220

Gly Ser Val His Phe Lys Asp Val Ala Leu Ala His Ile Leu Val Tyr
225                 230                 235                 240

Glu Asn Pro Ser Ala Ser Gly Arg His Met Cys Leu Glu Ala Ile Ser
                245                 250                 255

His Tyr Gly Asp Phe Val Ala Lys Val Ala Glu Leu Tyr Pro Glu Tyr
            260                 265                 270

Asn Val Pro Ser Leu Pro Arg Asp Thr Gln Pro Gly Leu Leu Arg Ala
        275                 280                 285

Lys Asn Gly Gly Gln Lys Leu Met Asp Leu Gly Leu Glu Phe Ile Pro
    290                 295                 300

Met Glu Gln Ile Ile Lys Asp Ala Val Glu Ser Leu Lys Ser Lys Gly
305                 310                 315                 320

Leu Ile

<210> SEQ ID NO 47
<211> LENGTH: 787
<212> TYPE: DNA
<213> ORGANISM: Corchorus olitorius

<400> SEQUENCE: 47

```
tgcgatcgtg ccaaacccaa actggaatcc tcaaaccaac ggggccttcg atgagacatc    60
atggactgac ttggagtact gtaagagtcg acagaaatgg tatccagttt cgaagacgat   120
ggcagagaaa acagcatggg aatttgcaga gaagcatggg atggatgttg tggctataaa   180
cccagccacg tgtttaggcc ctctcttgca acccaacttg aatgccagct gcgctgtgtt   240
gttgcaattg ttggaaggat ccaaagatac ccaggaatac cattggttgg agctgtgca   300
tgttaaagat gtcgccaagg ctcagatttt gttgtttgag tctccttctg cttctggtag   360
atatctttgc accaatggca tttatcagtt tggaactttc gctgaaactg tctcccacct   420
cttccctcag tatcctgtcc acaggtttac tggagataca caacctggct tagtttcttg   480
caaagatgca gcaaagcgat taattgagct aggtctaatc ttcacccag ttgaagaagc    540
cgtccgagag accgtggaga gtctgcaagc caaaggcttc ttgaagcagc agcaaccatc   600
agagtcttag aaattaagtc tcttcttttt ttatcctttc tgtctctcaa aacagttaga   660
agctttatag tttatactag tttttaggt ttatttagct gtaggtaaag catggattca    720
atcagaagtt ttgtgcctaa agcttctatt attgtttcat tgtgataagt tataacaagt   780
ataaata                                                             787
```

<210> SEQ ID NO 48
<211> LENGTH: 202
<212> TYPE: PRT
<213> ORGANISM: Corchorus olitorius

<400> SEQUENCE: 48

```
Ala Ile Val Pro Asn Pro Asn Trp Asn Pro Gln Thr Asn Gly Ala Phe
1               5                   10                  15

Asp Glu Thr Ser Trp Thr Asp Leu Glu Tyr Cys Lys Ser Arg Gln Lys
            20                  25                  30

Trp Tyr Pro Val Ser Lys Thr Met Ala Glu Lys Thr Ala Trp Glu Phe
        35                  40                  45

Ala Glu Lys His Gly Met Asp Val Val Ala Ile Asn Pro Ala Thr Cys
    50                  55                  60

Leu Gly Pro Leu Leu Gln Pro Asn Leu Asn Ala Ser Cys Ala Val Leu
65                  70                  75                  80

Leu Gln Leu Leu Glu Gly Ser Lys Asp Thr Gln Glu Tyr His Trp Leu
                85                  90                  95

Gly Ala Val His Val Lys Asp Val Ala Lys Ala Gln Ile Leu Leu Phe
            100                 105                 110

Glu Ser Pro Ser Ala Ser Gly Arg Tyr Leu Cys Thr Asn Gly Ile Tyr
        115                 120                 125

Gln Phe Gly Thr Phe Ala Glu Thr Val Ser His Leu Phe Pro Gln Tyr
    130                 135                 140

Pro Val His Arg Phe Thr Gly Asp Thr Gln Pro Gly Leu Val Ser Cys
145                 150                 155                 160

Lys Asp Ala Ala Lys Arg Leu Ile Glu Leu Gly Leu Ile Phe Thr Pro
                165                 170                 175

Val Glu Glu Ala Val Arg Glu Thr Val Glu Ser Leu Gln Ala Lys Gly
            180                 185                 190

Phe Leu Lys Gln Gln Gln Pro Ser Glu Ser
        195                 200
```

<210> SEQ ID NO 49

```
<211> LENGTH: 1161
<212> TYPE: DNA
<213> ORGANISM: Corchorus olitorius

<400> SEQUENCE: 49
atggctcttc ttttcatcgt cccttttctta ctcctccttg gcctggtctc tcgacttcgg      60
cgaaaaccat tccctccggg gcccaaaggg ttaccaatca tcggaaacat gatgatgatg     120
gaccaattaa cccaccgtgg tctggccaag ctggccaaca aatacggcgg catattccat     180
atgaagatgg ggtatttaca tatggtcgcc gtttcaaatc ccgacatggc tcgccaagtt     240
ttgcaagttc aagacaacat tttctcaaac agaccagcca ccatagccat aagttattta     300
acttatgaca gagctgatat ggcttttgcc cattacggac cgttttggag acagatgcgt     360
aagctttgtg taatgaagct tttcagtcgg aaaagagccg aatcatggga gtctgtaaga     420
gatgaagttg attccatggt tcgaaccgtg tcggccaaca ctgggaaatc cattaatgtt     480
ggtgagttga tttttaacct tacgaaaaac attatttaca gggcggcttt tggttccagt     540
tcacaagaag acaagacga gttcatcgga atcttacaag agttttcgaa actgttcggt     600
gcttttaata ttgccgattt tatcccctgg ctgacgtggg ttgatcctca aggacttaac     660
aacaggctta gaacgctcg tcaagcttta gacaagttca tcgataccat tattgatgaa     720
catattcaga gaggaacaa caagaacaat gtttctgatg atgttgatac cgatatggtc     780
gatgatttgc ttgctttta cagtgaagaa gctaaagtaa atgaatcgga ggatcttcaa     840
aacgccatca gactcactag agaaaatatc aaagccatta tcatggacgt tatgtttgga     900
gggacagaga cggtggcatc agcaatagaa tgggccttat ctgagctgat gagaagccca     960
gaagatatga agagagtcca acaagagttg gctgacgtgg tgggtcttga ccggaaagtc    1020
gaagaatccg atttcgacaa actaaccttc cttaaatgca ctttgaaaga aaccctccgc    1080
ctccacccac caatcccact tctcctccat gagaccgccg aggacgccga ggtcggcgga    1140
tacagaatcc ccgccaagtc g                                              1161

<210> SEQ ID NO 50
<211> LENGTH: 387
<212> TYPE: PRT
<213> ORGANISM: Corchorus olitorius

<400> SEQUENCE: 50

Met Ala Leu Leu Phe Ile Val Pro Phe Leu Leu Leu Gly Leu Val
1               5                   10                  15

Ser Arg Leu Arg Arg Lys Pro Phe Pro Pro Gly Pro Lys Gly Leu Pro
            20                  25                  30

Ile Ile Gly Asn Met Met Met Met Asp Gln Leu Thr His Arg Gly Leu
        35                  40                  45

Ala Lys Leu Ala Asn Lys Tyr Gly Gly Ile Phe His Met Lys Met Gly
    50                  55                  60

Tyr Leu His Met Val Ala Val Ser Asn Pro Asp Met Ala Arg Gln Val
65                  70                  75                  80

Leu Gln Val Gln Asp Asn Ile Phe Ser Asn Arg Pro Ala Thr Ile Ala
                85                  90                  95

Ile Ser Tyr Leu Thr Tyr Asp Arg Ala Asp Met Ala Phe Ala His Tyr
            100                 105                 110

Gly Pro Phe Trp Arg Gln Met Arg Lys Leu Cys Val Met Lys Leu Phe
        115                 120                 125

Ser Arg Lys Arg Ala Glu Ser Trp Glu Ser Val Arg Asp Glu Val Asp
```

```
            130                 135                 140
Ser Met Val Arg Thr Val Ser Ala Asn Thr Gly Lys Ser Ile Asn Val
145                 150                 155                 160

Gly Glu Leu Ile Phe Asn Leu Thr Lys Asn Ile Ile Tyr Arg Ala Ala
                165                 170                 175

Phe Gly Ser Ser Gln Glu Gly Gln Asp Glu Phe Ile Gly Ile Leu
            180                 185                 190

Gln Glu Phe Ser Lys Leu Phe Gly Ala Phe Asn Ile Ala Asp Phe Ile
        195                 200                 205

Pro Trp Leu Thr Trp Val Asp Pro Gln Gly Leu Asn Asn Arg Leu Lys
    210                 215                 220

Asn Ala Arg Gln Ala Leu Asp Lys Phe Ile Asp Thr Ile Ile Asp Glu
225                 230                 235                 240

His Ile Gln Lys Arg Asn Asn Lys Asn Asn Val Ser Asp Val Asp
                245                 250                 255

Thr Asp Met Val Asp Asp Leu Leu Ala Phe Tyr Ser Glu Glu Ala Lys
            260                 265                 270

Val Asn Glu Ser Glu Asp Leu Gln Asn Ala Ile Arg Leu Thr Arg Glu
        275                 280                 285

Asn Ile Lys Ala Ile Ile Met Asp Val Met Phe Gly Gly Thr Glu Thr
    290                 295                 300

Val Ala Ser Ala Ile Glu Trp Ala Leu Ser Glu Leu Met Arg Ser Pro
305                 310                 315                 320

Glu Asp Met Lys Arg Val Gln Gln Glu Leu Ala Asp Val Val Gly Leu
                325                 330                 335

Asp Arg Lys Val Glu Glu Ser Asp Phe Asp Lys Leu Thr Phe Leu Lys
            340                 345                 350

Cys Thr Leu Lys Glu Thr Leu Arg Leu His Pro Pro Ile Pro Leu Leu
        355                 360                 365

Leu His Glu Thr Ala Glu Asp Ala Glu Val Gly Gly Tyr Arg Ile Pro
    370                 375                 380

Ala Lys Ser
385

<210> SEQ ID NO 51
<211> LENGTH: 1098
<212> TYPE: DNA
<213> ORGANISM: Corchorus olitorius

<400> SEQUENCE: 51
atgggttcaa ctggtgaaac caattcact ccaactcaag tctccgatga ggaagcaaac      60
ttgttcgcca tgcaattggc tagtgcctca gttcttccca tggtcctcaa atctgccata     120
gaacttgacc tacttgaagt catggccaag gctggacctg tgctttctt gtccccaaca     180 gaagtagctt cccaattgcc caccaagaac cctgatgcac ccgtcatgct cgaccgtatc     240
ttgcggctcc ttgctagtta ctccatttta acttgctcct taaggaatct tcctgatggc     300
aaagttgaga ggctctatgg ccttggccct gtctgtaaat acctggtcaa gaatgaagat     360
ggtgtcgctc tttccgccct taatctcatg aatcaagaca aggtcctaat ggagagctgg     420
tactacttga agatgcagt gttggaaggt ggaattccat tcaacaaggc ctatggcatg     480
accgcgttcg agtaccatgg cactgaccct agattcaaca aggttttcaa caggggaatg     540
tctgatcact caactatcac catgaagaag attctcgaga cctacgatgg attcgagggg     600
ctcaaaacat tggttgacgt tggtggtggt gttggtgcca cgcttaacat gatcgtctcc     660
```

```
aagcacccett ccattaaggg cattaacttt gatttgcctc atgtcattga ggatgctcca    720
gctcttcctg gtgttgagca tgttggtgga gatatgtttg taagtgttcc aaaaggagat    780
gccattttca tgaagtggat atgtcatgat tggagcgatg aacactgcgt aaaattcttg    840
aagaagtgct atgaagcttt gccagacaat gggaaagtca tcgttgccga atgcattctt    900
cctgattacc cagatgctag ccttgccaca aagctagttg ttcatatcga ttgtatcatg    960
ttggctcaca accctggtgg gaaagaaagg acagagaagg aatttgaagc cttggcaaag   1020
ggggcaggtt ttcaaggttt ccaagtaaag tgttgtgctt ttggcactta catcatggag   1080
ttcctcaaaa ctgttttaa                                                1098
```

<210> SEQ ID NO 52
<211> LENGTH: 365
<212> TYPE: PRT
<213> ORGANISM: Corchorus olitorius

<400> SEQUENCE: 52

```
Met Gly Ser Thr Gly Glu Thr Gln Phe Thr Pro Thr Gln Val Ser Asp
1               5                   10                  15

Glu Glu Ala Asn Leu Phe Ala Met Gln Leu Ala Ser Ala Ser Val Leu
            20                  25                  30

Pro Met Val Leu Lys Ser Ala Ile Glu Leu Asp Leu Leu Glu Val Met
        35                  40                  45

Ala Lys Ala Gly Pro Gly Ala Phe Leu Ser Pro Thr Glu Val Ala Ser
    50                  55                  60

Gln Leu Pro Thr Lys Asn Pro Asp Ala Pro Val Met Leu Asp Arg Ile
65                  70                  75                  80

Leu Arg Leu Leu Ala Ser Tyr Ser Ile Leu Thr Cys Ser Leu Arg Asn
                85                  90                  95

Leu Pro Asp Gly Lys Val Glu Arg Leu Tyr Gly Leu Gly Pro Val Cys
            100                 105                 110

Lys Tyr Leu Val Lys Asn Glu Asp Gly Val Ala Leu Ser Ala Leu Asn
        115                 120                 125

Leu Met Asn Gln Asp Lys Val Leu Met Glu Ser Trp Tyr Tyr Leu Lys
    130                 135                 140

Asp Ala Val Leu Glu Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Arg Gly Met Ser Asp His Ser Thr Ile Thr Met Lys Lys Ile Leu
            180                 185                 190

Glu Thr Tyr Asp Gly Phe Glu Gly Leu Lys Thr Leu Val Asp Val Gly
        195                 200                 205

Gly Gly Val Gly Ala Thr Leu Asn Met Ile Val Ser Lys His Pro Ser
    210                 215                 220

Ile Lys Gly Ile Asn Phe Asp Leu Pro His Val Ile Glu Asp Ala Pro
225                 230                 235                 240

Ala Leu Pro Gly Val Glu His Val Gly Gly Asp Met Phe Val Ser Val
                245                 250                 255

Pro Lys Gly Asp Ala Ile Phe Met Lys Trp Ile Cys His Asp Trp Ser
            260                 265                 270

Asp Glu His Cys Val Lys Phe Leu Lys Lys Cys Tyr Glu Ala Leu Pro
        275                 280                 285
```

Asp Asn Gly Lys Val Ile Val Ala Glu Cys Ile Leu Pro Asp Tyr Pro
    290                 295                 300

Asp Ala Ser Leu Ala Thr Lys Leu Val Val His Ile Asp Cys Ile Met
305                 310                 315                 320

Leu Ala His Asn Pro Gly Gly Lys Glu Arg Thr Glu Lys Glu Phe Glu
                325                 330                 335

Ala Leu Ala Lys Gly Ala Gly Phe Gln Gly Phe Gln Val Lys Cys Cys
                340                 345                 350

Ala Phe Gly Thr Tyr Ile Met Glu Phe Leu Lys Thr Val
            355                 360                 365

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gaatggggcg tttccatcta                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ttggcaacac attgaaacca                                                  20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
aagagctcag ggagcttact                                                  20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tctgccgtcg gattaagtga                                                  20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cttccaacgc caggatcata                                                  20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ctatgcttat tgcccaccct                                                20

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
aataccattg gttgggagct g                                              21

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggattcaatc agaagttttg tgcct                                          25

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccagccacca tagccataag                                                20

<210> SEQ ID NO 62
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
acagaatccc cgccaagt                                                  18

<210> SEQ ID NO 63
<211> LENGTH: 362
<212> TYPE: PRT
<213> ORGANISM: Populus trichocarpa

<400> SEQUENCE: 63

Met Ala Asp Lys Leu Pro Glu Glu His Pro Lys Pro Ala Phe Gly
1               5                   10                  15

Trp Ala Ala Arg Asp Gln Ser Gly Val Leu Ser Pro Phe Lys Phe Ser
            20                  25                  30

```
Arg Arg Ala Thr Gly Glu Lys Asp Val Ala Phe Lys Val Leu Tyr Cys
         35                  40                  45

Gly Ile Cys His Ser Asp Leu His Met Val Lys Asn Glu Trp Gly Val
     50                  55                  60

Thr Gln Tyr Pro Leu Ile Pro Gly His Glu Ile Val Gly Val Val Thr
 65                  70                  75                  80

Glu Val Gly Ser Lys Val Glu Lys Phe Lys Val Gly Asp Lys Val Gly
                 85                  90                  95

Val Gly Cys Met Val Gly Ser Cys Arg Ser Cys Asp Ser Cys Asp Asn
            100                 105                 110

Asn Leu Glu Asn Tyr Cys Ser Lys Lys Ile Leu Thr Tyr Gly Ala Lys
            115                 120                 125

Tyr Tyr Asp Gly Thr Val Thr Tyr Gly Gly Tyr Ser Asp Asn Met Val
        130                 135                 140

Ala Asp Glu His Phe Ile Val Arg Ile Pro Asn Asn Leu Pro Leu Asp
145                 150                 155                 160

Ala Gly Ala Pro Leu Leu Cys Ala Gly Ile Thr Val Tyr Ser Pro Leu
                165                 170                 175

Arg Tyr Phe Gly Leu Asp Lys Pro Gly Met His Val Gly Ile Val Gly
                180                 185                 190

Leu Gly Gly Leu Gly His Val Ala Val Lys Phe Ala Arg Ala Met Gly
        195                 200                 205

Val Lys Val Thr Val Ile Ser Thr Ser Pro Asn Lys Lys Gln Glu Ala
        210                 215                 220

Leu Glu Asn Leu Gly Ala Asp Ser Phe Leu Val Ser Arg Asp Gln Asp
225                 230                 235                 240

Gln Met Gln Ala Ala Met Gly Thr Leu Asp Gly Ile Ile Asp Thr Val
                245                 250                 255

Ser Ala Val His Pro Leu Leu Pro Leu Val Ala Leu Leu Lys Ser His
                260                 265                 270

Gly Lys Leu Val Leu Val Gly Ala Pro Glu Lys Pro Leu Glu Leu Pro
        275                 280                 285

Val Phe Pro Leu Ile Thr Gly Arg Lys Thr Val Gly Gly Ser Cys Val
        290                 295                 300

Gly Gly Ile Lys Glu Thr Gln Glu Met Ile Asp Phe Ala Ala Lys His
305                 310                 315                 320

Asn Ile Thr Ala Asp Ile Glu Val Ile Pro Met Asp Tyr Val Asn Thr
                325                 330                 335

Ala Met Glu Arg Val Leu Lys Ala Asp Val Arg Tyr Arg Phe Val Ile
                340                 345                 350

Asp Val Gly Lys Thr Leu Lys Pro Asp Val
        355                 360

<210> SEQ ID NO 64
<211> LENGTH: 362
<212> TYPE: PRT
<213> ORGANISM: Ricinus communis

<400> SEQUENCE: 64

Met Val Ala Asn Leu Pro Glu Lys Asp His Pro Arg Lys Ala Phe Gly
  1               5                  10                  15

Trp Ala Ala Arg Asp Gln Ser Gly Val Leu Ser Pro Phe Thr Phe Ser
                 20                  25                  30

Arg Arg Glu Thr Gly Glu Lys Asp Val Ser Phe Lys Val Leu Tyr Cys
```

```
        35                  40                  45
Gly Met Cys His Ser Asp Leu His Met Val Lys Asn Glu Trp Gly Thr
 50                  55                  60

Ser Thr Tyr Pro Leu Val Pro Gly His Glu Ile Val Gly Val Val Thr
 65                  70                  75                  80

Glu Val Gly Ser Lys Val Glu Lys Ile Lys Val Gly Asp Lys Val Gly
                 85                  90                  95

Val Gly Cys Met Val Gly Ser Cys Arg Ser Cys Asn Asn Cys Asn Lys
            100                 105                 110

Asp Leu Glu Asn Tyr Cys Pro Lys Met Ile Leu Thr Tyr Gly Ala Lys
        115                 120                 125

Tyr Tyr Asp Gly Thr Thr Thr Tyr Gly Gly Tyr Ser Asp Ile Met Val
    130                 135                 140

Ser Asp Glu His Phe Val Val Arg Ile Pro Asp Asn Leu Pro Leu Asp
145                 150                 155                 160

Ala Thr Ala Pro Leu Leu Cys Ala Gly Ile Thr Val Tyr Ser Pro Leu
                165                 170                 175

Lys Tyr Tyr Gly Leu Asp Lys Pro Gly Met Gln Leu Gly Val Val Gly
            180                 185                 190

Leu Gly Gly Leu Gly His Met Ala Val Lys Phe Ala Lys Ala Met Gly
        195                 200                 205

Ala Lys Val Thr Val Ile Ser Thr Ser Pro Asn Lys Lys Gln Glu Ala
    210                 215                 220

Ile Glu Arg Leu Gly Ala Asp Ser Phe Leu Val Ser Arg Asp Gln Asp
225                 230                 235                 240

Gln Met Lys Gly Ala Ile Gly Thr Met Asp Gly Ile Ile Asp Thr Val
                245                 250                 255

Ser Ala Met His Pro Leu Ser Pro Leu Ile Gly Leu Leu Lys Ser Asp
            260                 265                 270

Gly Lys Leu Val Leu Val Gly Ala Pro Glu Lys Pro Leu Glu Leu Pro
        275                 280                 285

Ala Phe Pro Leu Ile Gly Gly Arg Lys Leu Val Gly Gly Ser Cys Ile
    290                 295                 300

Gly Gly Met Lys Glu Thr Gln Glu Met Ile Asp Phe Ala Ala Lys His
305                 310                 315                 320

Ser Ile Thr Ala Asp Ile Glu Val Ile Pro Ala Asn Tyr Val Asn Thr
                325                 330                 335

Ala Met Glu Arg Met Leu Lys Asp Val Arg Tyr Arg Phe Val Ile
            340                 345                 350

Asp Ile Gly Asn Thr Leu Lys Pro Gly His
        355                 360

<210> SEQ ID NO 65
<211> LENGTH: 359
<212> TYPE: PRT
<213> ORGANISM: Fragaria x ananassa

<400> SEQUENCE: 65

Met Ser Ile Glu Gln Glu His Pro Asn Lys Ala Ser Gly Trp Ala Ala
 1               5                  10                  15

Arg Asp Ser Ser Gly Val Leu Ser Pro Phe Asn Phe Ser Arg Arg Glu
                20                  25                  30

Thr Gly Glu Lys Asp Val Met Phe Lys Val Leu Tyr Cys Gly Ile Cys
        35                  40                  45
```

His Ser Asp His His Met Val Lys Asn Glu Trp Gly Phe Ser Thr Tyr
     50                  55                  60

Pro Leu Val Pro Gly His Glu Ile Val Gly Glu Val Thr Glu Val Gly
 65                  70                  75                  80

Ser Lys Val Gln Lys Phe Lys Val Gly Asp Arg Val Gly Val Gly Cys
             85                  90                  95

Ile Val Gly Ser Cys Arg Ser Cys Glu Asn Cys Thr Asp His Leu Glu
            100                 105                 110

Asn Tyr Cys Pro Lys Gln Ile Leu Thr Tyr Gly Ala Asn Tyr Tyr Asp
            115                 120                 125

Gly Thr Thr Thr Tyr Gly Gly Cys Ser Asp Ile Met Val Ala His Glu
        130                 135                 140

His Phe Val Val Arg Ile Pro Asp Asn Leu Pro Leu Asp Gly Ala Ala
145                 150                 155                 160

Pro Leu Leu Cys Ala Gly Ile Thr Thr Tyr Ser Pro Leu Arg Tyr Phe
                165                 170                 175

Gly Leu Asp Lys Pro Gly Met His Val Gly Val Val Gly Leu Gly Gly
            180                 185                 190

Leu Gly His Val Ala Val Lys Phe Ala Lys Ala Met Gly Val Lys Val
        195                 200                 205

Thr Val Ile Ser Thr Ser Pro Lys Lys Glu Glu Ala Leu Lys His
210                 215                 220

Leu Gly Ala Asp Ser Phe Leu Val Ser Arg Asp Gln Asp His Met Gln
225                 230                 235                 240

Ala Ala Ile Gly Thr Met Asp Gly Ile Ile Asp Thr Val Ser Ala Gln
                245                 250                 255

His Pro Leu Leu Pro Leu Ile Gly Leu Leu Lys Ser His Gly Lys Leu
            260                 265                 270

Val Met Val Gly Ala Pro Glu Lys Pro Leu Glu Leu Pro Val Phe Pro
        275                 280                 285

Leu Leu Met Gly Arg Lys Met Val Ala Gly Ser Gly Ile Gly Gly Met
290                 295                 300

Met Glu Thr Gln Glu Met Ile Asp Phe Ala Ala Lys His Asn Ile Thr
305                 310                 315                 320

Ala Asp Ile Glu Val Ile Pro Ile Asp Tyr Leu Asn Thr Ala Met Glu
                325                 330                 335

Arg Leu Val Lys Ala Asp Val Arg Tyr Arg Phe Val Ile Asp Ile Gly
            340                 345                 350

Asn Thr Leu Lys Ala Ser Ser
        355

<210> SEQ ID NO 66
<211> LENGTH: 362
<212> TYPE: PRT
<213> ORGANISM: Populus trichocarpa

<400> SEQUENCE: 66

Met Ser Lys Ser Pro Glu Glu Glu His Pro Val Lys Ala Phe Gly Trp
 1               5                  10                  15

Ala Ala Arg Asp Gln Ser Gly His Leu Ser Pro Phe Asn Phe Ser Arg
            20                  25                  30

Arg Ala Thr Gly Glu Glu Asp Val Arg Phe Lys Val Leu Tyr Cys Gly
         35                 40                  45

Ile Cys His Ser Asp Leu His Ser Ile Lys Asn Asp Trp Gly Phe Ser
 50                  55                  60

```
Met Tyr Pro Leu Val Pro Gly His Glu Ile Val Gly Glu Val Thr Glu
 65                  70                  75                  80

Val Gly Ser Lys Val Lys Lys Val Asn Val Gly Asp Lys Val Gly Val
                 85                  90                  95

Gly Cys Leu Val Gly Ala Cys His Ser Cys Glu Ser Cys Ala Ser Asp
            100                 105                 110

Leu Glu Asn Tyr Cys Pro Lys Met Ile Leu Thr Tyr Ala Ser Ile Tyr
        115                 120                 125

His Asp Gly Thr Ile Thr Tyr Gly Gly Tyr Ser Asp His Met Val Ala
130                 135                 140

Asn Glu Arg Tyr Ile Ile Arg Phe Pro Asp Asn Met Pro Leu Asp Gly
145                 150                 155                 160

Gly Ala Pro Leu Leu Cys Ala Gly Ile Thr Val Tyr Ser Pro Leu Lys
                165                 170                 175

Tyr Phe Gly Leu Asp Glu Pro Gly Lys His Ile Gly Ile Val Gly Leu
            180                 185                 190

Gly Gly Leu Gly His Val Ala Val Lys Phe Ala Lys Ala Phe Gly Ser
        195                 200                 205

Lys Val Thr Val Ile Ser Thr Ser Pro Ser Lys Lys Glu Glu Ala Leu
210                 215                 220

Lys Asn Leu Gly Ala Asp Ser Phe Leu Val Ser Arg Asp Gln Glu Gln
225                 230                 235                 240

Met Gln Ala Ala Ala Gly Thr Leu Asp Gly Ile Ile Asp Thr Val Ser
                245                 250                 255

Ala Val His Pro Leu Leu Pro Leu Phe Gly Leu Leu Lys Ser His Gly
            260                 265                 270

Lys Leu Ile Leu Val Gly Ala Pro Glu Lys Pro Leu Glu Leu Pro Ala
        275                 280                 285

Phe Ser Leu Ile Ala Gly Arg Lys Thr Val Ala Gly Ser Gly Ile Gly
290                 295                 300

Gly Met Lys Glu Thr Gln Glu Met Ile Asp Phe Ala Ala Lys His Asn
305                 310                 315                 320

Ile Thr Ala Asp Ile Glu Val Ile Ser Thr Asp Tyr Leu Asn Thr Ala
                325                 330                 335

Met Glu Arg Leu Ala Lys Asn Asp Val Arg Tyr Arg Phe Val Ile Asp
            340                 345                 350

Val Gly Asn Thr Leu Ala Ala Thr Lys Pro
        355                 360

<210> SEQ ID NO 67
<211> LENGTH: 359
<212> TYPE: PRT
<213> ORGANISM: Gossypium hirsutum

<400> SEQUENCE: 67

Met Ala Leu Glu Thr Pro Asn His Thr Gln Thr Val Ala Gly Trp Ala
 1               5                  10                  15

Ala Tyr Asp Ser Ser Gly Lys Ile Ala Pro Tyr Ile Phe Lys Arg Arg
                20                  25                  30

Glu Asn Gly Val Asn Asp Val Thr Ile Gln Val Met Tyr Cys Gly Ile
            35                  40                  45

Cys His Thr Asp Leu His His Val Lys Asp Asp Trp Gly Ile Thr Met
        50                  55                  60

Tyr Pro Val Val Pro Gly His Glu Ile Thr Gly Val Ile Thr Lys Val
```

```
                65                  70                  75                  80
        Gly Ser Asn Val Lys Asn Phe Lys Leu Gly Asp Arg Val Gly Val Gly
                        85                  90                  95

Cys Leu Ala Ala Ser Cys Leu Glu Cys Glu Phe Cys Lys Asn Ser Gln
                        100                 105                 110

Glu Asn Tyr Cys Asp Gln Ile Gln Phe Thr Tyr Asn Gly Ile Phe Trp
                        115                 120                 125

Asp Gly Ser Ile Thr Tyr Gly Gly Tyr Ser Glu Met Leu Val Ala Asp
                        130                 135                 140

His Arg Tyr Val Val His Val Pro Asp Asn Leu Pro Met Asp Ala Ala
        145                 150                 155                 160

Ala Pro Leu Leu Cys Ala Gly Ile Thr Val Phe Ser Pro Met Lys Asp
                        165                 170                 175

Cys Gln Leu Leu Glu Ser Pro Gly Lys Lys Val Gly Ile Val Gly Leu
                        180                 185                 190

Gly Gly Leu Gly His Val Ala Val Lys Met Ala Lys Ala Phe Gly His
                        195                 200                 205

Gln Val Thr Val Ile Ser Thr Ser Pro Ser Lys Glu Asn Glu Ala Lys
                        210                 215                 220

Gln Arg Leu Gly Ala Asp Tyr Phe Leu Val Ser Thr Asp Ala Lys Gln
        225                 230                 235                 240

Met Gln Arg Gly Lys Arg Thr Leu Asp Val Ile Leu Asp Thr Val Ser
                        245                 250                 255

Ala Lys His Ser Leu Gly Pro Ile Leu Glu Leu Leu Lys Val Asn Gly
                        260                 265                 270

Thr Leu Val Val Val Gly Ala Pro Asp Arg Pro Ile Glu Leu Pro Ser
                        275                 280                 285

Phe Pro Leu Ile Phe Gly Lys Arg Ala Val Lys Gly Ser Met Thr Gly
                        290                 295                 300

Gly Met Lys Glu Thr Gln Glu Met Met Asp Val Cys Gly Lys His Asn
        305                 310                 315                 320

Ile Thr Cys Asp Val Glu Leu Ile Lys Pro Asp Lys Ile Asn Gln Ala
                        325                 330                 335

Leu Asp Arg Leu Ala Arg Asn Asp Val Arg Tyr Arg Phe Val Ile Asp
                        340                 345                 350

Ile Ala Gly Thr Ser Lys Leu
                        355

<210> SEQ ID NO 68
<211> LENGTH: 357
<212> TYPE: PRT
<213> ORGANISM: Gossypium hirsutum

<400> SEQUENCE: 68

Met Gly Ser Leu Glu Thr Glu Arg Thr Thr Gly Trp Ala Ala Arg
1               5                   10                  15

Asp Pro Ser Gly Val Leu Ser Pro Tyr Thr Tyr Thr Leu Arg Asn Thr
                20                  25                  30

Gly Pro Glu Asp Val Phe Val Lys Val Met Cys Cys Gly Ile Cys His
                35                  40                  45

Thr Asp Leu His Gln Ala Lys Asn Asp Leu Gly Met Ser Asn Tyr Pro
        50                  55                  60

Met Val Pro Gly His Glu Val Val Gly Glu Val Leu Glu Val Gly Ser
65                  70                  75                  80
```

```
Asp Val Ser Lys Phe Arg Val Gly Asp Ile Val Gly Val Gly Cys Leu
                85                  90                  95

Val Gly Cys Cys Arg Asn Cys Arg Pro Cys Asp Ser Asp Asn Glu Gln
            100                 105                 110

Tyr Cys Leu Lys Lys Ile Trp Ser Tyr Asn Asp Val Tyr Thr Asp Gly
            115                 120                 125

Lys Pro Thr Gln Gly Gly Phe Ala Gly Ser Met Val Val Asp Gln Lys
            130                 135                 140

Phe Val Val Lys Ile Pro Glu Gly Met Ala Pro Glu Gln Val Ala Pro
145                 150                 155                 160

Leu Leu Cys Ala Gly Val Thr Val Tyr Ser Pro Leu Asn His Phe Gly
                165                 170                 175

Leu Met Gly Ser Gly Leu Arg Gly Gly Ile Leu Gly Leu Gly Gly Val
                180                 185                 190

Gly His Met Gly Val Lys Ile Ala Lys Ala Met Gly His His Val Thr
            195                 200                 205

Val Ile Ser Ser Ser Asp Lys Lys Val Glu Ala Leu Glu His Leu
            210                 215                 220

Gly Ala Asp Asp Tyr Leu Val Ser Ser Asp Ala Glu Gly Met Gln Lys
225                 230                 235                 240

Ala Ala Asp Ser Leu Asp Tyr Ile Ile Asp Thr Val Pro Val Phe His
                245                 250                 255

Pro Leu Glu Pro Tyr Leu Ser Leu Leu Lys Phe Asp Gly Lys Leu Ile
                260                 265                 270

Leu Thr Gly Val Ile Asn Thr Pro Leu Gln Phe Val Ser Pro Met Val
            275                 280                 285

Met Leu Gly Arg Lys Ser Ile Thr Gly Ser Phe Ile Gly Ser Met Lys
            290                 295                 300

Glu Thr Glu Glu Met Leu Asn Phe Cys Lys Glu Gln Asn Leu Thr Ser
305                 310                 315                 320

Met Ile Glu Val Val Lys Met Asp Tyr Ile Asn Thr Ala Met Glu Arg
                325                 330                 335

Leu Glu Lys Asn Asp Val Arg Tyr Arg Phe Val Val Asp Val Ala Gly
            340                 345                 350

Ser Lys Leu Asp Gln
            355

<210> SEQ ID NO 69
<211> LENGTH: 355
<212> TYPE: PRT
<213> ORGANISM: Gossypium hirsutum

<400> SEQUENCE: 69

Met Asp Ser Gln Thr Lys Thr Glu Asn Cys Leu Gly Trp Ala Ala Thr
1               5                   10                  15

Asp Pro Thr Gly Val Leu Ser Pro Tyr Lys Phe Ser Arg Arg Pro Leu
            20                  25                  30

Gly Ser Asp Asp Val Ser Ile Lys Ile Thr His Cys Gly Val Cys Tyr
            35                  40                  45

Ala Asp Val Ile Trp Ser Arg Asn Met Phe Gly Asp Ser Ile Tyr Pro
            50                  55                  60

Leu Val Pro Gly His Glu Ile Ala Gly Ile Val Lys Glu Val Gly Ser
65                  70                  75                  80

Asn Val Gln Arg Ile Lys Val Gly Asp Leu Val Gly Val Gly Thr Tyr
                85                  90                  95
```

-continued

Val Asn Ser Cys Arg Asn Cys Glu Tyr Cys Asn Asp Gly Val Glu Val
              100                 105                 110

Gln Cys Val Lys Gly Pro Val Leu Thr Phe Asn His Ile Asp Ile Asp
            115                 120                 125

Gly Thr Val Thr Lys Gly Gly Tyr Ser Ser His Ile Val Val His Glu
        130                 135                 140

Arg Tyr Cys Phe Lys Ile Pro Asn Asn Tyr Pro Leu Ala Ser Ala Ala
145                 150                 155                 160

Pro Leu Leu Cys Ala Gly Ile Thr Val Tyr Thr Pro Met Met Arg Tyr
                165                 170                 175

Asn Met Asn Gln Pro Gly Lys Ser Leu Gly Val Ile Gly Leu Gly Gly
            180                 185                 190

Leu Gly His Met Ala Val Lys Phe Gly Lys Ala Phe Gly Leu Ser Val
        195                 200                 205

Thr Val Leu Ser Thr Ser Ile Ser Lys Lys Glu Glu Ala Leu Ser Leu
    210                 215                 220

Leu Gly Ala Asp Asn Phe Val Val Thr Ser Asp Gln Glu Gln Met Lys
225                 230                 235                 240

Gly Leu Ser Lys Ser Leu Asp Phe Ile Ile Asp Thr Ala Ser Gly Asp
                245                 250                 255

His Pro Phe Asp Pro Tyr Leu Ser Leu Leu Lys Ser Ala Gly Val Tyr
            260                 265                 270

Ala Leu Val Gly Phe Pro Ser Glu Ile Lys Phe Ser Pro Ala Ser Leu
        275                 280                 285

Asn Pro Gly Met Lys Thr Phe Ala Gly Ser Val Thr Gly Gly Thr Lys
    290                 295                 300

Met Ile Gln Glu Met Ile Gly Phe Cys Ala Ala Arg Lys Ile Tyr Pro
305                 310                 315                 320

Gln Ile Glu Val Ile Pro Ile Gln Tyr Ala Asn Glu Ala Leu Glu Arg
                325                 330                 335

Leu Val Lys Lys Asp Val Lys Tyr Arg Phe Val Ile Asp Ile Glu Asn
            340                 345                 350

Thr Leu Lys
        355

<210> SEQ ID NO 70
<211> LENGTH: 248
<212> TYPE: PRT
<213> ORGANISM: Gossypium hirsutum

<400> SEQUENCE: 70

Met Ala Thr Asn Thr Thr Gln Glu Gln Gln Pro Ala Ala Gly Arg His
1               5                   10                  15

Gln Glu Val Gly His Lys Ser Leu Leu Gln Ser Asp Ala Leu Tyr Gln
            20                  25                  30

Tyr Ile Leu Glu Thr Ser Val Tyr Pro Met Glu Pro Glu Pro Met Lys
        35                  40                  45

Glu Leu Arg Glu Leu Thr Ala Lys His Pro Trp Asn Leu Met Thr Thr
    50                  55                  60

Ser Ala Asp Glu Gly Gln Phe Leu Asn Met Leu Leu Lys Leu Ile Asn
65                  70                  75                  80

Ala Lys Asn Thr Met Glu Ile Gly Val Tyr Thr Gly Tyr Ser Leu Leu
                85                  90                  95

Ala Thr Ala Leu Ala Leu Pro Asp Asp Gly Lys Ile Leu Ala Met Asp

```
            100                 105                 110
Ile Asn Arg Glu Asn Tyr Glu Leu Gly Leu Pro Val Ile Arg Lys Ala
            115                 120                 125

Gly Val Ala His Lys Ile Glu Phe Lys Glu Gly Pro Ala Met Pro Val
            130                 135                 140

Leu Asp Lys Leu Val Glu Asp Lys Asn His Gly Ser Tyr Asp Phe
145                 150                 155                 160

Ile Phe Val Asp Ala Asp Lys Asp Asn Tyr Leu Asn Tyr His Lys Arg
                    165                 170                 175

Leu Ile Glu Leu Val Lys Val Gly Gly Leu Ile Gly Tyr Asp Asn Thr
                    180                 185                 190

Leu Trp Asn Gly Ser Val Val Ala Pro Pro Asp Ala Pro Leu Arg Lys
                    195                 200                 205

Tyr Val Arg Tyr Tyr Arg Asp Phe Val Leu Glu Leu Asn Lys Ala Leu
                    210                 215                 220

Ala Val Asp Pro Arg Ile Glu Ile Cys Met Leu Pro Val Gly Asp Gly
225                 230                 235                 240

Ile Thr Leu Cys Arg Arg Val Lys
                    245

<210> SEQ ID NO 71
<211> LENGTH: 247
<212> TYPE: PRT
<213> ORGANISM: Populus tremuloides

<400> SEQUENCE: 71

Met Ala Thr Asn Gly Glu Glu Gln Gln Ser Gln Ala Gly Arg His Gln
1               5                   10                  15

Glu Val Gly His Lys Ser Leu Leu Gln Ser Asp Ala Leu Tyr Gln Tyr
                20                  25                  30

Ile Leu Glu Thr Ser Val Tyr Pro Arg Glu Pro Glu Cys Met Lys Glu
                35                  40                  45

Leu Arg Glu Val Thr Ala Lys His Pro Trp Asn Ile Met Thr Thr Ser
50                  55                  60

Ala Asp Glu Gly Gln Phe Leu Asn Met Leu Leu Lys Leu Val Asn Ala
65                  70                  75                  80

Lys Asn Thr Met Glu Ile Gly Val Tyr Thr Gly Tyr Ser Leu Leu Ala
                85                  90                  95

Thr Ala Leu Ala Ile Pro Glu Asp Gly Lys Ile Leu Ala Met Asp Ile
                100                 105                 110

Asn Arg Glu Asn Tyr Glu Leu Gly Leu Pro Val Ile Gln Lys Ala Gly
                115                 120                 125

Val Ala His Lys Ile Asp Phe Lys Glu Gly Pro Ala Leu Pro Val Leu
                130                 135                 140

Asp Gln Met Ile Glu Asp Gly Lys Tyr His Gly Ser Phe Asp Phe Ile
145                 150                 155                 160

Phe Val Asp Ala Asp Lys Asp Asn Tyr Ile Asn Tyr His Lys Arg Leu
                    165                 170                 175

Ile Glu Leu Val Lys Val Gly Gly Leu Ile Gly Tyr Asp Asn Thr Leu
                    180                 185                 190

Trp Asn Gly Ser Val Val Ala Pro Pro Asp Ala Pro Met Arg Lys Tyr
                    195                 200                 205

Val Arg Tyr Tyr Arg Asp Phe Val Leu Glu Leu Asn Lys Ala Leu Ala
                    210                 215                 220
```

```
Ala Asp Pro Arg Ile Glu Ile Cys Met Leu Pro Val Gly Asp Gly Ile
225                 230                 235                 240

Thr Leu Cys Arg Arg Ile Gln
                245

<210> SEQ ID NO 72
<211> LENGTH: 366
<212> TYPE: PRT
<213> ORGANISM: Gossypium hirsutum

<400> SEQUENCE: 72

Met Gly Ser Ile Gly Glu Thr Gln Met Thr Pro Thr Gln Val Ser Asp
1               5                   10                  15

Asp Glu Ala Asn Leu Phe Ala Met Gln Leu Ala Ser Ala Ser Val Leu
                20                  25                  30

Pro Met Val Leu Lys Ser Ala Ile Glu Leu Asp Leu Glu Ile Met
            35                  40                  45

Ala Lys Ala Gly Pro Gly Ala Phe Leu Ser Pro Lys Glu Val Ala Ser
50                  55                  60

Lys Leu Pro Thr Thr Asn Pro Asp Ala Pro Val Met Leu Asp Arg Ile
65                  70                  75                  80

Leu Arg Leu Leu Ala Ser Tyr Asn Val Leu Thr Cys Ser Leu Arg Thr
                85                  90                  95

Phe Pro Gly Gly Lys Val Glu Arg Leu Tyr Gly Leu Gly Pro Val Cys
            100                 105                 110

Lys Phe Leu Thr Arg Asn Glu Asp Gly Val Thr Leu Ser Ala Leu Ser
        115                 120                 125

Leu Met Asn Gln Asp Lys Val Leu Met Glu Ser Trp Tyr Tyr Leu Lys
130                 135                 140

Asp Ala Val Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175

Asn Arg Gly Met Ser Asp His Ser Thr Ile Thr Met Lys Lys Ile Leu
            180                 185                 190

Asp Thr Tyr Asp Gly Phe Gln Gly Leu Lys Thr Leu Val Asp Val Gly
        195                 200                 205

Gly Gly Thr Gly Ala Thr Leu Ser Met Ile Val Ser Lys Tyr Pro Thr
210                 215                 220

Ile Lys Gly Ile Asn Phe Asp Leu Pro His Val Ile Glu Asp Ala Pro
225                 230                 235                 240

Ser Cys Pro Val Gly Val Glu His Val Gly Gly Asp Met Phe Val Ser
                245                 250                 255

Val Pro Lys Gly Asp Ala Ile Phe Met Lys Trp Ile Cys His Asp Trp
            260                 265                 270

Ser Asp Glu His Cys Ala Lys Phe Leu Lys Asn Cys Tyr Glu Ala Leu
        275                 280                 285

Pro Asp Asn Gly Lys Val Ile Val Ala Glu Cys Ile Leu Pro Asp Tyr
290                 295                 300

Pro Asp Pro Ser Leu Ala Thr Lys Leu Val Val His Ile Asp Cys Ile
305                 310                 315                 320

Met Leu Ala His Asn Pro Gly Gly Lys Glu Arg Thr Ala Lys Glu Phe
                325                 330                 335

Glu Ala Leu Ala Lys Gly Ala Gly Phe Gln Gly Phe Gln Ile Thr Cys
            340                 345                 350
```

```
Ser Ala Phe Gly Thr Asn Ile Met Glu Phe Leu Lys Ser Val
        355                 360                 365

<210> SEQ ID NO 73
<211> LENGTH: 545
<212> TYPE: PRT
<213> ORGANISM: Corchorus capsularis

<400> SEQUENCE: 73

Met Ala Pro Gln Ala Pro Glu Leu Pro Gln Glu Asp Phe Ile Phe Arg
1               5                   10                  15

Ser Lys Leu Pro Asp Ile Tyr Ile Pro Lys His Leu Pro Leu His Ser
            20                  25                  30

Tyr Cys Phe Glu Asn Ile Ser Lys Val Ala Ser Lys Pro Cys Leu Ile
        35                  40                  45

Asn Gly Thr Thr Gly Gln Ile Tyr Thr Tyr Glu Glu Val Glu Leu Thr
    50                  55                  60

Ala Arg Arg Val Ala Ala Gly Leu His Lys Leu Gly Val Gln Gln Arg
65                  70                  75                  80

Gln Val Ile Met Leu Leu Leu Pro Asn Thr Pro Glu Phe Val Leu Ser
                85                  90                  95

Phe Leu Gly Ala Ser Phe Leu Gly Ala Val Cys Thr Ala Ala Asn Pro
            100                 105                 110

Phe Phe Thr Ala Pro Glu Val Ala Lys Gln Ala Lys Ala Ser Asn Ala
        115                 120                 125

Arg Ile Ile Ile Thr Gln Ala Ser Tyr Val Asp Lys Val Lys Glu Phe
    130                 135                 140

Ala Gln Glu Asn Val Asp Val Lys Val Met Cys Ile Asp Ser Ala Pro
145                 150                 155                 160

Glu Gly Cys Leu His Phe Ser Glu Leu Thr Gln Ala Asp Glu Asn Asp
                165                 170                 175

Leu Pro Glu Val Glu Ile Asn Pro Asp Asp Val Val Ala Leu Pro Tyr
            180                 185                 190

Ser Ser Gly Thr Thr Gly Leu Pro Lys Gly Val Met Leu Thr His Lys
        195                 200                 205

Gly Leu Val Thr Ser Val Ala Gln Gln Val Asp Gly Glu Asn Pro Asn
    210                 215                 220

Leu Tyr Phe His Ser Asp Asp Val Ile Leu Cys Thr Leu Pro Leu Phe
225                 230                 235                 240

His Ile Tyr Ala Leu Asn Ser Ile Met Leu Cys Gly Leu Arg Ala Gly
                245                 250                 255

Ala Ala Ile Leu Ile Met Gln Lys Phe Glu Ile Gly Leu Leu Leu Asp
            260                 265                 270

Leu Ile Gln Lys Tyr Lys Ile Thr Ile Ala Pro Met Val Pro Pro Ile
        275                 280                 285

Val Leu Ala Ile Ala Lys Ser Ser Glu Thr Glu Lys Tyr Asp Leu Ser
    290                 295                 300

Ser Ile Arg Met Val Lys Ser Gly Ala Ala Pro Leu Gly Lys Glu Leu
305                 310                 315                 320

Glu Asp Ala Val Arg Ala Lys Phe Pro Gly Ala Lys Leu Gly Gln Gly
                325                 330                 335

Tyr Gly Met Thr Glu Ala Gly Pro Val Leu Ala Met Cys Leu Gly Phe
            340                 345                 350

Ala Lys Glu Pro Phe Glu Ile Lys Ser Gly Ala Cys Gly Thr Val Val
```

355                 360                 365
Arg Asn Ala Glu Met Lys Ile Val Asp Pro Asp Thr Gly Ala Ser Leu
    370                 375                 380

Pro Arg Asn Gln Ala Gly Glu Ile Cys Ile Arg Gly Asp Gln Ile Met
385                 390                 395                 400

Lys Gly Tyr Leu Asn Asp Pro Glu Ala Thr Ala Arg Thr Ile Asp Lys
                405                 410                 415

Asp Gly Trp Leu His Thr Gly Asp Ile Gly Tyr Ile Asp Asp Asp
            420                 425                 430

Glu Leu Phe Ile Val Asp Arg Leu Lys Glu Leu Ile Lys Tyr Lys Gly
            435                 440                 445

Phe Gln Val Ala Pro Ala Glu Leu Glu Ala Met Leu Ile Ala His Pro
            450                 455                 460

Glu Ile Ile Asp Ala Ala Val Val Ala Met Lys Asp Glu Val Ala Gly
465                 470                 475                 480

Glu Val Pro Val Ala Phe Val Val Lys Ser Glu Lys Ser Glu Ile Thr
                485                 490                 495

Glu Asp Glu Ile Lys Gln Tyr Ile Ser Lys Gln Val Val Phe Tyr Lys
                500                 505                 510

Arg Ile Ser Arg Val Phe Phe Met Glu Ala Ile Pro Lys Ala Pro Ser
            515                 520                 525

Gly Lys Ile Leu Arg Lys Glu Leu Arg Ala Lys Leu Ala Ser Gly Asn
530                 535                 540

Tyr
545

<210> SEQ ID NO 74
<211> LENGTH: 542
<212> TYPE: PRT
<213> ORGANISM: Ricinus communis

<400> SEQUENCE: 74

Met Glu Lys Ser Gly Tyr Gly Arg Asp Gly Ile Tyr Arg Ser Leu Arg
1               5                   10                  15

Pro Leu Leu Val Leu Pro Lys Asp Pro Asn Leu Ser Met Val Ser Phe
                20                  25                  30

Leu Phe Arg Asn Cys Asn Ser Tyr Pro His Lys Pro Ala Leu Ile Asp
            35                  40                  45

Ala Asp Leu Ser Lys Thr Leu Ser Phe Ser Gln Leu Lys Ser Ile Val
    50                  55                  60

Ile Lys Val Ser His Gly Leu Leu Lys Leu Gly Ile Ser Lys Asn Asp
65                  70                  75                  80

Val Val Leu Ile Phe Ala Pro Asn Ser Tyr Gln Phe Pro Ile Cys Phe
                85                  90                  95

Leu Ala Ile Thr Ser Ile Gly Ala Ile Ala Thr Thr Ala Asn Pro Leu
                100                 105                 110

Tyr Thr Thr Thr Glu Ile Ser Lys Gln Ile Lys Asp Ser Asn Pro Lys
            115                 120                 125

Leu Val Ile Thr Val Pro Glu Leu Trp Asn Lys Val Lys Asp Phe Asn
    130                 135                 140

Leu Pro Ala Val Phe Leu Gly Ala Lys Glu Ser Leu Leu Ile Glu Pro
145                 150                 155                 160

Asn Ser Arg Ile Lys Ser Phe Asp His Leu Val Glu Leu Gly Gly Ser
                165                 170                 175

Asn Ser Glu Phe Pro Thr Ile Asn Val Lys Gln Thr Asp Ile Ala Thr
            180                 185                 190

Leu Leu Tyr Ser Ser Gly Thr Thr Gly Ile Ser Lys Gly Val Ile Leu
        195                 200                 205

Thr His Gly Asn Phe Ile Ala Ala Ser Gln Met Ile Thr Met Asp Gln
    210                 215                 220

Glu Ile Ala Gly Glu Leu His Asn Val Phe Leu Cys Phe Leu Pro Met
225                 230                 235                 240

Phe His Val Phe Gly Leu Ala Val Ile Ala Tyr Ser Gln Leu Gln Thr
                245                 250                 255

Gly Asn Ala Val Val Ser Met Gly Lys Phe Asp Phe Glu Leu Val Leu
            260                 265                 270

Lys Ala Val Glu Lys Tyr Arg Ile Thr His Leu Trp Val Val Pro Pro
        275                 280                 285

Val Ile Leu Ala Leu Ala Lys Gln Ser Leu Val Lys Lys Tyr Asp Leu
    290                 295                 300

Ser Ser Leu Gln His Val Gly Ser Gly Ala Ala Pro Leu Ser Lys Glu
305                 310                 315                 320

Leu Met Glu Glu Cys Ala Lys Thr Ile Pro His Ala Ala Ile Ala Gln
                325                 330                 335

Gly Tyr Gly Met Thr Glu Thr Thr Gly Ile Val Ser Val Glu Asn Pro
            340                 345                 350

Arg Ile Gly Val Arg His Ser Gly Ser Ala Gly Thr Leu Ala Ala Gly
        355                 360                 365

Ile Glu Ala Gln Ile Ile Ser Val Asp Thr Leu Lys Pro Leu Pro Pro
    370                 375                 380

Asn Gln Leu Gly Glu Ile Trp Val Arg Gly Pro Asn Met Met Arg Gly
385                 390                 395                 400

Tyr Phe Asn Asn Pro Gln Ala Thr Lys Gln Thr Ile Asp Lys Lys Gly
                405                 410                 415

Trp Leu His Thr Gly Asp Leu Gly Tyr Phe Asp Glu Asp Gly Lys Leu
            420                 425                 430

Tyr Val Val Asp Arg Ile Lys Glu Leu Ile Lys Tyr Lys Gly Phe Gln
        435                 440                 445

Val Ala Pro Ala Glu Leu Glu Gly Leu Leu Val Ser His Pro Glu Leu
    450                 455                 460

Leu Asp Ala Val Val Ile Pro Phe Pro Asp Ala Glu Ala Gly Glu Val
465                 470                 475                 480

Pro Val Ala Tyr Val Val Arg Ser Pro Asn Ser Ser Leu Thr Glu Glu
                485                 490                 495

Glu Val Gln Lys Tyr Ile Ala Asp Gln Val Ala Pro Phe Lys Arg Leu
            500                 505                 510

Arg Arg Val Thr Phe Ile Asn Thr Val Pro Lys Ser Ala Ser Gly Lys
        515                 520                 525

Ile Leu Arg Arg Glu Leu Ile Glu Lys Val Lys Ser Lys Leu
    530                 535                 540

<210> SEQ ID NO 75
<211> LENGTH: 544
<212> TYPE: PRT
<213> ORGANISM: Populus trichocarpa

<400> SEQUENCE: 75

Met Glu Lys Leu Thr Ala Thr Ala Ser Lys Thr Thr Leu Pro Glu Trp
1               5                   10                  15

```
Tyr Ser Pro Glu Thr Gly Ile Tyr Ser Ser Lys His Pro Ile Pro
            20                  25                  30

Leu Pro Ala Asp Pro Phe Leu Asp Val Val Ser Phe Ile Phe Ser His
        35                  40                  45

His Asn His Asn Gly Leu Thr Ala Leu Ile Asp Ser Ser Ser Gly Phe
 50                  55                  60

Ser Ile Ser Tyr Ser Lys Ile Leu Pro Leu Val Lys Ser Val Ala Ser
 65                  70                  75                  80

Gly Leu Ser Asn Met Gly Ile Lys Gln Gly Asp Val Val Leu Leu Leu
            85                  90                  95

Leu Pro Asn Ser Ile His Phe Pro Ile Val Phe Leu Gly Val Leu Tyr
        100                 105                 110

Leu Gly Gly Ile Val Ser Thr Met Asn Pro Leu Ser Ser Glu Leu Glu
        115                 120                 125

Val Lys Gln Arg Ile Val Asp Cys Asn Ala Cys Ile Ala Phe Val Glu
130                 135                 140

Leu Glu Lys Val Cys Lys Phe Gln Pro Leu Gly Ile Pro Val Ile Gly
145                 150                 155                 160

Val Pro Glu Asn Val Asn Phe Asp Glu Lys Ile Tyr Ser Lys Gly Asp
            165                 170                 175

Val Gly Val Lys Pro Val Ile Arg Gln Gln Asp Thr Ala Ala Ile Met
        180                 185                 190

Tyr Ser Ser Gly Thr Thr Ala Ala Ser Lys Gly Val Val Leu Thr His
        195                 200                 205

Arg Asn Phe Ile Ser Met Val Glu Leu Phe Val Lys Phe Glu Ala Ser
210                 215                 220

Gln Tyr Glu Tyr Ser Ser Thr Asp Asn Val Tyr Leu Ala Val Leu Pro
225                 230                 235                 240

Met Phe His Ile Tyr Gly Leu Ser Leu Phe Val Val Gly Leu Leu Ser
            245                 250                 255

Leu Gly Ser Ser Ile Val Val Met Arg Lys Phe Asp Val Ser Glu Met
        260                 265                 270

Val Lys Val Ile Asp Arg Tyr Gly Val Thr His Phe Pro Val Val Pro
        275                 280                 285

Pro Ile Leu Thr Ala Leu Thr Arg Thr Ala Lys Gly Val Cys Gly Asn
290                 295                 300

Ser Leu Lys Cys Leu Lys Leu Val Ser Cys Gly Ala Ala Pro Leu Phe
305                 310                 315                 320

Gly Lys Thr Ile Gln Asp Phe Val Glu Val Leu Pro His Val Asp Phe
            325                 330                 335

Ile Gln Gly Tyr Gly Leu Thr Glu Ser Thr Ala Val Gly Thr Arg Gly
        340                 345                 350

Leu Asn Thr Glu Lys Phe Gln Lys Tyr Ser Ser Ile Gly Leu Leu Ala
        355                 360                 365

Pro Asn Ile Glu Ala Lys Val Val Asp Trp Ile Thr Gly Ala Leu Leu
370                 375                 380

Pro Pro Gly Gly Ser Gly Glu Leu Trp Ile Arg Gly Pro Gly Val Met
385                 390                 395                 400

Lys Glu Tyr Leu Asn Gly Gly Glu Ala Thr Ala Leu Thr Ile Asp Lys
            405                 410                 415

Asp Gly Trp Leu His Thr Gly Asp Val Val Tyr Ala Asp His Asp Gly
        420                 425                 430
```

```
Tyr Leu Tyr Val Val Asp Arg Leu Lys Glu Ile Ile Lys Tyr Lys Gly
            435                 440                 445

Phe Gln Ile Ala Pro Ala Asp Leu Glu Ala Val Leu Ile Ser His Cys
    450                 455                 460

Glu Ile Leu Asp Ala Ala Val Ile Pro Val Val Asp Lys Glu Cys Gly
465                 470                 475                 480

Glu Ile Pro Val Ala Phe Val Val Lys Arg Gln Gly Ser Met Leu Thr
            485                 490                 495

Gln Glu Ala Ile Ile Asn Tyr Val Glu Gln Val Ala Pro Tyr Lys
                500                 505                 510

Lys Val Arg Lys Val Ile Phe Thr Gln Ser Ile Pro Lys Ser Ala Ala
    515                 520                 525

Gly Lys Ile Leu Arg Arg Glu Leu Lys Cys Ser Leu Thr Ser Lys Leu
    530                 535                 540

<210> SEQ ID NO 76
<211> LENGTH: 433
<212> TYPE: PRT
<213> ORGANISM: Populus trichocarpa

<400> SEQUENCE: 76

Met Ile Ile Asn Val Lys Glu Ser Thr Met Val Gln Pro Ala Glu Glu
1               5                   10                  15

Thr Pro Arg Arg Gly Leu Trp Asn Ser Asn Val Asp Leu Val Val Pro
            20                  25                  30

Arg Phe His Thr Pro Ser Val Tyr Phe Tyr Arg Pro Thr Gly Ala Ser
        35                  40                  45

Asn Phe Phe Asp Ala Lys Val Leu Lys Glu Ala Leu Ser Lys Ala Leu
    50                  55                  60

Val Pro Phe Tyr Pro Met Ala Gly Arg Leu Arg Arg Asp Asp Asp Gly
65                  70                  75                  80

Arg Ile Glu Ile Asp Cys Asn Ala Glu Gly Val Leu Phe Val Glu Ala
                85                  90                  95

Gly Thr Ala Ser Val Val Ala Asp Phe Gly Asp Phe Ala Pro Thr Leu
            100                 105                 110

Glu Leu Lys Gln Leu Ile Pro Thr Val Asp Tyr Ser Gly Gly Ile Ser
        115                 120                 125

Thr Tyr Pro Leu Leu Val Leu Gln Val Thr Tyr Phe Lys Cys Gly Gly
    130                 135                 140

Val Ser Leu Gly Val Gly Met Gln His His Ala Ala Asp Gly Phe Ser
145                 150                 155                 160

Gly Leu His Phe Val Asn Thr Trp Ser Asp Met Ala Arg Gly Leu Asp
                165                 170                 175

Leu Thr Ile Pro Pro Phe Ile Asp Arg Thr Leu Leu Arg Ala Arg Asp
            180                 185                 190

Pro Pro Gln Pro Ala Phe His His Val Glu Tyr Gln Pro Pro Pro Ala
        195                 200                 205

Met Lys Thr Val Leu Glu Thr Ser Lys Pro Glu Ser Thr Ala Val Ser
    210                 215                 220

Ile Phe Lys Leu Thr Arg Asp Gln Leu Asn Thr Leu Lys Ala Lys Ala
225                 230                 235                 240

Lys Glu Gly Gly Asn Asn Ile Gly Tyr Ser Ser Tyr Glu Met Leu Ala
                245                 250                 255

Gly His Val Trp Arg Ser Ala Cys Lys Ala Arg Gly Leu Pro Asp Asp
            260                 265                 270
```

```
Gln Glu Thr Lys Leu Tyr Ile Ala Thr Asp Gly Arg Ser Arg Leu Arg
            275                 280                 285

Pro Thr Leu Pro Pro Gly Tyr Phe Gly Asn Val Ile Phe Thr Ala Thr
290                 295                 300

Pro Ile Ala Val Ala Gly Glu Ile Gln Ser Lys Pro Thr Trp Tyr Ala
305                 310                 315                 320

Ala Gly Lys Ile His Asp Ser Leu Val Arg Met Asp Asn Asp Tyr Leu
            325                 330                 335

Arg Ser Ala Leu Asp Phe Leu Glu Leu Gln Pro Asp Leu Ser Ala Leu
            340                 345                 350

Val Arg Gly Ala His Thr Phe Arg Cys Pro Asn Leu Gly Ile Thr Ser
            355                 360                 365

Trp Val Arg Leu Pro Ile His Asp Ala Asp Phe Gly Trp Gly Arg Pro
370                 375                 380

Ile Phe Met Gly Pro Gly Gly Ile Ala Tyr Glu Gly Leu Ser Phe Ile
385                 390                 395                 400

Ile Pro Ser Ser Thr Asn Asp Gly Ser Leu Ser Val Ala Ile Ser Leu
                405                 410                 415

Gln Ala Glu His Met Lys Leu Phe Glu Lys Phe Ile Tyr Asp Ile Lys
            420                 425                 430

Glu

<210> SEQ ID NO 77
<211> LENGTH: 436
<212> TYPE: PRT
<213> ORGANISM: Cynara cardunculus

<400> SEQUENCE: 77

Met Lys Ile Glu Val Arg Glu Ser Thr Met Val Arg Pro Ala Glu Glu
1               5                   10                  15

Thr Pro Arg Ile Asn Leu Trp Asn Ser Asn Val Asp Leu Val Val Pro
            20                  25                  30

Asn Phe His Thr Pro Ser Val Tyr Phe Tyr Arg Pro Asn Gly Ala Ala
            35                  40                  45

Asn Phe Phe Asp Pro Lys Val Met Lys Asp Ala Leu Ser Arg Ala Leu
        50                  55                  60

Val Pro Phe Tyr Pro Met Gly Gly Arg Leu Lys Arg Asp Glu Asp Gly
65                  70                  75                  80

Arg Ile Glu Ile Asp Cys Gln Gly Gln Gly Val Leu Phe Val Glu Ala
                85                  90                  95

Glu Ser Asp Gly Val Ile Asp Asp Phe Gly Asp Phe Ala Pro Thr Leu
            100                 105                 110

Glu Leu Arg Lys Leu Ile Pro Ala Val Asp Tyr Thr Leu Gly Ile Glu
            115                 120                 125

Ser Tyr Ser Leu Leu Val Leu Gln Val Thr Tyr Phe Lys Cys Gly Gly
        130                 135                 140

Val Ser Leu Gly Val Gly Met Gln His His Ala Ala Asp Gly Ala Ser
145                 150                 155                 160

Gly Leu His Phe Ile Asn Thr Trp Ser Asp Leu Ala Arg Gly Leu Asp
                165                 170                 175

Leu Ala Val Pro Pro Phe Ile Asp Arg Thr Leu Leu Arg Ser Arg Asp
            180                 185                 190

Pro Pro Gln Pro Ala Phe Asp His Ile Glu Tyr Gln Pro Ala Pro Pro
        195                 200                 205
```

```
Met Lys Thr Ala Pro Thr Pro Thr Pro Thr Asp Asp Glu Ser Val Pro
        210                 215                 220

Glu Thr Thr Val Ser Ile Phe Lys Leu Thr Arg Asp Gln Val Asn Ala
225                 230                 235                 240

Leu Lys Gly Lys Ser Lys Glu Asp Gly Asn Thr Val Asn Tyr Ser Ser
                245                 250                 255

Tyr Glu Met Leu Ser Gly His Val Trp Arg Cys Val Cys Lys Ala Arg
            260                 265                 270

Gly Leu Pro Asp Asp Gln Asp Thr Lys Leu Tyr Ile Ala Thr Asp Gly
        275                 280                 285

Arg Ala Arg Leu Arg Pro Ser Leu Pro Arg Gly Tyr Phe Gly Asn Val
290                 295                 300

Ile Phe Thr Thr Thr Pro Ile Ala Val Ala Gly Asp Leu Gln Ser Lys
305                 310                 315                 320

Pro Thr Trp Tyr Ala Ala Ser Lys Ile His Asp Ala Leu Ala Arg Met
                325                 330                 335

Asp Asp Asp Tyr Leu Lys Ser Ala Leu Asp Tyr Leu Glu Leu Gln Pro
            340                 345                 350

Asp Leu Lys Ala Leu Val Arg Gly Ala His Thr Phe Lys Cys Pro Asn
        355                 360                 365

Leu Gly Ile Thr Ser Trp Ala Arg Leu Pro Ile His Asp Ala Asp Phe
370                 375                 380

Gly Trp Gly Arg Pro Ile Phe Met Gly Pro Gly Ile Ala Tyr Glu
385                 390                 395                 400

Gly Leu Ser Phe Val Leu Pro Ser Pro Ile Asn Asp Gly Ser Leu Ser
                405                 410                 415

Ile Val Ile Ser Leu Gln Ala Glu His Met Lys Leu Phe Ser Lys Phe
            420                 425                 430

Leu Tyr Asp Ile
        435

<210> SEQ ID NO 78
<211> LENGTH: 509
<212> TYPE: PRT
<213> ORGANISM: Eucalyptus globulus

<400> SEQUENCE: 78

Met Ala Leu Pro Leu Ile Leu Ser Ile Pro Leu Leu Phe Leu Leu
1               5                   10                  15

Leu Ala His Gln Leu Tyr Gln Arg Leu Arg Phe Lys Leu Pro Pro Gly
                20                  25                  30

Pro Arg Ala Trp Pro Val Val Gly Asn Leu Tyr Asp Ile Lys Pro Val
            35                  40                  45

Arg Phe Arg Cys Phe Ala Glu Trp Ser Gln Ala Tyr Gly Pro Ile Ile
        50                  55                  60

Ser Val Trp Phe Gly Ser Thr Leu Asn Val Val Ser Ser Ser Glu
65                  70                  75                  80

Leu Ala Lys Glu Val Leu Lys Glu Asn Asp Gln Gln Leu Ala Asp Arg
                85                  90                  95

His Arg Ser Arg Ser Ala Ala Lys Phe Ser Arg Asp Gly Gln Asp Leu
            100                 105                 110

Ile Trp Ala Asp Tyr Gly Pro His Tyr Val Lys Val Arg Lys Val Cys
        115                 120                 125

Thr Leu Glu Leu Phe Thr Pro Lys Arg Leu Glu Ala Leu Arg Pro Ile
```

```
                130                 135                 140
Arg Glu Asp Glu Val Thr Ala Met Val Glu Ser Ile Phe Lys Asp Cys
145                 150                 155                 160

Thr Asn Pro Asp Asn Ser Gly Lys Thr Leu Leu Val Lys Lys Tyr Leu
                165                 170                 175

Gly Ala Val Ala Phe Asn Ile Thr Arg Leu Ala Phe Gly Lys Arg
                180                 185                 190

Phe Met Asn Ala Glu Gly Val Ile Asp Glu Gln Gly Leu Glu Phe Lys
                195                 200                 205

Ala Ile Val Ser Asn Gly Leu Lys Leu Gly Ala Ser Leu Ala Met Ala
                210                 215                 220

Glu His Ile Pro Trp Leu Arg Trp Met Phe Pro Leu Glu Glu Glu Ala
225                 230                 235                 240

Phe Ala Lys His Ser Ala Arg Arg Asp Arg Leu Thr Arg Ala Ile Met
                245                 250                 255

Glu Glu His Thr Val Ala Arg Gln Lys Ser Gly Ala Lys Gln His Phe
                260                 265                 270

Val Asp Ala Leu Leu Thr Leu Lys Asp Lys Tyr Asp Leu Ser Glu Asp
                275                 280                 285

Thr Ile Ile Gly Leu Leu Trp Asp Met Ile Thr Ala Gly Met Asp Thr
                290                 295                 300

Thr Ala Ile Ser Val Glu Trp Ala Met Ala Glu Leu Ile Lys Asn Pro
305                 310                 315                 320

Arg Val Gln Gln Lys Ala Gln Glu Glu Leu Asp Arg Val Val Gly Phe
                325                 330                 335

Glu Arg Val Val Thr Glu Pro Asp Phe Ser Asn Leu Pro Tyr Leu Gln
                340                 345                 350

Cys Ile Ala Lys Glu Ala Leu Arg Leu His Pro Pro Thr Pro Leu Met
                355                 360                 365

Leu Pro His Arg Ser Asn Ser His Val Lys Ile Gly Gly Tyr Asp Ile
                370                 375                 380

Pro Lys Gly Ser Asn Val His Val Asn Val Trp Ala Ile Ala Arg Asp
385                 390                 395                 400

Pro Ala Val Trp Asn Ser Pro Leu Glu Phe Arg Pro Glu Arg Phe Leu
                405                 410                 415

Glu Glu Asp Val Asp Met Lys Gly His Asp Phe Arg Leu Leu Pro Phe
                420                 425                 430

Gly Ala Gly Arg Arg Val Cys Pro Gly Ala Gln Leu Gly Ile Asn Leu
                435                 440                 445

Val Thr Ser Met Leu Gly His Leu Leu His His Phe Val Trp Thr Pro
                450                 455                 460

Pro Gln Gly Thr Lys Pro Glu Glu Ile Asp Met Ser Glu Asn Pro Gly
465                 470                 475                 480

Leu Val Thr Tyr Met Ser Thr Pro Val Gln Ala Val Ala Thr Pro Arg
                485                 490                 495

Leu Pro Ser Glu Leu Tyr Lys Arg Val Pro Tyr Glu Met
                500                 505

<210> SEQ ID NO 79
<211> LENGTH: 508
<212> TYPE: PRT
<213> ORGANISM: Populus alba x Populus grandidentata

<400> SEQUENCE: 79
```

-continued

```
Met Asn Leu Leu Leu Ile Pro Ile Ser Phe Ile Thr Ile Leu Leu Thr
1               5                   10                  15

Tyr Lys Ile Tyr Gln Arg Leu Arg Phe Lys Leu Pro Pro Gly Pro Arg
            20                  25                  30

Pro Trp Pro Ile Val Gly Asn Leu Tyr Asp Val Lys Pro Val Arg Phe
        35                  40                  45

Arg Cys Phe Ala Glu Trp Ala Gln Ala Tyr Gly Pro Ile Ile Ser Val
    50                  55                  60

Trp Phe Gly Ser Thr Leu Asn Val Ile Val Ser Asn Thr Glu Leu Ala
65                  70                  75                  80

Lys Glu Val Leu Lys Glu Asn Asp Gln Gln Leu Ala Asp Arg His Arg
                85                  90                  95

Ser Arg Ser Ala Ala Lys Phe Ser Arg Asp Gly Lys Asp Leu Ile Trp
            100                 105                 110

Ala Asp Tyr Gly Pro His Tyr Val Lys Val Arg Lys Val Cys Thr Leu
        115                 120                 125

Glu Leu Phe Ser Pro Lys Arg Leu Glu Ala Leu Arg Pro Ile Arg Glu
    130                 135                 140

Asp Glu Val Thr Ala Met Val Glu Ser Ile Phe Asn Asp Cys Thr Asn
145                 150                 155                 160

Pro Glu Asn Asn Gly Lys Thr Leu Met Val Lys Lys Tyr Leu Gly Ala
                165                 170                 175

Val Ala Phe Asn Asn Ile Thr Arg Leu Ala Phe Gly Lys Arg Phe Glu
            180                 185                 190

Asn Ala Glu Gly Val Met Asp Glu Gln Gly Leu Glu Phe Lys Ala Ile
        195                 200                 205

Val Ser Asn Gly Leu Lys Leu Gly Ala Ser Leu Ala Met Ala Glu His
    210                 215                 220

Ile Pro Trp Leu Arg Trp Met Phe Pro Leu Glu Glu Asp Ala Phe Ala
225                 230                 235                 240

Lys His Gly Ala Arg Arg Asp Arg Leu Thr Arg Ala Ile Met Asp Glu
                245                 250                 255

His Thr Leu Ala Arg Gln Thr Ser Gly Gly Ala Lys Gln His Phe Val
            260                 265                 270

Asp Ala Leu Leu Thr Leu Gln Glu Lys Tyr Asp Leu Ser Glu Asp Thr
        275                 280                 285

Ile Ile Gly Leu Leu Trp Asp Met Ile Thr Ala Gly Met Asp Thr Thr
    290                 295                 300

Ala Ile Ser Val Glu Trp Ala Met Ala Glu Leu Ile Lys Asn Pro Arg
305                 310                 315                 320

Val Gln Gln Lys Ala Gln Glu Glu Leu Asp Ser Val Val Gly Leu Glu
                325                 330                 335

Arg Val Met Thr Glu Ala Asp Phe Ser Gly Leu Pro Tyr Leu Leu Cys
            340                 345                 350

Val Ala Lys Glu Ala Leu Arg Leu His Pro Pro Thr Pro Leu Met Leu
        355                 360                 365

Pro His Arg Ala Asn Ala Asn Val Lys Val Gly Gly Tyr Asp Ile Pro
    370                 375                 380

Lys Gly Ser Asn Val His Val Asn Val Trp Ala Val Ala Arg Asp Pro
385                 390                 395                 400

Ala Ala Trp Lys Asn Pro Leu Glu Phe Arg Pro Glu Arg Phe Leu Glu
                405                 410                 415

Glu Asp Val Asp Met Lys Gly His Asp Phe Arg Leu Leu Pro Phe Gly
```

```
                420             425             430
Ala Gly Arg Arg Val Cys Pro Gly Ala Gln Leu Gly Ile Asn Leu Val
            435             440             445

Thr Ser Met Leu Gly His Leu His His Phe Cys Trp Thr Pro Pro
450             455             460

Glu Gly Val Lys Pro Glu Ile Asp Met Ser Glu Asn Pro Gly Leu
465             470             475             480

Val Thr Tyr Met Arg Thr Pro Leu Gln Ala Val Ala Thr Pro Arg Leu
            485             490             495

Pro Ser His Leu Tyr Lys Arg Val Ala Val Asp Ile
            500             505

<210> SEQ ID NO 80
<211> LENGTH: 509
<212> TYPE: PRT
<213> ORGANISM: Populus trichocarpa

<400> SEQUENCE: 80

Met Ala Leu Pro Leu Val Leu Val Ser Ile Phe Val Leu Leu Leu
1               5               10              15

Ala Tyr Ile Leu Tyr Gln Arg Leu Arg Phe Lys Leu Pro Pro Gly Pro
            20              25              30

Arg Pro Trp Pro Ile Val Gly Asn Leu Tyr Ala Ile Lys Pro Ile Arg
            35              40              45

Phe Arg Cys Phe Ala Glu Trp Ala Gln Ala Tyr Gly Pro Val Val Ser
        50              55              60

Val Trp Phe Gly Ser Thr Leu Asn Val Val Cys Asn Ala Glu Leu
65              70              75              80

Ala Lys Gln Val Leu Lys Glu Asn Asp Gln Gln Leu Ala Asp Arg His
            85              90              95

Arg Ser Arg Leu Ala Ala Arg Phe Ser Arg Asp Gly Lys Asp Leu Ile
        100             105             110

Trp Ala Asp Tyr Gly Pro His Tyr Val Lys Val Arg Arg Val Ser Thr
        115             120             125

Leu Glu Leu Phe Ser Ala Lys Arg Leu Glu Glu Leu Arg Pro Ile Arg
        130             135             140

Glu Asp Glu Val Thr Phe Met Ala Glu Ser Ile Phe Lys Asp Cys Thr
145             150             155             160

Asn Pro Glu Asn His Gly Lys Ser Leu Leu Val Lys Lys Tyr Leu Gly
            165             170             175

Asp Val Ala Phe Asn Asn Ile Thr Arg Leu Ala Phe Gly Lys Arg Phe
        180             185             190

Met Asn Ser Glu Gly Ile Ile Asp Glu Gln Gly Gln Glu Phe Lys Ala
        195             200             205

Ile Val Ser Asn Gly Val Arg Leu Gly Gly Ser Leu Thr Met Ala Glu
        210             215             220

His Ile Pro Trp Leu Gln Trp Met Phe Pro Leu Glu Glu Glu Ala Val
225             230             235             240

Glu Lys His Asn Ala Arg Arg Asp Gly Leu Thr Arg Val Ile Met Glu
            245             250             255

Glu His Thr Asn Ala Arg Lys Lys Ser Gly Gly Ala Lys Lys His Phe
            260             265             270

Val Asp Ala Leu Leu Thr Leu Gln Glu Lys Tyr Asp Leu Ser Glu Val
        275             280             285
```

```
Thr Ile Thr Gly Leu Leu Trp Asp Met Ile Thr Ala Gly Met Asp Thr
    290                 295                 300

Thr Ala Ile Thr Val Glu Trp Ala Met Ala Glu Leu Ile Lys Asn Pro
305                 310                 315                 320

Arg Val Gln Gln Lys Ala Gln Asp Glu Leu Asp Arg Val Val Gly Phe
                325                 330                 335

Glu Arg Val Met Thr Glu Ala Asp Phe Pro Asn Leu Pro Tyr Leu Gln
                340                 345                 350

Ala Val Val Lys Glu Ser Leu Arg Leu His Pro Pro Thr Pro Leu Met
                355                 360                 365

Leu Pro His Arg Ala Asn Thr Thr Val Lys Ile Gly Gly Tyr Asp Ile
370                 375                 380

Pro Lys Gly Ser Val Val His Val Asn Val Trp Ala Val Ala Arg Asp
385                 390                 395                 400

Pro Ala Leu Trp Lys Asn Pro Leu Glu Phe Arg Pro Glu Arg Phe Phe
                405                 410                 415

Glu Glu Asp Val Asp Met Arg Gly His Asp Phe Arg Leu Leu Pro Phe
                420                 425                 430

Gly Ala Gly Arg Arg Val Cys Pro Gly Ala Gln Leu Gly Ile Asn Leu
                435                 440                 445

Val Thr Ser Ile Ile Gly His Leu His His Phe His Trp Thr Thr
450                 455                 460

Pro Asp Gly Val Lys Pro Glu Glu Ile Asp Met Ser Glu Arg Pro Gly
465                 470                 475                 480

Leu Val Thr Tyr Met Met Thr Pro Leu Gln Ala Val Ala Thr Pro Arg
                485                 490                 495

Leu Pro Ser His Leu Tyr Lys Arg Met Ala Ser Asp Met
                500                 505

<210> SEQ ID NO 81
<211> LENGTH: 505
<212> TYPE: PRT
<213> ORGANISM: Gossypium arboreum

<400> SEQUENCE: 81

Met Asp Leu Leu Phe Leu Glu Lys Ala Leu Gly Leu Phe Val Ala
1               5                   10                  15

Val Val Leu Ala Ile Thr Ile Ser Lys Leu Arg Gly Lys Arg Phe Lys
                20                  25                  30

Leu Pro Pro Gly Pro Leu Pro Val Pro Val Phe Gly Asn Trp Leu Gln
                35                  40                  45

Val Gly Asp Asp Leu Asn His Arg Asn Leu Thr Asp Leu Ala Lys Lys
50                  55                  60

Phe Gly Asp Ile Phe Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
                100                 105                 110

Lys Gly Gln Asp Met Val Phe Thr Val Tyr Gly Glu His Trp Arg Lys
                115                 120                 125

Met Arg Arg Ile Met Thr Val Pro Phe Phe Thr Asn Lys Val Val Gln
                130                 135                 140

Gln Tyr Arg Phe Gly Trp Glu Asp Glu Ala Ala Arg Val Val Glu Asp
145                 150                 155                 160
```

```
Val Arg Lys Asn Pro Glu Ala Ala Thr Asn Gly Ile Val Leu Arg Arg
            165                 170                 175

Arg Leu Gln Leu Met Met Tyr Asn Asn Met Tyr Arg Ile Met Phe Asp
        180                 185                 190

Thr Arg Phe Glu Ser Glu Asp Asp Pro Leu Phe Val Arg Leu Lys Ala
    195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Gly Tyr Leu Lys
225                 230                 235                 240

Ile Cys Lys Glu Val Lys Asp Arg Leu Gln Leu Phe Lys Asp His
                245                 250                 255

Phe Val Glu Glu Arg Lys Lys Leu Gly Ser Thr Lys Ser Met Asn Asn
                260                 265                 270

Asp Gly Leu Lys Cys Ala Ile Asp His Ile Leu Asp Ala Gln Gln Lys
                275                 280                 285

Gly Glu Ile Asn Glu Asp Asn Val Leu Tyr Ile Val Glu Asn Ile Asn
        290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Lys Lys Leu Arg His Glu Leu
                325                 330                 335

Asp Thr Val Leu Gly Pro Gly Asn Gln Ile Thr Glu Pro Asp Thr His
            340                 345                 350

Lys Leu Pro Tyr Leu Gln Ala Val Ile Lys Glu Thr Leu Arg Leu Arg
                355                 360                 365

Met Ala Ile Pro Leu Leu Val Pro His Met Asn Leu His Asp Ala Lys
        370                 375                 380

Leu Gly Gly Tyr Asp Ile Pro Ala Glu Ser Lys Ile Leu Val Asn Ala
385                 390                 395                 400

Trp Trp Leu Ala Asn Asn Pro Ala Asn Trp Lys Asn Pro Glu Glu Phe
                405                 410                 415

Arg Pro Glu Arg Phe Phe Glu Glu Ala Lys Val Glu Ala Asn Gly
            420                 425                 430

Asn Asp Phe Arg Tyr Leu Pro Phe Gly Val Gly Arg Arg Ser Cys Pro
                435                 440                 445

Gly Ile Ile Leu Ala Leu Pro Ile Leu Gly Ile Thr Leu Gly Arg Leu
        450                 455                 460

Val Gln Asn Phe Glu Leu Leu Pro Pro Gly Gln Ser Gln Ile Asp
465                 470                 475                 480

Thr Thr Glu Lys Gly Gly Gln Phe Ser Leu His Ile Leu Lys His Ser
                485                 490                 495

Thr Ile Val Ala Lys Pro Arg Gln Phe
            500                 505

<210> SEQ ID NO 82
<211> LENGTH: 505
<212> TYPE: PRT
<213> ORGANISM: Gossypium hirsutum

<400> SEQUENCE: 82

Met Asp Leu Leu Phe Leu Glu Lys Ala Leu Leu Gly Leu Phe Val Ala
1               5                   10                  15

Val Val Leu Ala Ile Thr Ile Ser Lys Leu Arg Gly Lys Arg Phe Lys
```

-continued

```
                20                  25                  30
Leu Pro Pro Gly Pro Leu Pro Val Pro Val Phe Gly Asn Trp Leu Gln
            35                  40                  45
Val Gly Asp Asp Leu Asn His Arg Asn Leu Thr Asp Leu Ala Lys Lys
 50                  55                  60
Phe Gly Asp Ile Phe Leu Arg Met Gly Gln Arg Asn Leu Val Val
 65                  70                  75                  80
Val Ser Ser Pro Glu Leu Ala Lys Glu Val Leu His Thr Gln Gly Val
                85                  90                  95
Glu Phe Gly Ser Arg Thr Arg Asn Val Val Phe Gly Ile Phe Thr Gly
               100                 105                 110
Lys Gly Gln Asp Met Val Phe Thr Val Tyr Gly Glu His Trp Arg Lys
               115                 120                 125
Met Arg Arg Ile Met Thr Val Pro Phe Phe Thr Asn Lys Val Val Gln
               130                 135                 140
Gln Tyr Arg Phe Gly Trp Glu Asp Glu Ala Ala Arg Val Val Glu Asp
145                 150                 155                 160
Val Arg Lys Asn Pro Glu Ala Ala Thr Asn Gly Ile Val Leu Arg Arg
               165                 170                 175
Arg Leu Gln Leu Met Met Tyr Asn Asn Met Tyr Arg Ile Met Phe Asp
               180                 185                 190
Thr Arg Phe Glu Ser Glu Asp Asp Pro Leu Phe Val Arg Leu Lys Ala
               195                 200                 205
Leu Asn Gly Glu Arg Ser Arg Leu Ala Gln Ser Phe Glu Tyr Asn Tyr
               210                 215                 220
Gly Asp Phe Ile Pro Ile Leu Arg Pro Phe Leu Arg Gly Tyr Leu Lys
225                 230                 235                 240
Ile Cys Lys Glu Val Lys Asp Arg Arg Leu Gln Leu Phe Lys Asp His
               245                 250                 255
Phe Val Glu Glu Arg Lys Lys Leu Gly Ser Thr Lys Ser Met Asn Asn
               260                 265                 270
Asp Gly Leu Lys Cys Ala Ile Asp His Ile Leu Asp Ala Gln Gln Lys
               275                 280                 285
Gly Glu Ile Asn Glu Asp Asn Val Leu Tyr Ile Val Glu Asn Ile Asn
               290                 295                 300
Val Ala Ala Ile Glu Thr Thr Leu Trp Ser Ile Glu Trp Gly Ile Ala
305                 310                 315                 320
Glu Leu Val Asn His Pro Glu Thr Gln Lys Lys Leu Arg His Glu Leu
               325                 330                 335
Asp Thr Val Leu Gly Pro Gly Asn Gln Ile Thr Glu Pro Asp Thr His
               340                 345                 350
Lys Leu Pro Tyr Leu Gln Ala Val Ile Lys Glu Thr Leu Arg Leu Arg
               355                 360                 365
Met Ala Ile Pro Leu Leu Val Pro His Met Asn Leu His Asp Ala Lys
               370                 375                 380
Leu Gly Gly Tyr Asp Ile Pro Ala Glu Ser Lys Ile Leu Val Asn Ala
385                 390                 395                 400
Trp Trp Leu Ala Asn Asn Pro Ala Asn Trp Lys Asn Pro Glu Glu Phe
               405                 410                 415
Arg Pro Glu Arg Phe Phe Glu Glu Ala Lys Val Glu Ala Asn Gly
               420                 425                 430
Asn Asp Phe Arg Tyr Leu Pro Phe Gly Val Gly Arg Arg Ser Cys Pro
               435                 440                 445
```

```
Gly Ile Ile Leu Ala Leu Pro Ile Leu Gly Ile Thr Leu Gly Arg Leu
    450                 455                 460

Val Gln Asn Phe Glu Leu Leu Pro Pro Gly Gln Ser Gln Ile Asp
465                 470                 475                 480

Thr Thr Glu Lys Gly Gly Gln Phe Ser Leu His Ile Leu Lys His Ser
                485                 490                 495

Thr Ile Val Ala Lys Pro Arg Gln Phe
            500                 505
```

<210> SEQ ID NO 83
<211> LENGTH: 711
<212> TYPE: PRT
<213> ORGANISM: Populus trichocarpa

<400> SEQUENCE: 83

```
Met Glu Phe Cys Gln Asp Ser Arg Asn Gly Asn Gly Ser Leu Gly Phe
1               5                   10                  15

Asn Thr Asn Asp Pro Leu Asn Trp Gly Met Ala Ala Glu Ser Leu Lys
            20                  25                  30

Gly Ser His Leu Asp Glu Val Lys Arg Met Ile Glu Glu Tyr Arg Lys
        35                  40                  45

Pro Val Val Lys Leu Gly Gly Glu Thr Leu Thr Ile Gly Gln Val Thr
    50                  55                  60

Ala Ile Ala Ser Arg Asp Val Gly Val Met Val Glu Leu Ser Glu Glu
65                  70                  75                  80

Ala Arg Ala Gly Val Lys Ala Ser Ser Asp Trp Val Met Asp Ser Met
                85                  90                  95

Ser Lys Gly Thr Asp Ser Tyr Gly Val Thr Thr Gly Phe Gly Ala Thr
            100                 105                 110

Ser His Arg Arg Thr Lys Gln Gly Gly Glu Leu Gln Lys Glu Leu Ile
        115                 120                 125

Arg Phe Leu Asn Ala Gly Ile Phe Gly Asn Gly Thr Glu Ser Ser His
    130                 135                 140

Thr Leu Pro Arg Ser Ala Thr Arg Ala Ala Met Leu Val Arg Ile Asn
145                 150                 155                 160

Thr Leu Leu Gln Gly Tyr Ser Gly Ile Arg Phe Glu Met Leu Glu Ala
                165                 170                 175

Ile Thr Lys Leu Leu Asn His Asn Ile Thr Pro Cys Leu Pro Leu Arg
            180                 185                 190

Gly Thr Ile Thr Ala Ser Gly Asp Leu Val Pro Leu Ser Tyr Ile Ala
        195                 200                 205

Gly Leu Leu Thr Gly Arg Pro Asn Ser Lys Ala Val Gly Pro Asn Gly
    210                 215                 220

Glu Pro Leu Ser Pro Ala Glu Ala Phe Thr Gln Ala Gly Ile Asp Gly
225                 230                 235                 240

Gly Phe Phe Glu Leu Gln Pro Lys Glu Gly Leu Ala Leu Val Asn Gly
                245                 250                 255

Thr Ala Val Gly Ser Gly Leu Ala Ser Met Val Leu Phe Glu Thr Asn
            260                 265                 270

Val Leu Ala Ile Leu Ser Glu Val Leu Ser Ala Ile Phe Ala Glu Val
        275                 280                 285

Met Gln Gly Lys Pro Glu Phe Thr Asp His Leu Thr His Lys Leu Lys
    290                 295                 300

His His Pro Gly Gln Ile Glu Ala Ala Ala Ile Met Glu His Ile Leu
```

```
305                 310                 315                 320
Asp Gly Ser Ser Tyr Val Lys Glu Ala Gln Lys Leu His Glu Ile Asp
                    325                 330                 335

Pro Leu Gln Lys Pro Lys Gln Asp Arg Tyr Ala Leu Arg Thr Ser Pro
                340                 345                 350

Gln Trp Leu Gly Pro Leu Ile Glu Val Ile Arg Thr Thr Lys Met
                355                 360                 365

Ile Glu Arg Glu Ile Asn Ser Val Asn Asp Asn Pro Leu Ile Asp Val
370                 375                 380

Ser Arg Asn Lys Ala Leu His Gly Gly Asn Phe Gln Gly Thr Pro Ile
385                 390                 395                 400

Gly Val Ser Met Asp Asn Thr Arg Leu Ala Ile Ala Ser Ile Gly Lys
                    405                 410                 415

Leu Met Phe Ala Gln Phe Ser Glu Leu Val Asn Asp Phe Tyr Asn Asn
                420                 425                 430

Gly Leu Pro Ser Asn Leu Thr Gly Gly Arg Asn Pro Ser Leu Asp Tyr
                435                 440                 445

Gly Phe Lys Gly Ala Glu Ile Ala Met Ala Ser Tyr Cys Ser Glu Leu
                450                 455                 460

Gln Phe Leu Ala Asn Pro Val Thr Asn His Val Gln Ser Ala Glu Gln
465                 470                 475                 480

His Asn Gln Asp Val Asn Ser Leu Gly Leu Ile Ser Ser Arg Lys Thr
                    485                 490                 495

Ala Glu Ala Val Asp Ile Leu Lys Leu Met Ser Thr Thr Phe Leu Val
                500                 505                 510

Gly Leu Cys Gln Ala Val Asp Leu Arg His Ile Glu Glu Asn Leu Lys
                515                 520                 525

Ser Thr Val Lys Asn Thr Val Ser Gln Val Ala Lys Arg Val Leu Thr
                    530                 535                 540

Met Gly Phe Asn Gly Glu Leu His Pro Ser Arg Phe Cys Glu Lys Asp
545                 550                 555                 560

Leu Leu Lys Val Val Asp Arg Glu His Val Phe Ser Tyr Ile Asp Asp
                    565                 570                 575

Pro Cys Ser Ala Thr Tyr Pro Leu Met Gln Lys Leu Arg Gln Val Leu
                580                 585                 590

Val Glu His Ala Leu Val Asn Gly Glu Arg Glu Arg Asn Ser Thr Thr
                    595                 600                 605

Ser Ile Phe Gln Lys Ile Gly Ser Phe Glu Glu Leu Lys Thr Leu
                    610                 615                 620

Leu Pro Lys Glu Val Glu Ser Ala Arg Leu Glu Val Glu Asn Gly Asn
625                 630                 635                 640

Pro Ala Ile Pro Asn Arg Ile Lys Glu Cys Arg Ser Tyr Pro Leu Tyr
                    645                 650                 655

Lys Phe Val Arg Glu Glu Leu Gly Thr Ser Leu Leu Thr Gly Glu Lys
                    660                 665                 670

Val Lys Ser Pro Gly Glu Glu Phe Asp Lys Val Phe Thr Ala Ile Cys
                675                 680                 685

Ala Gly Lys Leu Ile Asp Pro Leu Leu Glu Cys Leu Lys Glu Trp Asp
                690                 695                 700

Gly Ala Pro Leu Pro Ile Cys
705                 710
```

<210> SEQ ID NO 84

```
<211> LENGTH: 713
<212> TYPE: PRT
<213> ORGANISM: Jatropha curcas

<400> SEQUENCE: 84
```

| | | | | | | | | | | | | | | |
|---|---|---|---|---|---|---|---|---|---|---|---|---|---|---|
| Met | Ala | Thr | Ile | Ile | Gly | Asn | Gly | His | Gln | Asn | Gly | Ser | Leu | Glu | Gly |
| 1 | | | | 5 | | | | | 10 | | | | | 15 | |
| Leu | Cys | Ile | Thr | Arg | Asp | Pro | Leu | Ser | Trp | Gly | Val | Ala | Ala | Glu | Ser |
| | | | 20 | | | | | 25 | | | | | 30 | | |
| Met | Lys | Gly | Ser | His | Leu | Asp | Glu | Val | Lys | Lys | Met | Val | Ser | Glu | Tyr |
| | | 35 | | | | | 40 | | | | | 45 | | | |
| Arg | Lys | Pro | Leu | Val | Lys | Leu | Gly | Gly | Glu | Thr | Leu | Thr | Val | Ala | Gln |
| | 50 | | | | | 55 | | | | | 60 | | | | |
| Val | Ala | Ala | Ile | Ala | Ser | His | Asp | Ala | Gly | Val | Lys | Val | Glu | Leu | Ala |
| 65 | | | | | 70 | | | | | 75 | | | | | 80 |
| Glu | Ser | Ala | Arg | Ala | Gly | Val | Lys | Ala | Ser | Ser | Asp | Trp | Val | Met | Asp |
| | | | | 85 | | | | | 90 | | | | | 95 | |
| Ser | Met | Asn | Lys | Gly | Thr | Asp | Ser | Tyr | Gly | Val | Thr | Thr | Gly | Phe | Gly |
| | | | 100 | | | | | 105 | | | | | 110 | | |
| Ala | Thr | Ser | His | Arg | Arg | Thr | Lys | Gln | Gly | Ala | Ala | Leu | Gln | Arg | Glu |
| | | 115 | | | | | 120 | | | | | 125 | | | |
| Leu | Ile | Arg | Phe | Leu | Asn | Ala | Gly | Ile | Phe | Gly | Asn | Gly | Thr | Glu | Thr |
| | 130 | | | | | 135 | | | | | 140 | | | | |
| Cys | His | Thr | Leu | Pro | His | Ser | Ala | Thr | Arg | Ala | Ala | Met | Leu | Val | Arg |
| 145 | | | | | 150 | | | | | 155 | | | | | 160 |
| Ile | Asn | Thr | Leu | Leu | Gln | Gly | Tyr | Ser | Gly | Ile | Arg | Phe | Glu | Ile | Leu |
| | | | | 165 | | | | | 170 | | | | | 175 | |
| Glu | Ala | Ile | Thr | Lys | Leu | Leu | Asn | His | Asn | Ile | Thr | Pro | Cys | Leu | Pro |
| | | | 180 | | | | | 185 | | | | | 190 | | |
| Leu | Arg | Gly | Thr | Ile | Thr | Ala | Ser | Gly | Asp | Leu | Val | Pro | Leu | Ser | Tyr |
| | | 195 | | | | | 200 | | | | | 205 | | | |
| Ile | Ala | Gly | Leu | Leu | Thr | Gly | Arg | Pro | Asn | Ser | Lys | Ala | Ile | Gly | Pro |
| | 210 | | | | | 215 | | | | | 220 | | | | |
| Ser | Gly | Glu | Ser | Leu | Asp | Ala | Val | Glu | Ala | Phe | Arg | Leu | Ala | Asp | Ile |
| 225 | | | | | 230 | | | | | 235 | | | | | 240 |
| Asp | Ser | Gly | Phe | Phe | Glu | Leu | Gln | Pro | Lys | Glu | Gly | Leu | Ala | Leu | Val |
| | | | | 245 | | | | | 250 | | | | | 255 | |
| Asn | Gly | Thr | Ala | Val | Gly | Ser | Gly | Leu | Ala | Ser | Met | Val | Leu | Phe | Glu |
| | | | 260 | | | | | 265 | | | | | 270 | | |
| Ala | Asn | Val | Leu | Ala | Val | Leu | Ser | Glu | Ile | Leu | Ser | Ala | Ile | Phe | Ala |
| | | 275 | | | | | 280 | | | | | 285 | | | |
| Glu | Val | Met | Asn | Gly | Lys | Pro | Glu | Phe | Thr | Asp | His | Leu | Thr | His | Lys |
| | 290 | | | | | 295 | | | | | 300 | | | | |
| Leu | Lys | His | His | Pro | Gly | Gln | Ile | Glu | Ala | Ala | Ile | Met | Glu | His | |
| 305 | | | | | 310 | | | | | 315 | | | | | 320 |
| Ile | Leu | Asp | Gly | Ser | Ser | Tyr | Ile | Lys | Ala | Ala | Lys | Gln | Leu | His | Glu |
| | | | | 325 | | | | | 330 | | | | | 335 | |
| Ile | Asp | Pro | Leu | Gln | Lys | Pro | Lys | Gln | Asp | Arg | Tyr | Ala | Leu | Arg | Thr |
| | | | 340 | | | | | 345 | | | | | 350 | | |
| Ser | Pro | Gln | Trp | Leu | Gly | Pro | Gln | Ile | Glu | Val | Ile | Arg | Phe | Ser | Thr |
| | | 355 | | | | | 360 | | | | | 365 | | | |
| Lys | Ser | Ile | Glu | Arg | Glu | Ile | Asn | Ser | Val | Asn | Asp | Asn | Pro | Leu | Ile |
| | 370 | | | | | 375 | | | | | 380 | | | | |
| Asp | Val | Ser | Arg | Asn | Lys | Ala | Leu | His | Gly | Gly | Asn | Phe | Gln | Gly | Thr |

```
            385                 390                 395                 400
    Pro Ile Gly Val Ser Met Asp Asn Ala Arg Leu Ala Ile Ala Ser Ile
                    405                 410                 415

Gly Lys Leu Met Phe Ala Gln Phe Ser Glu Leu Val Asn Asp Phe Tyr
                420                 425                 430

Asn Asn Gly Leu Pro Ser Asn Leu Ser Gly Gly Arg Asn Pro Ser Leu
            435                 440                 445

Asp Tyr Gly Phe Lys Gly Ala Glu Ile Ala Met Ala Ser Tyr Cys Ser
        450                 455                 460

Glu Leu Gln Phe Leu Ala Asn Pro Val Thr Ser His Val Gln Ser Ala
    465                 470                 475                 480

Glu Gln His Asn Gln Asp Val Asn Ser Leu Gly Leu Ile Ser Ser Arg
                    485                 490                 495

Lys Thr Gln Glu Ala Ile Asp Ile Leu Lys Leu Met Ser Thr Phe
                500                 505                 510

Leu Val Ala Leu Cys Gln Ala Ile Asp Leu Arg His Leu Glu Glu Asn
            515                 520                 525

Leu Lys His Ala Val Lys Asn Thr Val Thr Gln Val Ala Lys Arg Val
        530                 535                 540

Leu Thr Thr Gly Ala Asn Gly Glu Leu His Pro Ser Arg Phe Cys Gly
    545                 550                 555                 560

Lys Asp Leu Leu Lys Val Val Asp Arg Glu Gln Val Phe Ala Tyr Ile
                    565                 570                 575

Asp Asp Pro Cys Ser Ala Thr Tyr Pro Leu Met Gln Lys Leu Arg Gln
                580                 585                 590

Val Leu Val Glu His Ala Leu Ala Asn Gly Glu Asn Glu Lys Asn Ala
            595                 600                 605

Ser Thr Ser Val Phe Gln Lys Ile Gly Ala Phe Glu Glu Leu Lys
        610                 615                 620

Thr Leu Leu Pro Lys Glu Val Glu Ser Ala Arg Glu Ala Tyr Glu Ser
    625                 630                 635                 640

Gly Ser Ala Ala Ile Gly Asn Lys Ile Lys Glu Cys Arg Ser Tyr Pro
                    645                 650                 655

Leu Tyr Lys Phe Val Arg Glu Glu Leu Gly Ser Gly Leu Leu Thr Gly
                660                 665                 670

Glu Lys Val Arg Ser Pro Gly Glu Glu Phe Asp Lys Val Phe Thr Ala
            675                 680                 685

Met Cys Glu Gly Lys Ile Ile Asp Pro Met Met Glu Cys Leu Lys Glu
        690                 695                 700

Trp Asn Gly Ala Pro Leu Pro Ile Cys
    705                 710

<210> SEQ ID NO 85
<211> LENGTH: 324
<212> TYPE: PRT
<213> ORGANISM: Arabidopsis thaliana

<400> SEQUENCE: 85

Met Leu Thr Asp Glu Arg Glu Val Val Cys Val Thr Gly Ala Ser Gly
    1               5                   10                  15

Cys Ile Gly Ser Trp Leu Val His Gln Leu Leu Arg Gly Tyr Ser
                20                  25                  30

Val His Ala Thr Val Lys Asn Leu Gln Asp Glu Lys Glu Thr Lys His
            35                  40                  45
```

Leu Glu Gly Leu Glu Gly Ala Ala Thr Arg Leu His Leu Phe Glu Met
 50                  55                  60

Asp Leu Leu Gln Tyr Asp Thr Val Ser Ala Ala Ile Asn Gly Cys Ser
 65                  70                  75                  80

Gly Val Phe His Leu Ala Ser Pro Cys Ile Val Asp Glu Val Gln Asp
                 85                  90                  95

Pro Gln Lys Gln Leu Leu Asp Pro Ala Val Lys Gly Thr Ile Asn Val
            100                 105                 110

Leu Thr Ala Ala Lys Glu Ala Ser Val Lys Arg Val Val Thr Ser
            115                 120                 125

Ser Ile Ser Ala Ile Thr Pro Ser Pro Asn Trp Pro Ala Asp Lys Ile
130                 135                 140

Lys Asn Glu Glu Cys Trp Ala Ala Glu Asp Tyr Cys Arg Gln Asn Gly
145                 150                 155                 160

Leu Trp Tyr Pro Leu Ser Lys Thr Leu Ala Glu Lys Ala Ala Trp Glu
                165                 170                 175

Phe Ala Glu Glu Lys Gly Leu Asp Val Val Val Asn Pro Gly Thr
            180                 185                 190

Val Met Gly Pro Val Ile Pro Pro Ser Leu Asn Ala Ser Met His Met
            195                 200                 205

Leu Leu Arg Leu Leu Gln Gly Cys Thr Glu Thr Tyr Glu Asn Phe Phe
210                 215                 220

Met Gly Ser Val His Phe Lys Asp Val Ala Leu Ala His Ile Leu Val
225                 230                 235                 240

Tyr Glu Asp Pro Tyr Ser Lys Gly Arg His Leu Cys Val Glu Ala Ile
                245                 250                 255

Ser His Tyr Gly Asp Phe Val Ala Lys Val Ala Glu Leu Tyr Pro Asn
            260                 265                 270

Tyr Asn Val Pro Lys Leu Pro Arg Glu Thr Gln Pro Gly Leu Leu Arg
            275                 280                 285

Asp Lys Asn Ala Ser Lys Lys Leu Ile Asp Leu Gly Leu Lys Phe Ile
            290                 295                 300

Ser Met Glu Glu Ile Ile Lys Glu Gly Val Glu Ser Leu Lys Ser Lys
305                 310                 315                 320

Gly Phe Ile Ser

<210> SEQ ID NO 86
<211> LENGTH: 323
<212> TYPE: PRT
<213> ORGANISM: Arabidopsis lyrata

<400> SEQUENCE: 86

Met Ser Thr Glu Arg Glu Val Val Cys Val Thr Gly Ala Ser Gly Cys
 1               5                  10                  15

Ile Gly Ser Trp Leu Val His Leu Leu Leu His Arg Gly Tyr Ser Val
                 20                  25                  30

His Ala Thr Val Lys Asn Leu Gln Asp Glu Lys Glu Thr Lys His Leu
             35                  40                  45

Glu Ala Leu Glu Gly Ala Ala Thr Arg Leu His Leu Phe Glu Met Asp
 50                  55                  60

Leu Leu Gln Tyr Asp Thr Val Ser Ala Ala Val Asn Gly Cys Ser Gly
 65                  70                  75                  80

Val Phe His Leu Ala Ser Pro Cys Ile Val Asp Glu Val Gln Asp Pro
                 85                  90                  95

```
Gln Lys Gln Leu Leu Asp Pro Ala Val Lys Gly Thr Ile Asn Val Leu
            100                 105                 110

Thr Ala Ala Lys Glu Ala Gly Val Lys Arg Val Val Thr Ser Ser
        115                 120                 125

Ile Ser Ala Ile Thr Pro Ser Pro Asn Trp Pro Ala Asp Lys Ile Lys
        130                 135                 140

Asn Glu Glu Cys Trp Ala Asp Gln Asp Tyr Cys Lys Gln Asn Gly Leu
145                 150                 155                 160

Trp Tyr Pro Leu Ser Lys Thr Leu Ala Glu Lys Ala Ala Trp Glu Phe
                    165                 170                 175

Ala Glu Gln Lys Gly Leu Asp Val Val Val Asn Pro Gly Thr Val
        180                 185                 190

Met Gly Pro Val Ile Pro Ser Ile Asn Ala Ser Met Leu Met Leu
        195                 200                 205

Leu Arg Leu Leu Gln Gly Cys Thr Glu Thr Tyr Glu Asn Phe Phe Met
210                 215                 220

Gly Ser Val His Phe Lys Asp Val Ala Leu Ala His Ile Leu Val Tyr
225                 230                 235                 240

Glu Asn Pro Ser Ala Lys Gly Arg His Leu Cys Val Glu Ala Ile Ser
                245                 250                 255

His Tyr Gly Asp Phe Val Ala Lys Val Ala Glu Leu Tyr Pro Asn Tyr
                260                 265                 270

Ser Val Pro Lys Leu Pro Arg Glu Thr Gln Leu Gly Leu Leu Arg Ala
            275                 280                 285

Lys Asn Ala Ala Lys Lys Leu Met Glu Leu Gly Leu Glu Phe Ser Ser
290                 295                 300

Met Glu Asp Ile Ile Lys Glu Gly Val Glu Ser Leu Lys Ser Lys Gly
305                 310                 315                 320

Phe Ile Ser

<210> SEQ ID NO 87
<211> LENGTH: 329
<212> TYPE: PRT
<213> ORGANISM: Camellia oleifera

<400> SEQUENCE: 87

Met Ser Ser Asn Thr Lys Ala Gly Gly Asp Gly Gln Val Val Cys Val
1               5                   10                  15

Thr Gly Gly Ser Gly Phe Ile Gly Ser Trp Leu Val Arg Leu Leu Leu
            20                  25                  30

Asp Arg Gly Tyr Thr Val His Ala Thr Val Lys Asp Leu Lys Asp Glu
        35                  40                  45

Lys Glu Thr Lys His Leu Glu Ala Leu Glu Gly Ala Glu Ser Arg Leu
    50                  55                  60

Arg Leu Phe Gln Ile Asp Leu Leu Asp Tyr Asp Ser Ile Val Ala Ala
65                  70                  75                  80

Val Thr Gly Ser Ser Gly Val Phe His Leu Ala Ser Pro Cys Ile Val
                85                  90                  95

Asp Gln Val Lys Asp Pro Glu Arg Glu Leu Leu Glu Pro Ala Ile Lys
            100                 105                 110

Gly Thr Leu Asn Val Leu Thr Ala Ala Lys Glu Leu Gly Val Arg Arg
        115                 120                 125

Val Val Val Thr Ser Ser Asn Thr Ala Ile Thr Pro Ser Pro Asn Trp
    130                 135                 140
```

```
Pro Ala Asp Lys Val Lys Asn Glu Asp Cys Trp Thr Asp Val Glu Tyr
145                 150                 155                 160

Cys Lys Gln Asn Gly Leu Trp Tyr Pro Leu Ser Lys Thr Leu Ala Glu
            165                 170                 175

Lys Ala Ala Trp Glu Phe Ala Lys Glu Lys Gly Leu Asp Val Val Val
        180                 185                 190

Val Asn Pro Gly Thr Val Met Gly Pro Ile Ile Pro Ala Leu Asn
    195                 200                 205

Ala Ser Met Leu Met Leu Leu Arg Phe Leu Gln Gly Cys Thr Glu Ile
    210                 215                 220

Tyr Glu Asn Phe Phe Met Gly Pro Val His Val Lys Asp Val Ala Leu
225                 230                 235                 240

Ala His Ile Leu Val Tyr Glu Asn Thr Ser Ala Thr Gly Arg His Leu
            245                 250                 255

Cys Val Glu Ala Ile Ser His Tyr Gly Asp Phe Thr Ala Met Val Ala
        260                 265                 270

Glu Leu Tyr Pro Glu Tyr Asn Val Pro Arg Leu Pro Lys Asp Thr Gln
    275                 280                 285

Pro Gly Leu Leu Arg Thr Lys Asp Gly Ser Lys Lys Leu Met Asp Leu
290                 295                 300

Gly Phe Gln Phe Ile Pro Met Glu Gln Ile Ile Lys Glu Thr Val Glu
305                 310                 315                 320

Ser Leu Lys Ser Lys Gly Tyr Ile Ser
            325

<210> SEQ ID NO 88
<211> LENGTH: 334
<212> TYPE: PRT
<213> ORGANISM: Ricinus communis

<400> SEQUENCE: 88

Met Ala Thr Gln Asn Lys Lys Glu Ala Val Cys Val Thr Gly Ala Asn
1               5                   10                  15

Gly Phe Ile Gly Ser Trp Leu Ile Gln Thr Leu Leu Gln His Gly Tyr
            20                  25                  30

Thr Thr Ile His Ala Ser Ile Tyr Pro Ala Ser Asp Pro Ser His Leu
        35                  40                  45

Phe His Leu Ile Ser Ser Ser His Gly Asp Ile Ile Asn Leu Lys
    50                  55                  60

Leu Tyr Glu Ala Asp Leu Leu Asp Tyr Asp Ala Ile Cys Lys Ala Val
65                  70                  75                  80

Glu Gly Cys Gln Gly Val Phe His Val Ala Ser Pro Cys Thr Leu Glu
                85                  90                  95

Glu Pro Lys Asp Pro Glu Lys Glu Leu Val Leu Pro Ala Val Gln Gly
            100                 105                 110

Thr Ile Asn Val Leu Glu Ala Ala Arg Lys Phe Lys Val Arg Arg Val
        115                 120                 125

Val Leu Thr Ser Ser Ile Ser Ala Leu Val Pro Asn Pro Asn Trp Pro
130                 135                 140

Ala Gly Lys Val Phe Asp Glu Ser Ser Trp Thr Asp Leu Asp Tyr Cys
145                 150                 155                 160

Lys Ser Arg Gln Lys Trp Tyr Pro Val Ser Lys Ser Leu Ala Glu Lys
                165                 170                 175

Ala Ala Trp Glu Phe Ala Glu Lys His Gly Met Asp Val Val Ala Ile
            180                 185                 190
```

```
His Pro Ser Thr Cys Ile Gly Pro Leu Leu Gln Pro Ser Leu Asn Ala
        195                 200                 205

Ser Ser Ala Val Leu Gln Gln Leu Leu Glu Gly Ser Lys Asp Thr Gln
210                 215                 220

Glu Tyr His Trp Leu Gly Ala Val His Val Lys Asp Val Ala Lys Ala
225                 230                 235                 240

Gln Val Leu Leu Phe Glu Ala Pro Ser Ala Ser Gly Arg Tyr Leu Cys
                245                 250                 255

Thr Asn Gly Ile Tyr Gln Phe Gly Asp Phe Ala Asp Arg Val Ser Lys
            260                 265                 270

Leu Phe Pro Glu Phe Pro Val His Ser Phe Ile Gly Glu Thr Gln Pro
        275                 280                 285

Gly Leu Thr Thr Cys Lys Asp Ala Ala Lys Arg Leu Ile Glu Leu Gly
    290                 295                 300

Leu Val Phe Thr Pro Val Glu Asp Ala Val Gly Glu Ser Val Glu Ser
305                 310                 315                 320

Leu Gln Ala Lys Gly Phe Leu Lys His Lys Thr Ser Glu Ser
                325                 330
```

<210> SEQ ID NO 89
<211> LENGTH: 318
<212> TYPE: PRT
<213> ORGANISM: Arabidopsis thaliana

<400> SEQUENCE: 89

```
Met Ala Lys Glu Thr Val Cys Val Thr Gly Ala Asn Gly Phe Ile Gly
1               5                   10                  15

Ser Trp Ile Ile Arg Thr Leu Ile Glu Lys Gly Tyr Thr Lys Ile His
            20                  25                  30

Ala Ser Ile Tyr Pro Gly Ser Asp Pro Thr His Leu Leu Gln Leu Pro
        35                  40                  45

Gly Ser Asp Ser Lys Ile Lys Ile Phe Glu Ala Asp Leu Leu Asp Ser
    50                  55                  60

Asp Ala Ile Ser Arg Ala Ile Asp Gly Cys Ala Gly Val Phe His Val
65                  70                  75                  80

Ala Ser Pro Cys Thr Leu Asp Pro Val Asp Pro Glu Lys Glu Leu
                85                  90                  95

Val Glu Pro Ala Val Lys Gly Thr Ile Asn Val Leu Glu Ala Ala Lys
            100                 105                 110

Arg Phe Asn Val Arg Arg Val Val Ile Thr Ser Ser Ile Ser Ala Leu
        115                 120                 125

Val Pro Asn Pro Asn Trp Pro Glu Lys Val Pro Val Asp Glu Ser Ser
    130                 135                 140

Trp Ser Asp Leu Asp Phe Cys Lys Ser Arg Gln Lys Trp Tyr Pro Ile
145                 150                 155                 160

Ser Lys Thr Leu Ala Glu Lys Ala Ala Trp Glu Phe Ser Glu Lys His
                165                 170                 175

Gly Thr Asn Ile Val Thr Ile His Pro Ser Thr Cys Leu Gly Pro Leu
            180                 185                 190

Leu Gln Pro Asn Leu Asn Ala Ser Cys Ala Val Leu Leu Gln Leu Leu
        195                 200                 205

Gln Gly Ser Thr Glu Thr Gln Glu His His Trp Leu Gly Val Val His
    210                 215                 220

Val Lys Asp Val Ala Lys Gly His Val Met Leu Phe Glu Thr Pro Asp
```

```
                  225                 230                 235                 240

Ala Ser Gly Arg Phe Leu Cys Thr Asn Gly Ile Tyr Gln Phe Ser Glu
                245                 250                 255

Phe Ala Ala Leu Val Ser Lys Leu Phe Pro Glu Phe Ala Val His Lys
            260                 265                 270

Phe Asp Lys Glu Thr Gln Pro Gly Leu Thr Ser Cys Asn Asp Ala Ala
        275                 280                 285

Lys Arg Leu Ile Glu Leu Gly Leu Val Phe Thr Ala Val Glu Asp Ala
    290                 295                 300

Val Lys Glu Thr Val Gln Ser Leu Arg Asp Lys Gly Phe Leu
305                 310                 315

<210> SEQ ID NO 90
<211> LENGTH: 529
<212> TYPE: PRT
<213> ORGANISM: Eucalyptus globules

<400> SEQUENCE: 90

Met Asp Ile Phe Tyr Phe Tyr Ser Gln Leu Gln Ser Leu Val Gln Thr
1               5                   10                  15

Gln Leu Gln Gln Ser Pro Met Thr Leu Leu Ser Val Val Pro Leu
            20                  25                  30

Leu Leu Phe Leu Gly Leu Val Ala Arg Leu Arg Arg Lys Pro Pro Phe
        35                  40                  45

Pro Pro Gly Pro Arg Gly Leu Pro Val Ile Gly Asn Met Leu Met Met
    50                  55                  60

Gly Glu Leu Thr His Arg Gly Leu Ala Ser Leu Ala Lys Lys Tyr Gly
65                  70                  75                  80

Gly Ile Phe His Leu Arg Met Gly Phe Leu His Met Val Ala Val Ser
                85                  90                  95

Ser Pro Asp Val Ala Arg Gln Val Leu Gln Val His Asp Gly Ile Phe
            100                 105                 110

Ser Asn Arg Pro Ala Thr Ile Ala Ile Ser Tyr Leu Thr Tyr Asp Arg
        115                 120                 125

Ala Asp Met Ala Phe Ala His Tyr Gly Pro Phe Trp Arg Gln Met Arg
    130                 135                 140

Lys Leu Cys Val Met Lys Leu Phe Ser Arg Lys Arg Ala Glu Ser Trp
145                 150                 155                 160

Glu Ser Val Arg Asp Glu Val Asp Thr Met Val Arg Thr Val Ala Gly
                165                 170                 175

Ser Glu Gly Thr Ala Val Asn Ile Gly Glu Leu Val Phe Glu Leu Thr
            180                 185                 190

Arg Asp Ile Ile Tyr Arg Ala Ala Phe Gly Thr Ser Ser Thr Glu Gly
        195                 200                 205

Gln Asp Glu Phe Ile Ser Ile Leu Gln Glu Phe Ser Lys Leu Phe Gly
    210                 215                 220

Ala Phe Asn Ile Ala Asp Phe Ile Pro Tyr Leu Ser Trp Ile Asp Pro
225                 230                 235                 240

Gln Gly Leu Thr Ala Arg Leu Val Lys Ala Arg Gln Ser Leu Asp Gly
                245                 250                 255

Phe Ile Asp His Ile Ile Asp Asp His Met Asp Lys Lys Arg Asn Lys
            260                 265                 270

Thr Ser Ser Gly Gly Gly Asp Gln Glu Val Asp Thr Asp Met Val Asp
        275                 280                 285
```

```
Asp Leu Leu Ala Phe Tyr Ser Asp Glu Ala Lys Val Asn Glu Ser Asp
    290                 295                 300

Asp Leu Gln Asn Ser Ile Arg Leu Thr Arg Asp Asn Ile Lys Ala Ile
305                 310                 315                 320

Ile Met Asp Val Met Phe Gly Gly Thr Glu Thr Val Ala Ser Ala Ile
                325                 330                 335

Glu Trp Ala Met Ala Glu Leu Met Arg Ser Pro Glu Asp Leu Lys Lys
                340                 345                 350

Val Gln Gln Glu Leu Ala Asp Val Gly Leu Asp Arg Arg Val Glu
                355                 360                 365

Glu Ser Asp Phe Glu Lys Leu Thr Tyr Leu Lys Cys Cys Leu Lys Glu
    370                 375                 380

Thr Leu Arg Leu His Pro Pro Ile Pro Leu Leu Leu His Glu Thr Ala
385                 390                 395                 400

Glu Asp Ala Val Ile Ser Gly Tyr Arg Ile Pro Ala Arg Ser Arg Val
                405                 410                 415

Met Ile Asn Ala Trp Ala Ile Gly Arg Asp Pro Gly Ser Trp Thr Glu
                420                 425                 430

Pro Asp Lys Phe Lys Pro Ser Arg Phe Leu Glu Ser Gly Met Pro Asp
                435                 440                 445

Tyr Lys Gly Ser Asn Phe Glu Phe Ile Pro Phe Gly Ser Gly Arg Arg
    450                 455                 460

Ser Cys Pro Gly Met Gln Leu Gly Leu Tyr Ala Leu Asp Met Ala Val
465                 470                 475                 480

Ala His Leu Leu His Cys Phe Thr Trp Glu Leu Pro Asp Gly Met Lys
                485                 490                 495

Pro Ser Glu Met Asp Met Gly Asp Val Phe Gly Leu Thr Ala Pro Arg
                500                 505                 510

Ser Thr Arg Leu Val Ala Val Pro Thr Pro Arg Leu Val Gly Ala Leu
    515                 520                 525

Tyr

<210> SEQ ID NO 91
<211> LENGTH: 443
<212> TYPE: PRT
<213> ORGANISM: Populus trichocarpa

<400> SEQUENCE: 91

Gly Leu Phe His Met Arg Met Gly Tyr Leu His Met Val Ala Gly Ser
1               5                   10                  15

Ser Pro Glu Val Ala Arg Gln Val Leu Gln Val Gln Asp Asn Met Phe
                20                  25                  30

Ser Asn Arg Pro Ala Asn Ile Ala Ile Ser Tyr Leu Thr Tyr Asp Arg
            35                  40                  45

Ala Asp Met Ala Phe Ala His Tyr Gly Pro Phe Trp Arg Gln Met Arg
        50                  55                  60

Lys Leu Cys Val Met Lys Leu Phe Ser Arg Lys Ala Glu Ser Trp
65                  70                  75                  80

Glu Ser Val Arg Asp Glu Val Asp Ser Met Val Lys Thr Val Glu Ser
                85                  90                  95

Asn Ile Gly Lys Pro Val Asn Val Gly Glu Leu Ile Phe Thr Leu Thr
                100                 105                 110

Met Asn Ile Thr Tyr Arg Ala Ala Phe Gly Ala Lys Asn Glu Gly Gln
            115                 120                 125
```

Asp Glu Phe Ile Lys Ile Leu Gln Glu Phe Ser Lys Leu Phe Gly Ala
            130                 135                 140

Phe Asn Ile Ser Asp Phe Ile Pro Trp Leu Gly Trp Ile Asp Pro Gln
145                 150                 155                 160

Gly Leu Thr Ala Arg Leu Val Lys Ala Arg Lys Ala Leu Asp Lys Phe
                165                 170                 175

Ile Asp His Ile Ile Asp His Ile Gln Lys Arg Lys Gln Asn Asn
            180                 185                 190

Tyr Ser Glu Glu Ala Glu Thr Asp Met Val Asp Met Leu Thr Phe
            195                 200                 205

Tyr Ser Glu Glu Thr Lys Val Asn Glu Ser Asp Leu Gln Asn Ala
210                 215                 220

Ile Lys Leu Thr Arg Asp Asn Ile Lys Ala Ile Ile Met Asp Val Met
225                 230                 235                 240

Phe Gly Gly Thr Glu Thr Val Ala Ser Ala Ile Glu Trp Ala Met Ala
                245                 250                 255

Glu Leu Leu Lys Ser Pro Glu Asp Ile Lys Arg Val Gln Gln Glu Leu
            260                 265                 270

Ala Asp Val Val Gly Leu Glu Arg Arg Val Glu Glu Ser Asp Phe Asp
            275                 280                 285

Lys Leu Thr Phe Phe Lys Cys Thr Leu Lys Glu Thr Leu Arg Leu His
290                 295                 300

Pro Pro Ile Pro Leu Leu Leu His Glu Thr Ser Glu Asp Ala Glu Val
305                 310                 315                 320

Ala Gly Tyr Tyr Val Pro Lys Lys Thr Arg Val Met Ile Asn Ala Tyr
                325                 330                 335

Ala Ile Gly Arg Asp Lys Asn Ser Trp Glu Asp Pro Asp Ser Phe Lys
            340                 345                 350

Pro Ser Arg Phe Leu Glu Pro Gly Val Pro Asp Phe Lys Gly Asn His
            355                 360                 365

Phe Glu Phe Ile Pro Phe Gly Ser Gly Arg Arg Ser Cys Pro Gly Met
370                 375                 380

Gln Leu Gly Leu Tyr Ala Leu Asp Leu Ala Val Ala His Leu Leu His
385                 390                 395                 400

Cys Phe Thr Trp Glu Leu Pro Asp Gly Met Lys Pro Ser Glu Leu Asp
                405                 410                 415

Met Thr Asp Met Phe Gly Leu Thr Ala Pro Arg Ala Thr Arg Leu Val
            420                 425                 430

Ala Val Pro Arg Lys Arg Val Val Cys Pro Leu
            435                 440

<210> SEQ ID NO 92
<211> LENGTH: 365
<212> TYPE: PRT
<213> ORGANISM: Gossypium hirsutum

<400> SEQUENCE: 92

Met Gly Ser Thr Gly Glu Thr Gln Met Thr Pro Thr Gln Val Ser Asp
1               5                   10                  15

Glu Glu Ala Asn Leu Phe Ala Met Gln Leu Thr Ser Ala Ser Val Leu
            20                  25                  30

Pro Met Val Leu Lys Ser Ala Ile Glu Leu Asp Leu Leu Glu Ile Met
            35                  40                  45

Ala Lys Ala Gly Pro Gly Ala Phe Leu Ser Pro Lys Glu Leu Ala Ser
50                  55                  60

```
Gln Leu Pro Thr Ser Asn Pro Asp Ala Pro Val Met Leu Asp Arg Ile
 65                  70                  75                  80

Leu Arg Leu Leu Ala Thr Tyr Ser Ile Leu Thr Cys Ser Leu Arg Thr
             85                  90                  95

Leu Pro Asp Gly Lys Val Glu Arg Leu Tyr Gly Leu Gly Pro Val Cys
            100                 105                 110

Lys Phe Leu Thr Lys Asn Glu Asp Gly Val Thr Leu Ser Ala Leu Ser
        115                 120                 125

Leu Met Asn Gln Asp Lys Val Leu Met Glu Ser Trp Tyr Tyr Leu Lys
    130                 135                 140

Asp Ala Val Leu Glu Gly Gly Ile Pro Phe Asn Lys Val Tyr Gly Met
145                 150                 155                 160

Thr Ala Phe Glu Tyr His Gly Thr Asp Pro Arg Phe Asn Lys Val Phe
                165                 170                 175

Asn Arg Gly Met Ser Asp His Ser Thr Ile Thr Met Lys Lys Ile Leu
            180                 185                 190

Glu Thr Tyr Asp Gly Phe Glu Gly Leu Lys Thr Leu Val Asp Val Gly
        195                 200                 205

Gly Gly Thr Gly Ala Thr Leu Asn Met Ile Val Thr Lys His Pro Ser
    210                 215                 220

Ile Lys Gly Ile Asn Phe Asp Leu Pro His Val Ile Glu Asp Ala Pro
225                 230                 235                 240

Ala Tyr Pro Gly Val Glu His Val Gly Gly Asp Met Phe Glu Ser Val
                245                 250                 255

Pro Lys Gly Asp Ala Ile Phe Met Lys Trp Ile Cys His Asp Trp Ser
            260                 265                 270

Asp Glu His Cys Ser Lys Phe Leu Lys Lys Cys Tyr Glu Ala Leu Pro
        275                 280                 285

Asp Ser Gly Lys Val Ile Val Ala Glu Cys Ile Leu Pro Asp Tyr Pro
    290                 295                 300

Asp Pro Ser Leu Ala Thr Lys Leu Val Val His Ile Asp Cys Ile Met
305                 310                 315                 320

Leu Ala His Asn Pro Gly Gly Lys Glu Arg Thr Glu Lys Glu Phe Glu
                325                 330                 335

Ala Leu Ala Arg Ser Ala Gly Phe Gln Gly Phe Gln Val Lys Cys Cys
            340                 345                 350

Ala Phe Gly Thr Tyr Ile Met Glu Phe Val Lys Arg Val
        355                 360                 365

<210> SEQ ID NO 93
<211> LENGTH: 366
<212> TYPE: PRT
<213> ORGANISM: Eucalyptus camaldulensis

<400> SEQUENCE: 93

Met Gly Ser Thr Gly Ser Glu Gln Met Thr Pro Thr Gln Val Ser
 1               5                  10                  15

Asp Glu Glu Ala Asn Leu Phe Ala Met Gln Leu Ala Ser Ala Ser Val
                 20                  25                  30

Leu Pro Met Val Leu Lys Ala Ala Ile Glu Leu Asp Leu Leu Glu Ile
             35                  40                  45

Met Ala Lys Ala Gly Pro Gly Ala Phe Leu Ser Pro Gly Glu Val Ala
     50                  55                  60

Ala Gln Leu Pro Thr Gln Asn Pro Glu Ala Pro Val Met Leu Asp Arg
```

-continued

```
                65                  70                  75                  80
            Ile Phe Arg Leu Leu Ala Ser Tyr Ser Val Leu Thr Cys Thr Leu Arg
                            85                  90                  95

Asp Leu Pro Asp Gly Lys Val Glu Arg Leu Tyr Gly Leu Ala Pro Val
                        100                 105                 110

Cys Lys Phe Leu Val Lys Asn Glu Asp Gly Val Ser Ile Ala Ala Leu
                    115                 120                 125

Asn Leu Met Asn Gln Asp Lys Ile Leu Met Glu Ser Trp Tyr Tyr Leu
                130                 135                 140

Lys Asp Ala Val Leu Glu Gly Gly Ile Pro Phe Asn Lys Ala Tyr Gly
            145                 150                 155                 160

Met Thr Ala Phe Glu Tyr His Gly Thr Asp Pro Arg Phe Asn Lys Ile
                            165                 170                 175

Phe Asn Arg Gly Met Ser Asp His Ser Thr Ile Thr Met Lys Lys Ile
                        180                 185                 190

Leu Glu Thr Tyr Lys Gly Phe Glu Gly Leu Glu Thr Val Val Asp Val
                    195                 200                 205

Gly Gly Gly Thr Gly Ala Val Leu Ser Met Ile Val Ala Lys Tyr Pro
                210                 215                 220

Ser Met Lys Gly Ile Asn Phe Asp Leu Pro His Val Ile Glu Asp Ala
            225                 230                 235                 240

Pro Pro Leu Pro Gly Val Lys His Val Gly Gly Asp Met Phe Val Ser
                            245                 250                 255

Val Pro Lys Gly Asp Ala Ile Phe Met Lys Trp Ile Cys His Asp Trp
                        260                 265                 270

Ser Asp Asp His Cys Ala Lys Phe Leu Lys Asn Cys Tyr Asp Ala Leu
                    275                 280                 285

Pro Asn Asn Gly Lys Val Ile Val Ala Glu Cys Val Leu Pro Val Tyr
                290                 295                 300

Pro Asp Thr Ser Leu Ala Thr Lys Asn Val Ile His Ile Asp Cys Ile
            305                 310                 315                 320

Met Leu Ala His Asn Pro Gly Gly Lys Glu Arg Thr Gln Lys Glu Phe
                            325                 330                 335

Glu Thr Leu Ala Lys Gly Ala Gly Phe Gln Gly Phe Gln Val Met Cys
                        340                 345                 350

Cys Ala Phe Gly Thr His Val Met Glu Phe Leu Lys Thr Ala
                    355                 360                 365
```